(12) United States Patent
Baier et al.

(10) Patent No.: US 8,807,164 B2
(45) Date of Patent: Aug. 19, 2014

(54) VALVE MODULE AND METHODS FOR SIMULATED MOVING BED CHROMATOGRAPHY

(75) Inventors: Joerg Werner Baier, Verona, WI (US); Robert Charles Mierendorf, Verona, WI (US); Anthony Charles Grabski, Blue Mounds, WI (US); Andrew Paul Wilke, Madison, WI (US); Anil Rajaram Oroskar, Oak Brook, IL (US)

(73) Assignee: Semba Biosciences, Inc., Madison, WI (US)

( * ) Notice: Subject to any disclaimer, the term of this patent is extended or adjusted under 35 U.S.C. 154(b) by 1385 days.

(21) Appl. No.: 11/847,971

(22) Filed: Aug. 30, 2007

(65) Prior Publication Data

US 2008/0053543 A1    Mar. 6, 2008

Related U.S. Application Data

(60) Provisional application No. 60/918,617, filed on Mar. 16, 2007, provisional application No. 60/841,296, filed on Aug. 30, 2006.

(51) Int. Cl.
*F16K 11/10* (2006.01)

(52) U.S. Cl.
USPC ............................ 137/597; 137/884; 251/61.1

(58) Field of Classification Search
USPC .......... 137/597, 606, 884, 494, 607; 251/61.1
See application file for complete search history.

(56) References Cited

U.S. PATENT DOCUMENTS

| | | | |
|---|---|---|---|
| 2,985,589 A | 5/1961 | Broughton et al. | |
| 4,182,633 A | 1/1980 | Ishikawa et al. | |
| 4,267,054 A | 5/1981 | Yoritomi et al. | |
| 4,304,257 A * | 12/1981 | Webster | 137/559 |
| 4,353,243 A * | 10/1982 | Martin | 73/23.42 |
| 4,434,051 A | 2/1984 | Golem | |
| 4,511,150 A | 4/1985 | Séguenot | |
| 4,522,726 A | 6/1985 | Berry et al. | |
| 4,614,204 A | 9/1986 | Dolejs | |
| 4,614,205 A | 9/1986 | Oroskar | |
| 4,625,763 A | 12/1986 | Schick et al. | |
| 4,632,149 A | 12/1986 | Oroskar et al. | |
| 4,633,904 A | 1/1987 | Schumann et al. | |
| 4,703,913 A | 11/1987 | Hunkapiller | |
| 4,705,627 A | 11/1987 | Miwa et al. | |
| 4,764,276 A | 8/1988 | Berry et al. | |
| 4,808,317 A | 2/1989 | Berry et al. | |
| 4,923,616 A | 5/1990 | Hirata et al. | |
| 5,122,275 A | 6/1992 | Rasche | |
| 5,156,736 A | 10/1992 | Schoenrock | |

(Continued)

OTHER PUBLICATIONS

Non-final Office Action for U.S. Appl. No. 11/847,997 dated Dec. 4, 2009.

(Continued)

*Primary Examiner* — Craig Schneider
*Assistant Examiner* — Kevin Murphy
(74) *Attorney, Agent, or Firm* — Foley & Lardner LLP

(57) ABSTRACT

The present invention provides devices and methods for micro-scale simulated moving bed chromatography (SMB) for continuous preparation of analytic quantities of highly pure fractions of target molecules. The present apparatus and method of the invention is adapted in a preferred embodiment to separations by affinity chromatography involving three discontinuous liquid flow loops. An alternative embodiment of affinity chromatography utilizes standard SMB operating under isocratic conditions.

10 Claims, 43 Drawing Sheets

(56) References Cited

U.S. PATENT DOCUMENTS

| | | | |
|---|---|---|---|
| 5,203,368 A * | 4/1993 | Barstow et al. ............... 137/240 |
| 5,395,879 A | 3/1995 | Murray |
| 5,456,825 A | 10/1995 | Negawa et al. |
| 5,465,748 A | 11/1995 | Bowers |
| 5,518,625 A | 5/1996 | Priegnitz et al. |
| 5,556,546 A | 9/1996 | Tanimura et al. |
| 5,565,104 A | 10/1996 | Priegnitz |
| 5,635,072 A | 6/1997 | Moran |
| 5,645,729 A | 7/1997 | Priegnitz et al. |
| 5,660,370 A * | 8/1997 | Webster ............... 251/129.17 |
| 5,676,826 A | 10/1997 | Rossiter et al. |
| 5,705,061 A | 1/1998 | Moran |
| 5,750,820 A | 5/1998 | Wei |
| 5,770,088 A | 6/1998 | Ikeda et al. |
| 5,775,371 A | 7/1998 | Pan et al. |
| 5,803,105 A * | 9/1998 | Wasson et al. .................... 137/1 |
| 5,884,777 A | 3/1999 | Pan et al. |
| 5,950,674 A * | 9/1999 | Wylie et al. ................. 137/597 |
| 6,102,068 A * | 8/2000 | Higdon et al. ............... 137/341 |
| 6,123,849 A | 9/2000 | Purdom |
| 6,146,537 A | 11/2000 | Ferschneider et al. |
| 6,162,949 A | 12/2000 | Gattuso |
| 6,224,776 B1 | 5/2001 | Heikkila et al. |
| 6,261,458 B1 | 7/2001 | Callebert et al. |
| 6,284,134 B1 | 9/2001 | Ferschneider et al. |
| 6,284,200 B1 | 9/2001 | Hotier |
| 6,348,637 B1 | 2/2002 | Harris |
| 6,379,554 B1 | 4/2002 | Kearney et al. |
| 6,402,959 B1 | 6/2002 | Dessapt et al. |
| 6,455,736 B1 | 9/2002 | Zinnen et al. |
| 6,458,955 B1 | 10/2002 | Gattuso |
| 6,508,938 B2 | 1/2003 | Maiefski et al. |
| 6,544,413 B1 | 4/2003 | Nagamatsu et al. |
| 6,548,662 B1 | 4/2003 | Ohsaki et al. |
| 6,551,512 B1 | 4/2003 | Britsch et al. |
| 6,572,775 B2 | 6/2003 | Heikkila et al. |
| 6,602,420 B2 | 8/2003 | Kearney et al. |
| 6,632,200 B2 | 10/2003 | Guo et al. |
| 6,652,755 B2 | 11/2003 | Ikeda |
| 6,712,973 B2 | 3/2004 | Adam et al. |
| 6,719,001 B2 | 4/2004 | Ahlgren et al. |
| 6,740,243 B2 | 5/2004 | Wankat |
| 6,752,929 B1 | 6/2004 | Zahr et al. |
| 6,770,757 B2 | 8/2004 | Paananen et al. |
| 6,779,557 B2 | 8/2004 | Weiss |
| 6,797,175 B2 | 9/2004 | Hotier |
| 6,805,799 B2 | 10/2004 | Ma |
| 6,834,854 B2 | 12/2004 | Inoue et al. |
| 6,843,854 B2 | 1/2005 | Farrenburg et al. |
| 6,875,349 B2 | 4/2005 | Heikkila et al. |
| 6,896,811 B2 | 5/2005 | Heikkila et al. |
| 6,896,812 B1 | 5/2005 | Frey |
| 6,951,340 B2 | 10/2005 | Suzuki et al. |
| 6,979,402 B1 | 12/2005 | Sprague et al. |
| 7,141,172 B2 | 11/2006 | Wang et al. |
| 7,220,356 B2 | 5/2007 | Thommes et al. |
| 2003/0036637 A1 | 2/2003 | Fulton |
| 2003/0146401 A1 * | 8/2003 | Wetzel et al. ................. 251/61.1 |
| 2004/0102380 A1 | 5/2004 | Fulton et al. |
| 2004/0241878 A1 | 12/2004 | Thommes et al. |
| 2005/0098962 A1 | 5/2005 | Duclos et al. |
| 2005/0194318 A1 | 9/2005 | Ozbal et al. |
| 2006/0185419 A1 | 8/2006 | Gamache et al. |
| 2007/0131615 A1 | 6/2007 | Moran et al. |
| 2007/0215534 A1 | 9/2007 | Thommes et al. |
| 2008/0053543 A1 | 3/2008 | Baier et al. |
| 2008/0053901 A1 | 3/2008 | Mierendorf et al. |
| 2008/0053917 A1 | 3/2008 | Larson et al. |

OTHER PUBLICATIONS

International Search Report and Written Opinion for International Application No. PCT/US2007/019126 dated Mar. 4, 2008.
Notice of Allowance received for U.S. Appl. No. 11/847,983 dated Apr. 7, 2010.
Notice of Allowance received for U.S. Appl. No. 11/847,997 dated Jun. 2, 2010.
Examiner's Report issued in European Patent Application No. 07852396.6 dated Jul. 25, 2013 (5 pages).
Extended European Search Report issued in European Application No. 07852396.6 dated Nov. 4, 2011 (10 pages).

* cited by examiner

STEP MODE

ISOCRATIC MODE

FIG. 35

TEST #3 DATA - FLOWRATE AS FUNCTION OF PRESSURE
8.9.06, SBA-T01, Phase 1, BIT 7 Inc.

| | Flowrate of Water (ml/min) | | | | | | |
|---|---|---|---|---|---|---|---|
| Pressure Difference (psi) | Valveblock Only | | | | | Valveblock + Column | |
| | Outlet = Port 5 | Outlet = Port 6 | Outlet = Port 7 | Outlet = Port 8 | Outlet = Port 10 | Single Column | 4 Columns in Series |
| 1.0 | 1.2 | 2.5 | 1.6 | 2.0 | 3.9 | 1.6 | 0.67 |
| 3.0 | 5.0 | 6.2 | 5.8 | 5.5 | 8.2 | 5.1 | 2.2 |
| 5.0 | 9.2 | 10.5 | 11.5 | 10.2 | | 7.8 | 3.3 |
| 10.0 | 23.0 | 25.0 | 25.0 | 22.0 | | | 5.5 |
| 20.0 | | | | | | | 10.5 |

Notes:
1. Inlet = Port 9 for all trials
2. Membrane is 0.010" thick FEP
3. Accuracy of pressure difference = +/- 1.5 psi
4. Accuracy of water flowrate +/- 10%
5. Dimple size = 0.166" x 0.328" x 0.028" (oval shaped)
6. Port dia = 0.031" through valve block sandwich
7. Primary flow channel within valve block = 0.026" x 0.031"
8. Approx 18" length of 0.031"ID tubing between P taps
9. Columns attached to Port 10; ports 5 – 8 closed during "column trials"
10. Columns = Novagen CoMAC cartridge 71650, Lot # N63282

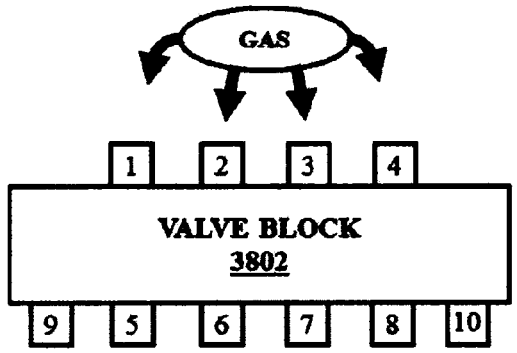

FIG. 38

VALVE MODULE AND METHODS FOR SIMULATED MOVING BED CHROMATOGRAPHY

This application claims the benefit of U.S. Prov. Appl. 60/918,617, filed Mar. 16, 2007 and U.S. Prov. Appl. 60/841,296, filed Aug. 30, 2007, both of which are incorporated by reference herein in their entirety.

FIELD OF THE INVENTION

The present invention relates to small-scale simulated moving bed chromatography (SMB) for continuous preparation of highly pure fractions of target molecules. The present apparatus and method of the invention are adapted in an embodiment to separations by chromatography involving discontinuous liquid flow loops. A preferred embodiment of affinity chromatography utilizes SMB operating under isocratic conditions.

BACKGROUND OF THE INVENTION

Simulated moving bed chromatography (SMB) was first described in U.S. Pat. No. 2,985,589. The specification discloses a separation tower divided into a number of individual interconnecting separation beds containing solid phase chromatography substrates. An inline pump at the bottom of the tower connects flow from the bottom to the top, thereby providing a continuous loop. Inlet ports for feedstock (F) and Desorbent (D) and exit ports for Raffinate (R) and Extract (E) are placed at specific points in the series of separation beds. At defined intervals, the position of the beds is switched in the opposite direction from the flow, producing a countercurrent movement of the solid phase beds relative to the fluid streams. Feedstock (F) introduced into the first bed begins to separate into components contained therein as flow ensues, with less retained species migrating in the direction of fluid flow and being collected at the Raffinate port. The more retained species remain preferentially associated with the solid phase and are collected at the Extract port. By regulating the switch times and flow rates of F, D, R, and E, a standing wave pattern is established, allowing for continuous flow of purified products from the system.

The basic SMB process is further illustrated schematically in FIG. 1. At the top of the diagram, feed depicted as a mixture of solid and open circles is introduced between chromatographic columns 1 and 8 with the direction of fluid flow clockwise, and column switching counterclockwise. In Zones II and III (columns 7, 8, 1, and 2) separation of species occurs, and the open circles exit the system in the raffinate at the three o'clock position. Desorbent is introduced at six o'clock, and flows clockwise into the system. As the columns rotate, purified closed circle species is drawn off in the extract at the nine o'clock position.

Historically, SMB has been typically applied to large scale industrial binary separations. The process in the '589 patent was applied to the industrial scale separation of cyclohexane from n-hexane. More recently SMB has found favor in separating sugar isomers, hydrocarbons, solvents, and other industrial applications. Many of these industrial devices, like the original '589 device, employ variations of mechanical rotary valves in effecting column switching. The valve components are arranged so that at any given valve position, multiple inlet and outlet flows are directed to predetermined columns, and advanced one position correspondingly with each rotational step. Such rotary valves are disclosed in U.S. Pat. Nos. 6,719,001, 4,574,840, and 4,614,205. To emphasize the intended scale of some of these devices, refer to U.S. Pat. No. 3,040,777 which describes a valve occupying an area of 64 sq. feet and weighing 10 tons.

One of the frequent problems with rotary valves is a tendency to leak at the junction of the rotating member and the stator element. To eliminate this problem many attempts have sought to replace a mechanical valve with a complex series of interconnecting individual valves. Two such valve systems are disclosed in U.S. Pat. Nos. 4,434,051 and 5,635,072. For scale-down of SMB using networks of individual valves, another problem arises, namely, accumulating too much void volume in the connecting lines which interferes with separation. Another U.S. Pat. No. 6,544,413, however, discloses a plural valve device having clustered valve assemblies of four valves for control of inputs/outputs proximately to each chromatographic bed. It has the advantage of reducing volume of liquid for small scale SMB systems. U.S. Pat. No. 6,979,402 discloses a device in which cross-over conduits are replaced entirely by connecting channels machined into the top and bottom plates of the rotary valve body and aligned with column ports to create an SMB fluid loop, thus reducing void volume. However, it is unclear from this disclosure how small the contact surface of the valve components can be to obtain adequate sealing.

There has been a recent trend in scaling SMB down to pilot and sub-pilot volumes, as more sophisticated applications have arisen in the fine chemicals and pharmaceutical fields requiring milligram-to-gram level quantities of product. Several recent applications of SMB to the purification of pharmaceutically active diastereomers and enantiomers have been disclosed in U.S. Pat. Nos. 6,462,221, 6,461,858, 6,458,995, and 6,455,736. Uses of new chiral resins in SMB for binary separations of such molecules are becoming commonplace. SMB is also beginning to be considered for purification of biomolecules from complex mixtures. For example, purification of monoclonal antibodies using SMB has been reported in Gottschlich, et al., J. Chromo. A, 765 (1997) 201 and disclosed in WO 2004/024284. Standing wave strategies based on SMB have been developed for insulin purification, as reported by Mun, et al., Biotechnol. Prog., 18 (2000) 1332.

The Protein Structure Initiative is a national effort to determine the three-dimensional structure of a wide variety of proteins. This information will accelerate the discovery of protein function and enable faster development of new therapies for treating genetic and infectious diseases. Begun in 2000, this decade-long project has recently entered its second phase. In the second phase, ten new centers will participate in addition to the first nine. One of the significant challenges is to develop methods of purifying target proteins from complex cell extracts in small (10-100 mg) quantities, in high purity (greater than 90%). Basic structural analyses by techniques such as x-ray crystallography and NMR spectroscopy require that standard. A clear need exists for an SMB device that is capable of purifying target small molecules and biomolecules in low (multi-milligram) amounts which avoid mechanical components that leak and large void volumes that interfere with purity, while embodying the hallmarks of SMB, which are controlled purity and continuous production.

SUMMARY OF THE INVENTION

The present invention fulfills design requirements for economy in liquid transfer from column to column and for simplicity in valve function without a need for moving parts prone to leaks. It is an object of the invention to provide such a device scalable to accommodate small columns capable of purifying milligram-to-gram quantities of target substances.

It is a further object to provide an SMB device having simple, easily programmable controls, and which is easy to repair and maintain.

The basic element of the invention is the valve system. In its simplest form, a group of valves or valve block consists of two plates having specialized grooves and bores wherein a pliant diaphragm is used to control fluid flow. A metal or plastic lower plate contains a common groove etched into a flat upper surface terminating at each end in vertical bores extending perpendicularly to the lower surface terminating in fluid connectors. The lower plate also has one or more bores offset from the common groove. A valve diaphragm made of a pressure responsive material is placed on top of the plate. An upper plate contains bores from its top surface extending through the plate and terminating in small recesses or dimples on the undersurface. These recesses are in alignment with the offset bores and also encompass a portion of the common groove on the lower plate. The components are fastened together. When pneumatic pressure is applied to the upper plate bores, the diaphragm is urged against the upper surface of the lower plate effectively sealing the bore.

In operation, inlet liquid flowing into one of the lower plate bores travels up, and traverses the common groove before exiting the second lower plate bore. If liquid is to be withdrawn from or introduced into the system through an offset bore, the pneumatic pressure is released and the diaphragm deflects partially into the recess, exposing a liquid communicating channel between the offset bore and the common channel; causing liquid to exit or enter through the corresponding offset bore.

The simple valve configuration described above enables control of multiple fluid ingress and egress streams between two adjacent components, such as chromatography columns. In SMB it is necessary to switch a minimum of four flow streams (Feed, Raffinate, Desorbent, Extract) between a minimum of four columns. Thus, in order to construct the connections required for SMB with the above simple valve configuration, separate ingress and egress lines would be required for each pair of columns, which would in turn require separate flow control devices, manifolds, or additional valves for each line and add significant void volume. The invention herein described overcomes these limitations by incorporating a series of ingress and egress channels into the valve block to enable access to any number of columns through common lines. This valve configuration of the present invention has several advantages in miniaturized SMB. First, all of the column inputs and outputs for any column can be arranged along a common groove joining the flow between any two columns. Second, inlet and outlet valves can be arranged in high density thereby minimizing void volume in the system. Third, the device has no moving parts per se. Maintenance is virtually non-existent. In the event that the diaphragm becomes scratched and begins to leak, it is easily replaced.

In the annular configuration of the present invention, a number of ingress and egress channels are arranged substantially in concentric circles to minimize the path length of the connecting flow pathway between columns. In standard SMB, defined as a system having a continuous uninterrupted liquid loop interconnecting all of the columns, there are minimally four columns, but systems can be constructed to any number. Some known SMB systems operate with as many as thirty two columns. In what is here termed affinity or discontinuous SMB mode, there are two or more separate discontinuous liquid loops operating simultaneously. In either case, the complete system has two annular valve block modules, one in inverted orientation with respect to the other, and aligned so that columns are sandwiched between the two modules.

The annular valve block module containing a plurality of valves is made up of several functional layers which are securely fastened together. The upper plate has top and bottom surfaces and containing a number of bores arranged radially and extending perpendicularly from the top surface to terminate in recesses on the bottom surface. The bottom surface interfaces with a pliant diaphragm, which in turn contacts the upper surface of a fluid transfer plate. The fluid transfer plate has upper and lower surfaces with grooves etched on both surfaces. The grooves on the upper surface, the functional equivalent of the common channel referred to above, have bores within the groove at the very ends of the groove, so that each groove terminates in a bore at both ends. The upper surface grooves are preferably facing to the perimeter of the fluid transfer plate to allow maximum space for the columns in the complete SMB unit. There are also a series of offset bores arranged spacedly in liquid flow proximity to the grooves, and are aligned substantially centrally with the recesses of the manifold. These bores extend through the fluid transfer plate and communicate with two or more concentric circular ingress and egress channels etched on the lower surface of the fluid transfer plate. The concentric channels may be continuous or consist of circular arcs that terminate at or near the offset bores that communicate with adjacent columns.

The valve diaphragm is comprised of a pliant pressure responsive material, preferably a fluorpolymer, disposed between the upper plate bottom surface and fluid transfer plate upper surface. When pneumatic pressure is applied, this diaphragm is urged against the fluid transfer plate in sealing engagement, and when pressure is released, it deflects into the recess in the upper plate due to pressure from the fluid flow.

An anchor plate which forms the bottom layer in the assembled module provides strength to ensure sealing of the interfaces between layers of the module. It has upper and lower surfaces containing column communicating bores in corresponding alignment to the vertical fluid transfer plate bores, and access ports that align with the ingress and egress channels on the fluid transfer plate. Optionally, there may be a barrier membrane forming a sealing interface at the lower surface of the fluid transfer plate which forms a barrier wall for the circular channels also containing column access ports to communicate with aligned columns and the fluid ingress and egress channels.

In affinity or discontinuous chromatography the process requirements are different than for standard SMB. For improved purity and yields, it is important to thoroughly wash columns to which target is bound before eluting. Further it is essential to wash columns from which target has been eluted to regenerate the columns for the next cycle of adsorption. This is accomplished by including one or more isolated loops which allow washing of columns when they enter into the pre-elution and regeneration zones. The annular valve block module for discontinuous SMB has structures for upper plate, valve diaphragm, optional barrier plate, and anchor plate substantially identical to that for standard SMB.

The fluid transfer plate has different features. In one embodiment the grooves on the upper surface are radial, U-shaped, and terminate on one end in a first column communicating bore extending to the lower surface of the fluid transfer plate, and at the other end, a second offset column communicating bore in substantially central alignment to a recessed bore of the pressure manifold in liquid flow proximity to the U-shaped groove. In a preferred embodiment there are a total of eight such bores for each column, four of which reside on one valve block module for the inlet streams, and four of which reside on the other valveblock module for the outlet streams. As a flow stream enters the valve block it has access to any of the columns via its ingress channel, which communicates with the offset bores in the fluid transfer plate. When it encounters an open port it proceeds through the offset bore to the upper surface of the fluid transfer plate, into the U-shaped groove, and then to the column inlet port. After exiting the column, it flows through the U-shaped groove on the other valve block module, through the bore of any open outlet valve, through the appropriate egress channel, and out of the valve block to the collection reservoir.

In addition to the inlet and outlet valves comprised of offset bores communicating with the U-shaped groove, another valve is required for controlling the flow of one column to the next. This valve, the cutoff valve, is constructed by interrupting the U-shaped groove on the upper surface of the fluid transfer plate, such that a gap is formed, preferably at the downstream end of the last outlet valve and before the first inlet valve of the next column. The valve is actuated via a corresponding dimple in the lower surface of the upper pneumatic plate which spans the ends of the interrupted channel and does not utilize an offset bore. Thus when pneumatic pressure is applied the diaphragm seals the gap between the ends of the channel and flow to the next column is prevented. The cutoff valves enable one or more columns to be segregated from fluid contact with the rest of the columns for the purpose of using different solvent or buffer streams, such as in discontinuous protocols requiring different buffer conditions for binding, washing, elution, and regeneration of column beds.

A complete standard SMB device for recovery of components of feedstock separated in a raffinate or extract has means for providing a pressure force to the pressure manifold, and fluid diversion means to regulate pressure against the various individual valve sites on a valve diaphragm corresponding to the recesses of the pressure manifold. The device also utilizes two annular block modules wherein one module is aligned with a second module in inverted orientation. The modules are interconnected to a plurality of chromatographic columns attached to column communicating bores in equal number, so as to create an end-to-end continuous fluid loop in the system. One or more check valves are positioned to direct fluid flow in the desired direction. Pressure means such as an air driven cylinder or a pump propels liquid from reservoirs into the access ports at pre-selected positions. Outlet restrictive means permit regulation of the internal operating pressures, and also permit adjustment of the relative output volumes. Outlet restrictive means includes a pump as well as devices which constrict the diameter of the outlet ports. The device is held together by fastening means to traverse the block modules to maintain alignment and prevent leaks in fluid movement. Finally, there are control means to switch the valving according to a pre-determined sequence.

The device for purifying biological substances by affinity or discontinuous chromatography similarly has means for providing a pressure to a manifold having fluid diversion means to regulate pressure against the individual valve sites on a valve diaphragm corresponding to the recesses of the pressure manifold for discontinuous mode. The device is composed of two annular block modules wherein one module is aligned with a second module in inverted orientation interconnected by a plurality of chromatographic columns attached to the column communicating bores of equal number. Pressure means are provided to direct flow of liquid to the pre-selected access ports of the modules, and egress means permit collection of wash solution from the regeneration zone and eluate and raffinate. Fastening means traversing the block modules to maintain alignment and prevent leaks in fluid movement. One or more check valves may optionally be placed in line to direct and enhance proper flow. Finally, control means direct the switching of valving according to a predetermined sequence. In both standard SMB and discontinuous modes, the means of exerting pressure in the pressure manifold may be either pneumatic or hydraulic.

The same device may also be configured to perform various combinations of standard SMB and discontinuous modes. For example, a discontinuous loop may be included in a two-column a section of an eight-column SMB device for the purpose of cleaning the columns, with the other six employed in a continuous SMB separation. As another example, a discontinuous protocol may be employed as the first step in purification, followed by standard SMB using a different protocol in the same device as the second step.

In one embodiment, there is an advantage in providing a separate solenoid valve block and manifold for each valve block module. The type and pressure rating of the solenoids can easily be modified by substituting a different block in different applications. This has, of course, the disadvantage of requiring individual pneumatic or hydraulic tubes to be extended from the solenoid block to each pneumatic valve port on the device. Also individual wires to power each solenoid may be required.

In a preferred embodiment, these tubes and wires are eliminated completely so that a compact device contains within the valve module itself all pneumatic and electronic valve control features of the system. Such device has several component members, a pneumatic manifold plate assembly consisting of a pneumatic plate, an electronic circuit board, and a solenoid valve; a fluid transfer plate for directing flow of liquid through the columns and adding or drawing off liquids from the chromatography stream; a valve diaphragm for closing or opening selected valves at various intervals; a barrier plate to seal fluid ingress and egress channels; and an anchor plate to provide fluid attachment means for egress and ingress of fluids from the system.

The pneumatic plate has a first member having a top surface, bottom surface, and a core. The top surface has a plurality of raised, elongated pedestals arranged in parallel. The upper surface of the pedestals contains a plurality of bores arranged rectilinearly and extending perpendicularly from a pneumatic valve port terminating in recesses on the pneumatic plate bottom surface. A second perpendicular bore extends from a pneumatic manifold port on the upper pedestal to communicate with a transverse pressure channel embedded in the core of the plate. A pneumatic exhaust channel is contiguous to a pedestal relieves pressure to selected valves. The second member of the pneumatic plate is an electronic circuit board which has slots the size and shape of the pedestals so that when placed on a receiving surface on top of the first member pedestals, exposes the pedestal bores in alignment of the two members, which are secured by fastening means. The circuit board has receptacles for a third member solenoid body electrical conduits which mate together to form an electrical connection. The pneumatic valve ports, manifold ports and exhaust channels are adapted to align with the corresponding ports on the solenoid valve, and the contact of port orifices are sealed by gaskets. The precise positioning of ports on the upper surface of the pedestals will be dictated by the position of corresponding solenoid orifices for the type and brand of solenoid selected.

A second component of the valve module is a fluid transfer plate having an upper surface and a lower surface, the upper surface displaying a plurality of fluid transfer grooved channels etched thereon, terminating at each end in substantially vertical column port bores. These ports are arranged into rows of equal number along opposite sides of the plate extending to the lower surface of the plate in alignment with chromatographic columns situated at corresponding intervals under the module. In addition, there is an array of offset bores in liquid flow proximity to the grooved channels aligned to the recesses on the lower surface of the pneumatic plate, and extending through the transfer plate to communicate with two or more fluid ingress and egress channels etched the lower surface of the fluid transfer plate.

There is a valve diaphragm composed of a pliant pressure responsive material disposed between the lower surface of the pneumatic plate and the upper surface of the fluid transfer plate. The diaphragm lacks bores except where required for screws or other fasteners for holding the assembly together. There is a barrier plate forming a sealing interface at the lower surface of the fluid transfer plate, forming a lower barrier wall to the fluid egress and ingress channels. This plate also has column access bores to communicate with the aligned chromatographic columns and the ingress and egress channels. Finally there is an anchor plate having an upper and a lower surface containing column communicating bores in alignment with the chromatographic columns and the ingress and egress channels.

The chromatography device comprises two modules oriented in inverted configuration with columns connected between them by fitting means and attached at bores in the anchor plate. The upper surface of the fluid transfer plate design is different for the two modules, in order to allow the columns to be attached between them in a parallel orientation. In one fluid transfer plate the grooved channels on the upper surface are adapted to enable the outlet ports and cutoff valve from one column to communicate with the inlet ports of the next column in a different row level. In a preferred embodiment each grooved channel that represents the outlet ports for the columns on one valve block module is extended to the column outlet port one row below. This configuration enables the fluid path to proceed upward through each successive row of grooved channels into columns extending perpendicular to the valve block modules and parallel with each other. The grooved channel extension for the topmost column outlet is different in that it communicates back to the lowest row to complete the fluid loop. In the other fluid transfer plate the upper surface grooved channels do not contain extensions, and each column outlet port is at the same level as its row of valve outlets, which in turn communicate to the inlet valves and inlet port for the next column along the same level. The upper surface grooved channels of either fluid transfer plate may interrupted by gaps having ends that can be spanned by corresponding dimples in the lower surface of the pneumatic plate to form cutoff valves. The ends of the interrupted channels may be curved to provide liquid flow proximity between the ends when pressure is released in a pneumatic valve situated immediately above the gap.

The simulated moving bed device comprising the two valve modules also has means to apply a pressure force to a pneumatic plate having air diversion means or manifold to regulate pressure against individual sites on the valve diaphragm corresponding to the recesses of the pneumatic plate. The manifold is a transverse pressure channel contained in the core of the pneumatic plate. The two modules, left and right oriented, are interconnected by a plurality of chromatographic columns attached to the communicating access bores. The device further has pumping means to direct ingress or egress flow of liquid to and from pre-selected access ports of the module, and fastening means to maintain alignment and prevent fluid or pneumatic leaks.

Control of a system in accordance with the present invention preferably includes a personal computer running control software which provides a user-friendly interface for a user to control the valve state configuration. Preferably the control software allows the user to either manually control the valve configuration within a chromatography module or to set up and run automated scripts that direct changes in valve states that allow the chromatography module to separate and purify compounds. The personal computer interfaces with control electronics that act on control signals generated by the control software in response to the user inputs. The control electronics operate to actuate solenoids that control the gas or fluid pressure applied to each membrane valve to control the valve states in the system. Also controlled by the personal computer are pumps that direct the flow of fluid through the system. The pumps receive signals relayed to them through an adaptor board from the computer. Together, this control system configuration allows for complete automation of a chromatographic separation process using an SMB system in accordance with the present invention.

In the method of purifying biological substances by discontinuous or affinity SMB in which four zones of chromatography steps, namely, adsorption, wash, elution, and regeneration, wherein there is a discontinuous downstream propelled flow of fluid, and a regular countercurrent cycling of valve positions in recurrent stepwise configuration, a feedstock is applied to a first column which contains a target substance of interest. The target substance is permitted to bind to an immobilized ligand in the column through complementary affinity of a chemical moiety appended to the solid phase. In a preferred embodiment binding is performed in an isolated zone of one or more columns wherein the feedstock is applied at an inlet port of the first column and unbound material is removed at an outlet port of the last column. The isolated zone is established by closing appropriate cutoff valves to prevent flow from the column upstream of the zone and to the column downstream of the zone. Cutoff valves between columns within the zone are opened. Next, a majority portion of the unbound contaminants is removed in an isolated zone of one or more columns wherein a wash buffer is applied at an inlet port of the first column and the wash effluent is removed at an outlet port of the last column. In an alternative embodiment the cutoff valve between the wash zone and the binding zone is opened to allow the flow stream of wash buffer to combine with the feedstock. The next step is eluting the target substance in an isolated zone of one or more columns wherein an elution buffer is applied at an inlet port of the first column and the eluate is collected at an outlet port of the last column. The final step is regenerating the columns in an isolated zone of one or more columns wherein a regeneration buffer is applied at an inlet port of the first column and the effluent is removed at an outlet port of the last column. This process is repeated at each valve switch position of the device. It will be apparent to those skilled in the art that by appropriate configuration of valve positions in the sequence by control means, the affinity mode SMB device can be programmed to perform standard SMB as well.

In a preferred affinity chromatography method, standard SMB having inlets for feedstock and eluent and outlets for extract and raffinate is employed to isocratically purify an affinity tagged protein from a complex mixture of proteins in a feedstock by selecting a concentration of an affinity neutralizing agent sufficient to prevent static binding of the target to a resin contained in the multiple columns. At this selected concentration there is still some affinity interaction between the target protein and the resin sufficient to retard passage of the target protein through the resin in a mobile phase. This is in contrast to other proteins in the mixture not having such affinity, which readily pass into the raffinate. Thus, protein contaminants which would otherwise bind weakly to the resin in a static binding mode, are eliminated from the product stream. The concentration of affinity neutralizing agent is adjusted to the selected concentration in both the feedstock and eluent, so that the entire SMB process is carried out at one isocratic concentration. The feedstock is continuously fed into the SMB device to obtain purified target protein from the extract outlet. This method is useful also for purifying proteins having endogenous selective affinity for a ligand which is bound to a column resin. Examples include molecules having immune specificity with binding domains for protein A and G, enzyme-substrate binding sites, or co-factor binding sites. The method is particularly efficacious for recovery of monoclonal antibodies from cell culture, ascites fluid, or recombinant origins.

It will be apparent to those skilled in the art that the discontinuous and isocratic SMB modes can be applied in a variety of configurations with virtually any liquid chromatographic separation system, including, but not limited to; metal affinity, immunoaffinity, substrate affinity, anion or cation exchange, hydrophobic interaction, thiophilic, and recombinant protein affinity tag systems.

BRIEF DESCRIPTION OF THE DRAWINGS

FIG. 35 is a an exemplary screen shot illustration of a graphical user interface for defining the valve states for manual control in a control system in accordance with the present invention.

FIG. 38 shows an exemplary table of test data regarding flow rates through an example valve block, along with a drawing of the example valve block in accordance with an illustrative embodiment.

DETAILED DESCRIPTION OF THE PREFERRED EMBODIMENTS

Figure 1:
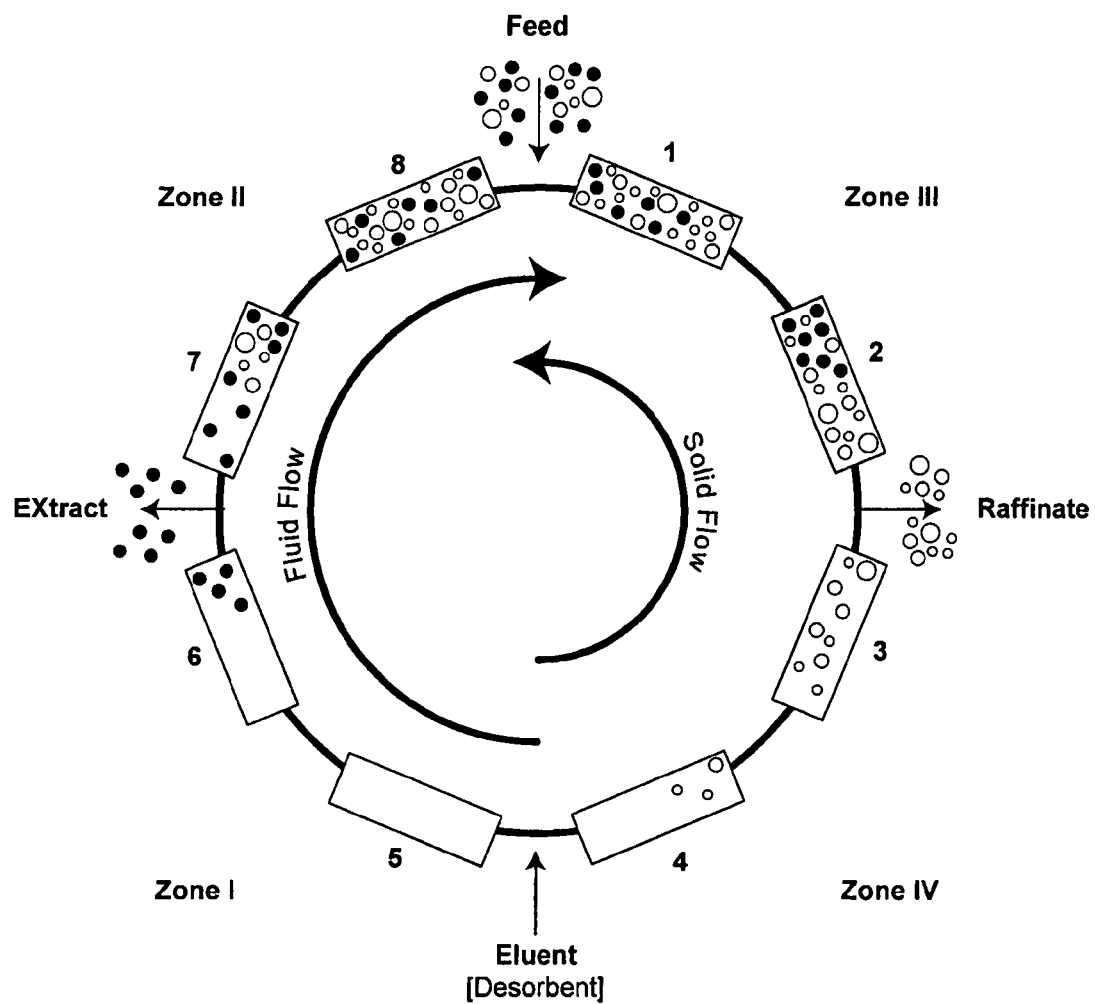
FIG. 1 is a schematic illustrating an eight column standard SMB system in a two species separation at one point in time for a 2-2-2-2 configuration.
Figure 2:
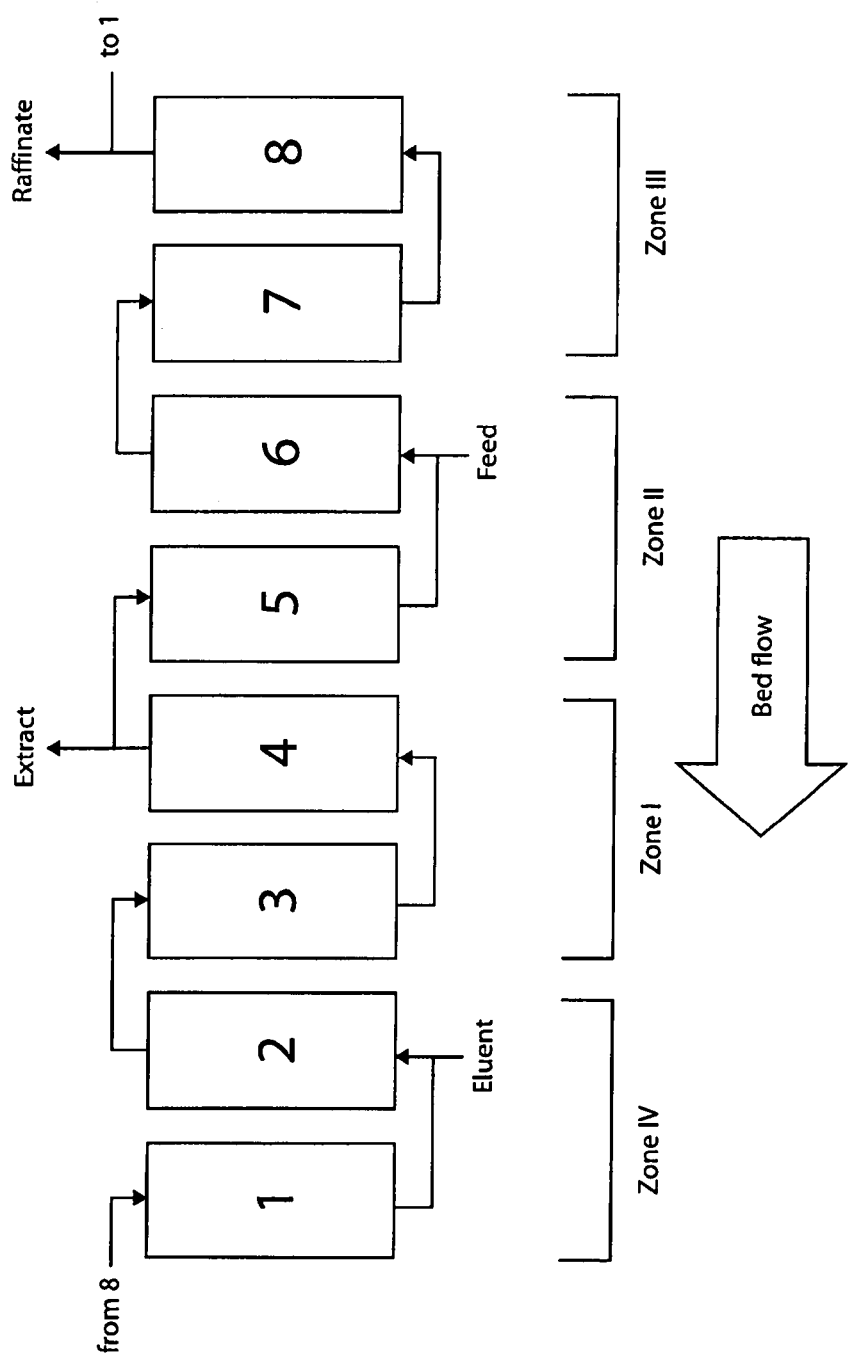
FIG. 2 is a diagram of an eight column standard SMB system showing the various chromatographic zones and the position of inputs and outputs for a 3-1-3-1 configuration.

The principle of continuous countercurrent chromatography relies on the phenomenon of preferential retention on an immobilized sorbent substrate of one or more substances in a feedstock mixture, separation of less retained substances, and subsequent recovery of the separated substances. In standard SMB this process is repeated in a succession of columns by switching zones of separation, enrichment, and regeneration in stepwise sequence. FIG. 2 is a schematic illustrating SMB in an eight column 3-1-3-1 configuration. The feedstock (F) enters the system between Zones II and III at column 6, and after passage through three columns, less retained substances are collected in the raffinate (R). At a predetermined interval, through valve switching, column 6 now occupies the position of column 5 in the diagram, and so on. Eluent (desorbent) which is carried by the left-to-right flow in the system through columns 2 and 3 releases the more retained substance which is collected in the extract (E; also herein referred to as the eluate or product in affinity or discontinuous mode). Thus, the apparent movement of columns is countercurrent to the direction of flow.

For large scale industrial systems, the bed volume is so great compared to void volumes of liquid between beds that even elaborate valving systems involving extensive conduit do not interfere with the process. As SMB is scaled down in size, void volumes become significant relative to bed volume, and at the level where total bed volume may be only a few milliliters, void volumes are crucial. The present invention addresses the challenge of devising a valving system in which a high density of individual valves can be compressed into a very small area.

Figure 3:
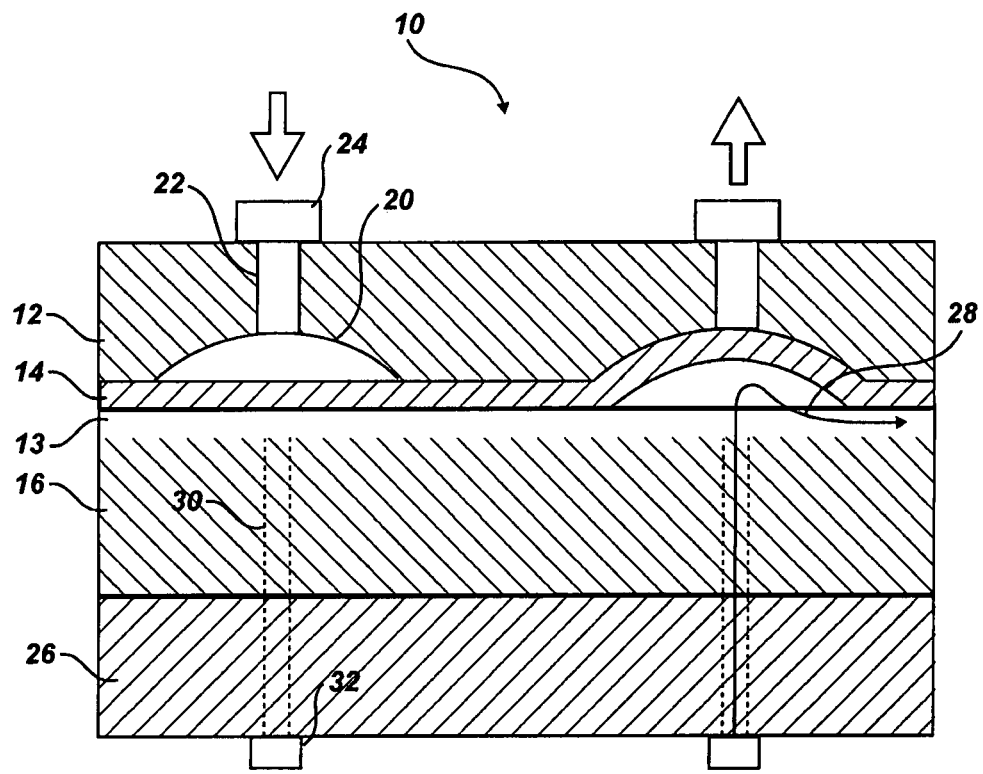
FIG. 3 is a cross-sectional view of a valve block utilizing a diaphragm under pneumatic pressure control.

FIG. 3 shows such a pair of valves in cross-section. A valve block generally 10 comprises an upper plate 12 having a connector 24 and a vertical bore 22 terminating in a recess 20. A fluid transfer plate 16 has a common groove 13 and an offset bore 30 (the offset represented by dotted lines) which communicates with an access port 32. At the bottom of the valve assembly is an anchor plate 26. Sandwiched between the upper plate 12 and the fluid transfer plate 16 is a pliant diaphragm 14, preferably composed of flexible pressure responsive material such as FEP or PFA fluoropolymer. In operation, when pneumatic or hydraulic pressure is applied the diaphragm 14 is pressed down over the vertical offset bore 30 and common groove 13 spanned by the recess, effectively sealing the gap between the offset bore and the common groove and preventing flow from the access port 32 below. The left valve in the diagram is shown in closed position. In this schematic the closed position of the diaphragm is meant to indicate that it is pressed against the upper surface of the fluid transfer plate to seal the common groove and offset bore. When the pneumatic pressure is vented, fluid pressure in the system causes the diaphragm 14 to deflect upwards into the recess 20 forming a communicating bridge between the orifice of the offset bore 30 and the common groove 13, which allows the fluid stream 28 to flow from the access port 32 through the offset bore into the common groove. A similar valve design, differing from the valve of the present invention in that movement of the diaphragm was controlled by alternating pressure and vacuum, was used commercially in synthesizer instruments manufactured in Germany during the late 1980's. Subsequently, U.S. Pat. No. 5,203,368 issued and discloses a virtually identical device.

Figure 4A:
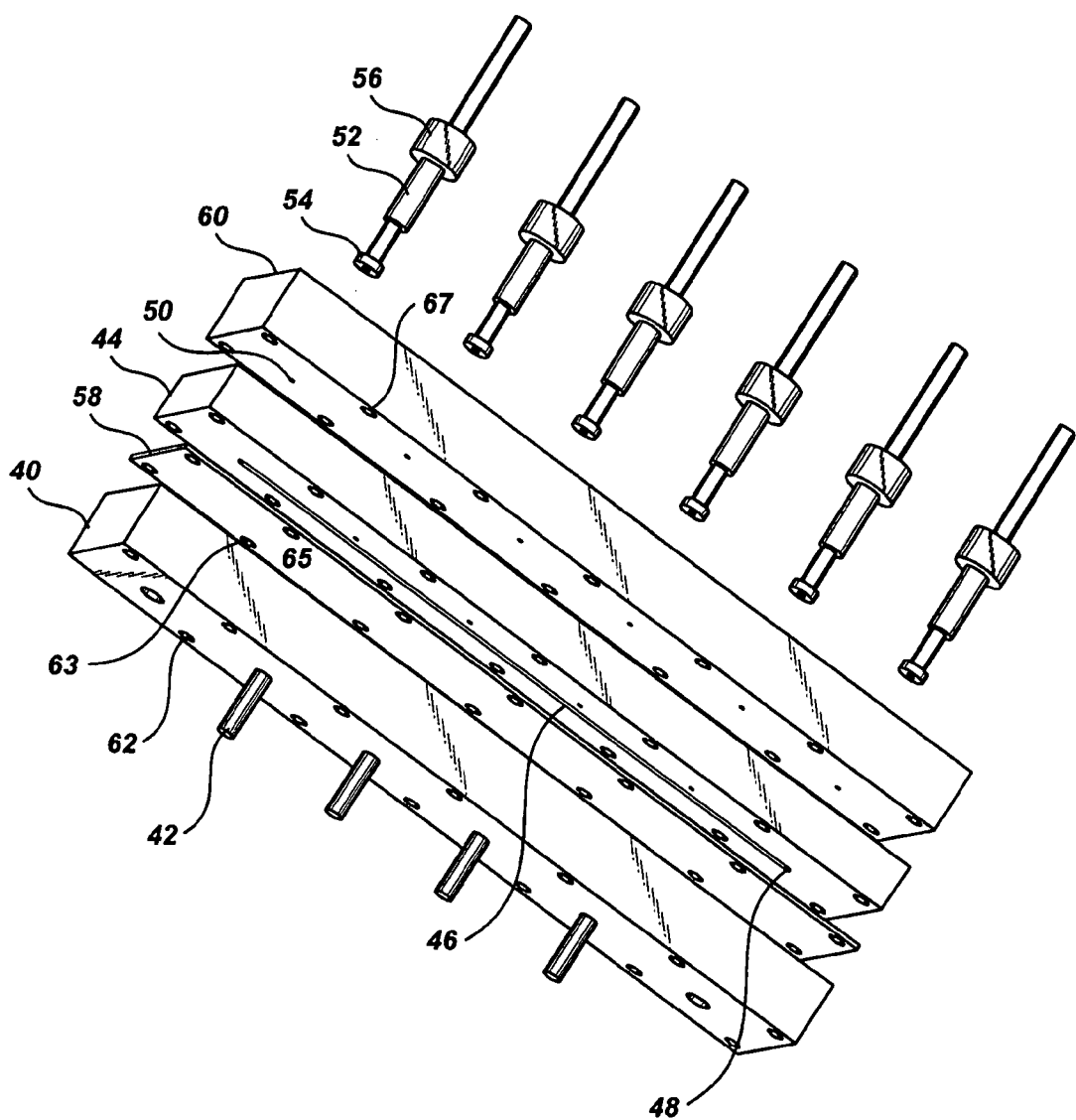
FIGS. 4A and 4B are downward and upward facing exploded perspective views showing the parts and features of a basic valve block.
Figure 4B:
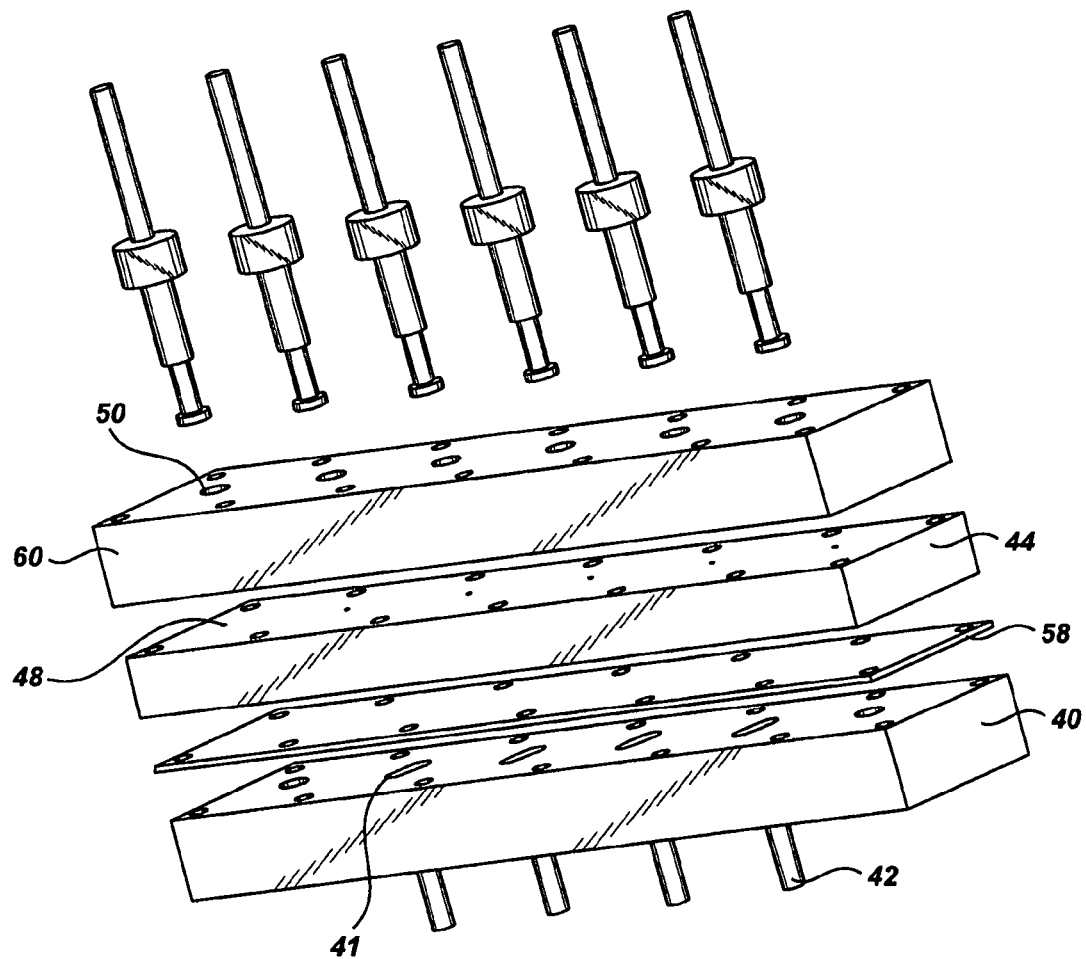

The foregoing valve strategy can be adapted to more a complex application capable of chromatographic separations. FIGS. 4A and 4B illustrate a valve block having column communicating bores and four valve sites. FIG. 4A is an exploded view showing the spatial orientation of the parts. FIG. 4B is an exploded view from the opposite perpective. The upper plate 40 has nipples 42 fastened thereto, providing access to pneumatic pressure through a bore terminating in a recess 41 (See FIG. 4B) on its lower surface. A fluid transfer plate 44 is situated below the upper plate 40 with a diaphragm 58 sandwiched between it and the fluid transfer plate 44. There is a linear common groove 46 etched on the upper surface of the fluid transfer plate 44, terminating in vertical bores 48 passing though the fluid transfer plate 44 (as shown in FIG. 4B). In addition there are four vertical liquid transfer bores arranged along the common groove 46 in liquid communicating proximity to the common groove 46. The term "liquid communicating proximity" herein means that the distance from a fluid transfer bore to the common groove is close enough that when pneumatic pressure is released the internal fluid pressure is sufficient to deflect the diaphragm upward into recess cavity thereby opening a liquid path between the bore and the common channel, but far enough apart to seal off such path when pneumatic pressure is applied. The base of the device is an anchor plate 60 having six bores (the two terminal bores at the ends of the common groove, and the four liquid transfer bores in alignment with the corresponding bores of the fluid transfer plate 44. Liquid inlet/outlet connectors 56 are selected from conventional fittings. The ones represented in the figures are compression type fittings having a stem 52 and a plunger flat head tip 54 designed to engage a seating surface within each bore to form an access port. FIGS. 4A and 4B also show a series of aligned peripheral bores 62, 63, 65, and 67. Bolts having threaded ends are inserted in the threaded aligned bores to secure the layers in sealing engagement.

Figure 5:
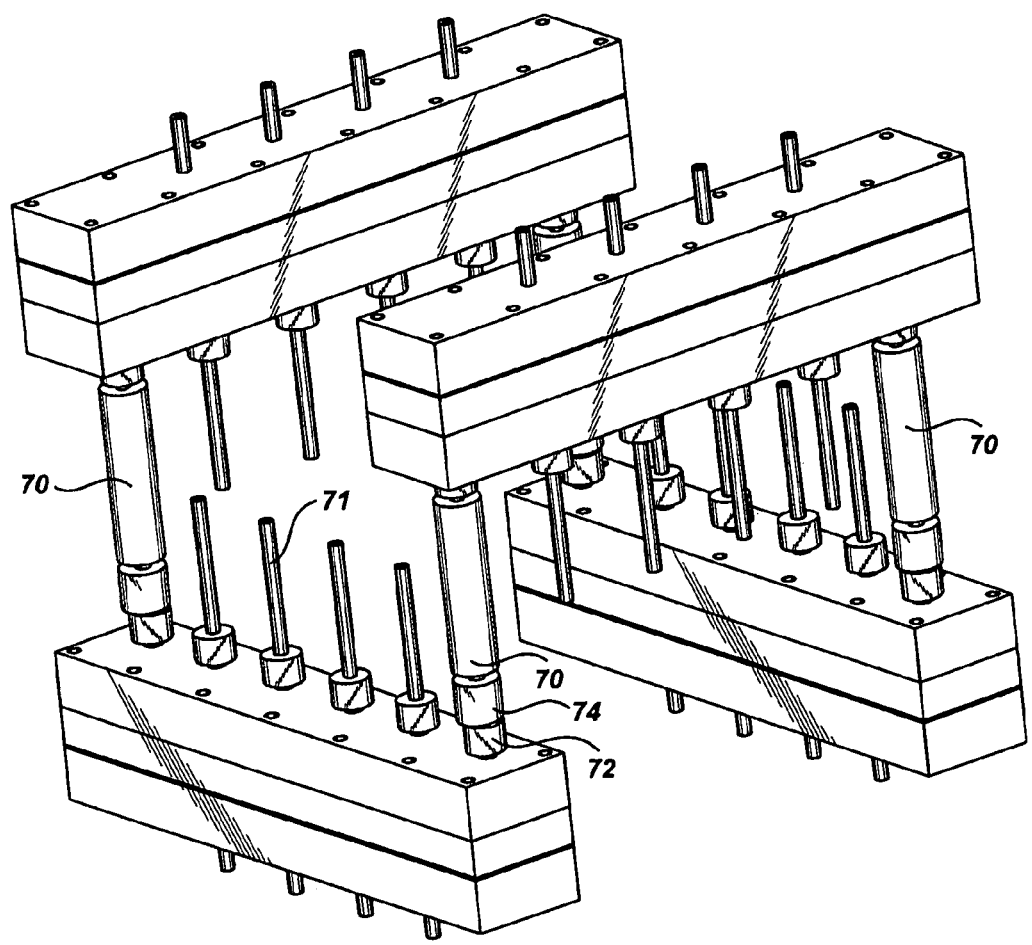
FIG. 5 is a perspective view of a four valve block assembly.

Minimally four valve blocks of the type described hereinabove may be arranged in a grouping as shown in FIG. 5 to construct an SMB device. Each of the valve blocks is interconnected to two others through columns 70 mounted therebetween to form a continuous circular loop through the system. Columns are arranged head-to-tail such that the outlet of one column is connected to one end of a valve block and the inlet of the next column is connected to the other end of the valve block. Each of the liquid transfer ports 71 in each valve block is assigned F, R, D, and E inputs and outputs. In operation, at any given time one valve is open in each block, and the other three are closed. At the end of a predetermined switching interval, the open valve closes and another valve opens in the desired sequence. Flow may be controlled by use of conventional pumps for the inlet and outlet streams. In a preferred embodiment, check-valves 74 can be inserted at either the inlet or outlet side of one or more columns to prevent bidirectional flow of input liquids. These may conveniently be placed inline of the column connectors 72, which constitute conventional fittings.

Figure 6:
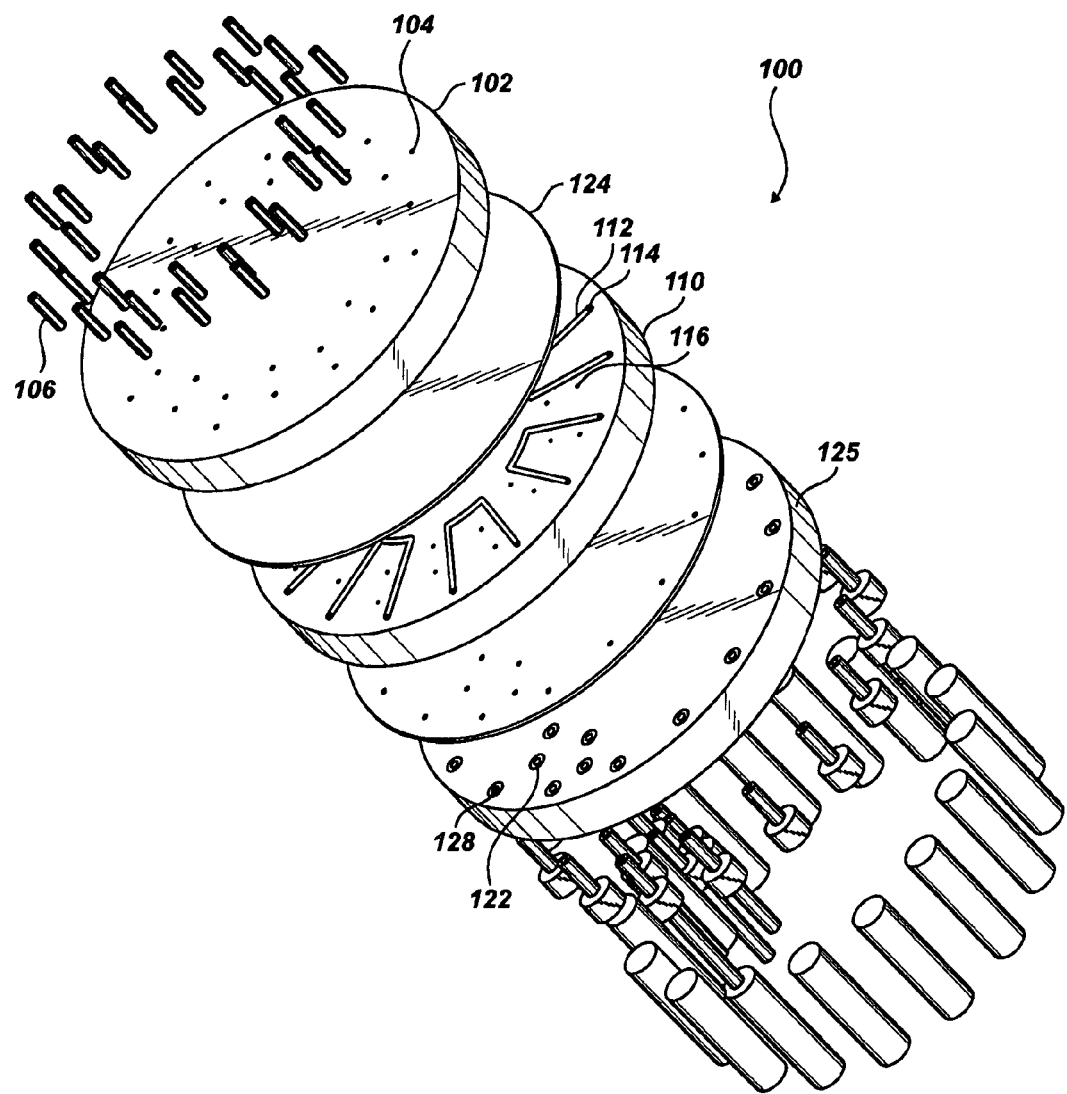
FIG. 6 is a downward facing exploded perspective view of a sixteen column annular valve module.
Figure 7:
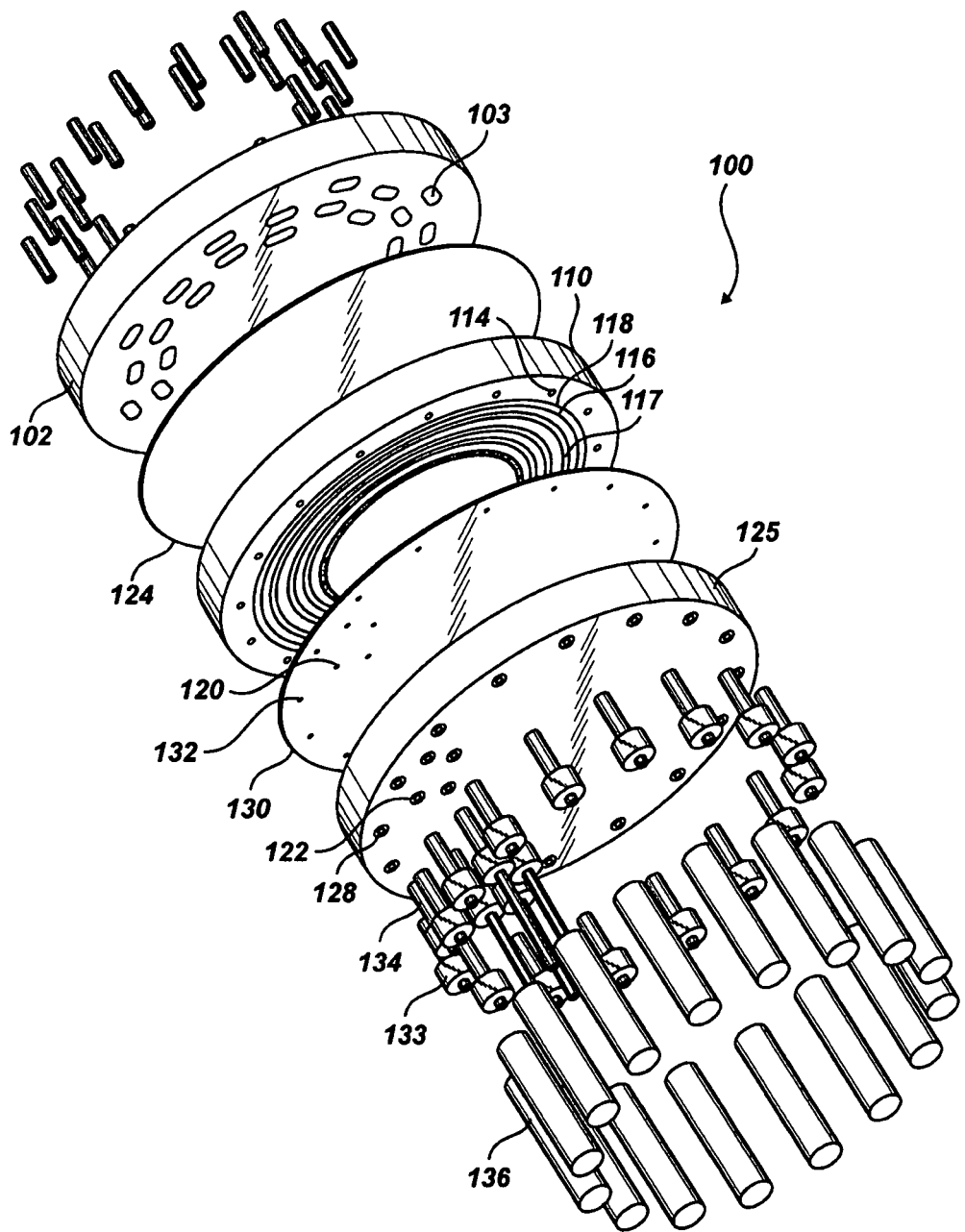
FIG. 7 is a upward facing exploded view of a sixteen column annular valve module.

A more complex standard SMB device is depicted in FIGS. 6 and 7. This device is shown in a sixteen column configuration, but the number of columns may be any number four or greater. Commercial SMB devices are typically offered in column capacities from four columns to thirty two. An annular configuration is chosen to minimize void volume in the system. An annular valve block module, generally 100, comprises several layers of machined components firmly compressed together to form a cylindrical body. The layers are illustrated in FIGS. 6 and 7 in upward and downward facing exploded perspective views.

The uppermost layer is an upper plate 102 having 32 or more annularly arranged bores 104 (FIG. 6) in two or more concentric configurations, extending from the upper surface of the plate and terminating in a recess on the bottom surface 103 (FIG. 7). Press fit nipples 106 attached to the bores 104 provide a coupling appendage for connecting a source of pneumatic pressure. A fluid transfer plate 110 is situated below the upper plate 102. There are a series of eight U-shaped grooves 112 etched onto the upper surface of the fluid transfer plate 110 and arranged annularly facing the outer perimeter of the plate. These grooves terminate in column communicating vertical bores 114 at each end, which extend from the upper surface to the lower surface (114, FIG. 7). A group of four or more concentric ingress and egress channels 116 (FIG. 7) are etched into the lower surface of the fluid transfer plate 110. Arranged spacedly along the U-shaped grooves in liquid communicating proximity are four or more liquid access ports 116 extending from the upper surface to the lower surface of the fluid transfer plate, the ports being aligned to communicate individually with each of the concentric channels.

The U-shaped grooves 112 may have square or rounded walls, and may be arranged in other geometries such as Vs or semi-circles. In the miniature SMB devices the grooves and concentric channels may be 1 mm or less in size.

A valve diaphragm 124 is disposed between the upper plate 102 and the fluid transfer plate 110, to form a sealing surface between the lower surface of the upper plate and the upper surface of the fluid transfer plate. The diaphragm is composed of a pliant pressure responsive material. Elastomeric Teflon such as PFA and other fluoropolymer membranes responsive to less than 20 psi of pressure differential are suitable in this application.

An anchor plate 125 is positioned below the fluid transfer plate 110 and has bores extending from the surface of the plate to the lower surface thereof. The column access ports 128 are arranged in a circle and correspond to and are aligned with the corresponding bores 114 at the ends of the U-shaped grooves 112 in the fluid transfer plate 110. Four inlet and outlet bores 122 extending through the body of the anchor plate 125 are positioned to communicate with each of the four concentric channels 116. The concentric ingress and egress channels are assigned to each of F and D reservoirs, and R and E receptacles in no particular order. Thus, there is common input and output source for all the valves that feed from and to each column position. Optionally, there also vent ports located in each channel immediately opposite the feed bores 122, to allow escape of air from the channels during filling. Optionally, there may be a barrier membrane or plate 130 disposed between the anchor plate 125 and the fluid transfer plate 110 to provide inlet/outlet bores 120 and column communicating bores 132 to the anchor plate 125. In this configuration the barrier membrane or plate becomes the lower wall of the concentric channels 117.

The anchor plate is fitted with couplings accommodating each column communicating and inlet/outlet port, as described above for the valve block assembly. FIGS. 6 and 7 show the compression type fittings 133 having a stem 134. Such fittings provide a good liquid seal without altering the internal diameter of port and connector. Several types and brands of such fittings are conventionally available. The figures also show the relative position of the columns 136.

Figure 8:
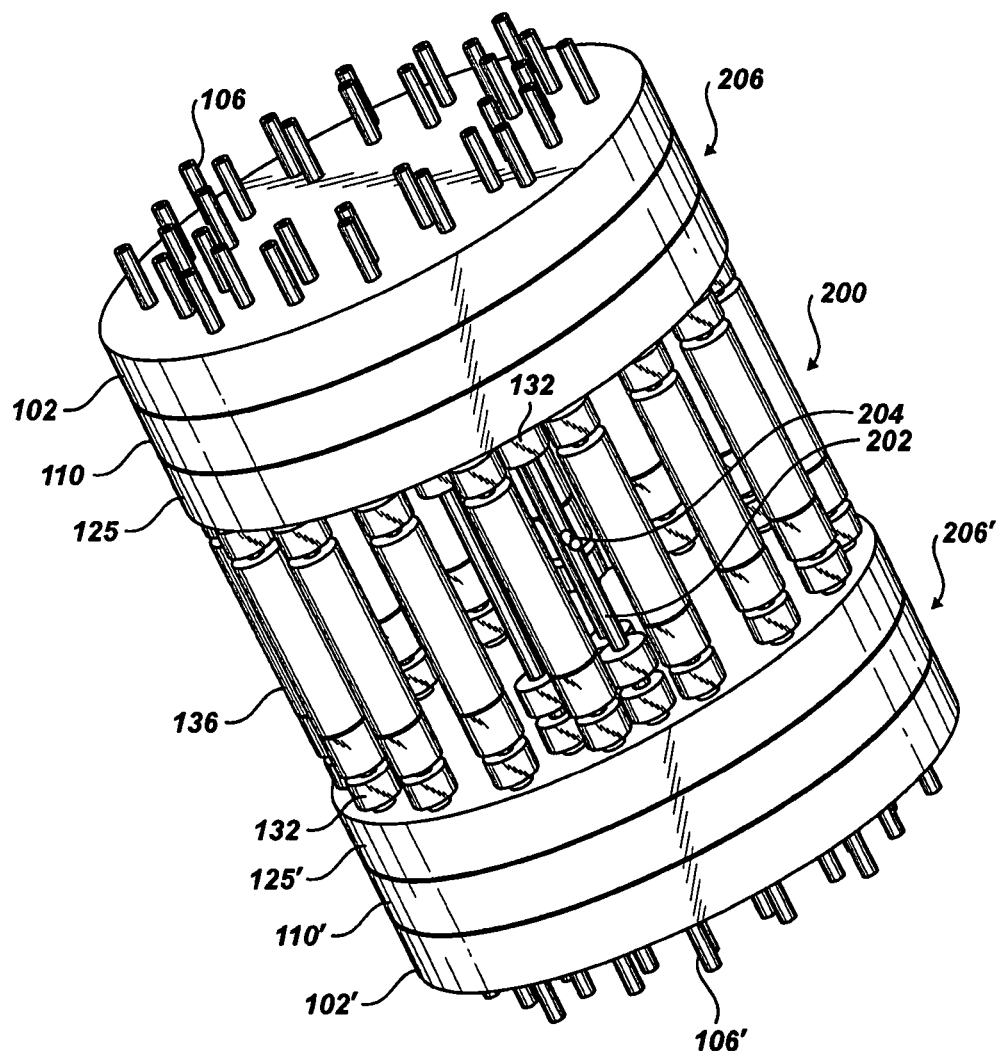
FIG. 8 depicts in perspective view a completely assembled sixteen column SMB device showing the disposition of columns in relation to two valve modules.

Referring to FIG. 8, a full SMB fluidic system according to the present invention, generally designated 200, comprises two annular valve block modules 206 and 206' respectively aligned in inverted orientation. The modules are interconnected by a plurality of chromatographic columns 136 attached at either end to a module by column connector means 132 mounted on the column communicating bores. The columns are attached in alternating orientation, with inlets of every other column attached to one valve block module and the inlets of the other columns attached to the other valve block module. Also, inline of the columns are check valves to ensure unidirectional flow of liquid in the system. The upper plate 102, fluid transfer plate 110, and anchor plate 125 of the top module are shown in reverse order in the inverted bottom module as 125', 110', and 102'. Vertical inlet/outlet conduits 202 connect each access port (122, FIG. 7) pair of the upper and lower modules through connectors 132 on each end. Each vertical feed conduit 202 is provided with a T stem 204 connected to an input reservoir or an output receptacle. Normally, liquid is delivered to or from the system via the vertical feed conduits under pressure using in line pumps. F, D, and E are typically on flow rate control, i.e. pumps, It is possible to have R on flow control as well. A suitable pump for this application includes a piston type chromatography pump, preferably using a downstream backpressure regulator and optionally a pulse dampener to minimize flow pulsing.

Figure 8B:
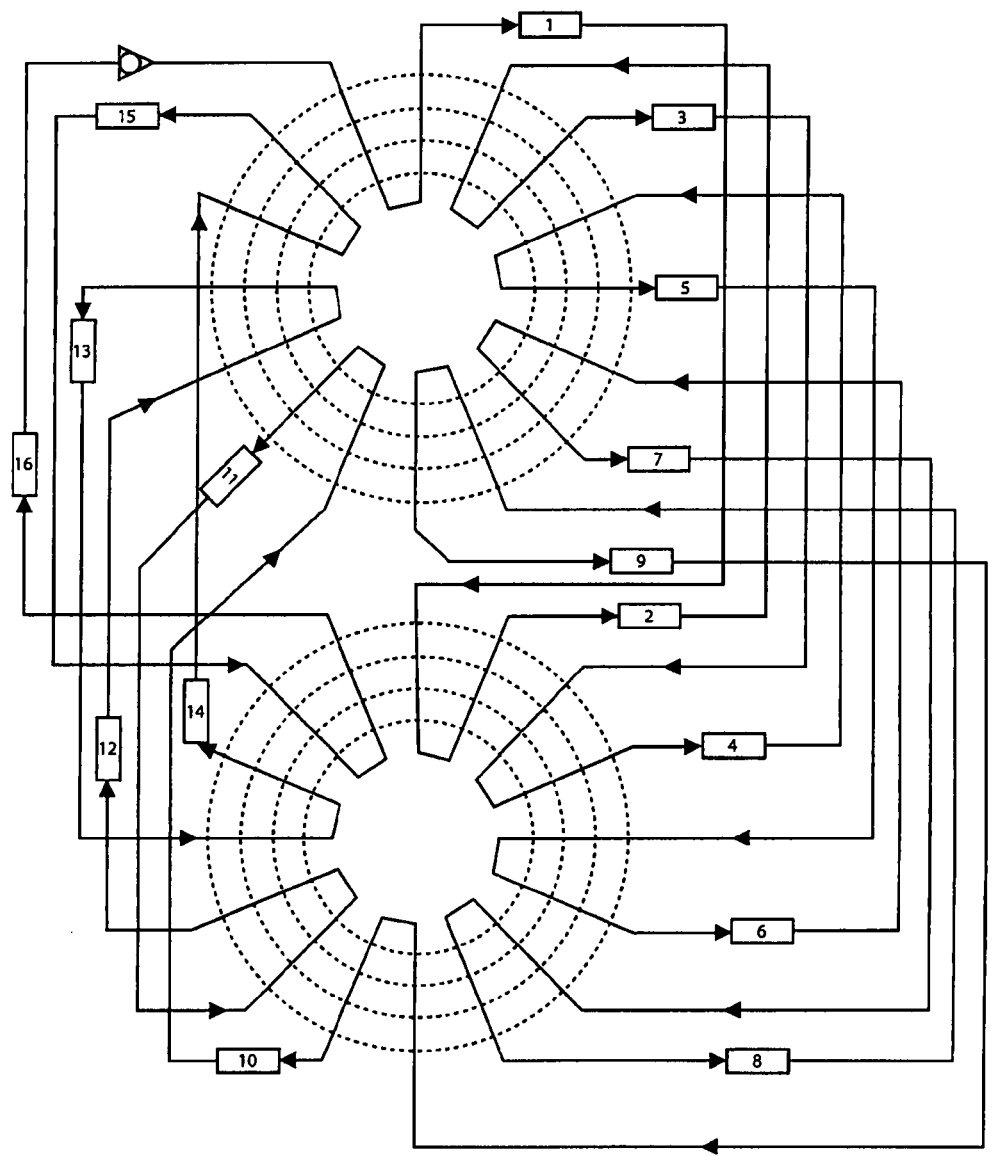
Figure 9:
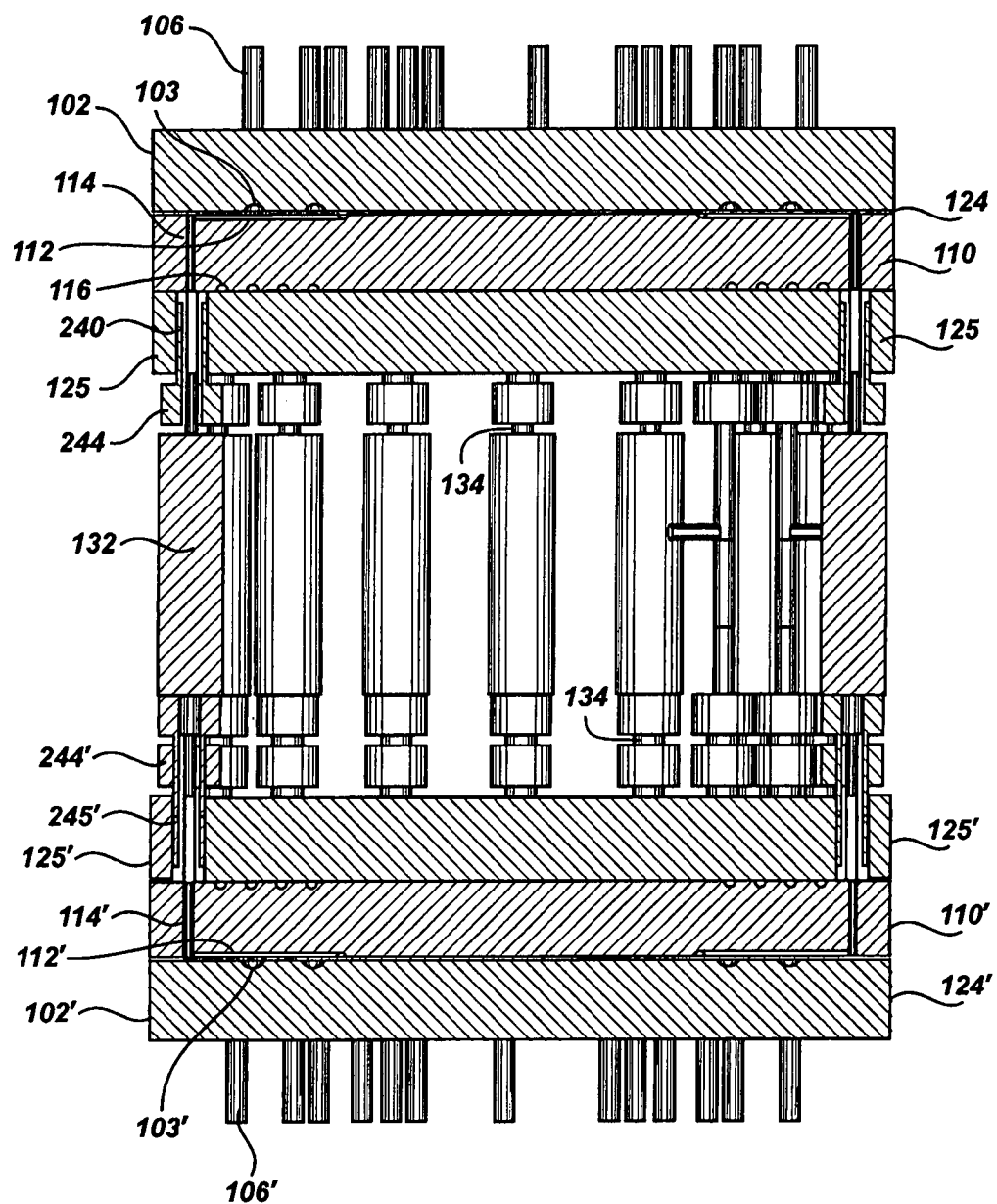
FIG. 9 is a cross-sectional view of a completely assembled sixteen column SMB device.

FIG. 9 depicts the SMB fluidic system shown in FIG. 8 in cross sectional view. The upper plate 102 has recesses 103 shown partially at a foreground section. The diaphragm 124 is sandwiched between the upper plate 102 and a fluid transfer plate 110. A portion of the U-shaped groove 112 is shown in closed position, and terminates in a column communicating bore 114 which extends in alignment through the anchor plate 125, a column connector 244 and into the column 132. Symmetrical configuration is presented left and right, and invertibly for the lower module. Unidirectional flow ensures a continuous loop in which physical top to bottom flow in one column becomes bottom to top in the next column. Inputs and outputs to the loop are not shown because these structures are not in the cross sectional plane. The flow pattern between modules is illustrated in FIG. 8B for a sixteen column device. The dotted lines indicate the concentric channels located on the lower surface of the fluid transfer plate. A valve is positioned at each point where the dotted lines intersect a flow on the U-shaped groove.

The upper plate and anchor plate may be machined from aluminum, stainless steel, or a variety of plastics. Aluminum alloy 6061-T6 is particularly suitable for this application. Contact surfaces, namely, the lower surface of the upper plate, the upper and lower surfaces of the fluid transfer plate, and the upper surface of the anchor plate should preferably be polished to a #4 microinch RMS surface roughness, in order to seal properly. The fluid transfer plates may be machined from a selection of hard plastics. PEEK or PCTFE are preferred. Diaphragms and membranes can be fabricated from 5-10 mil sheets of fluorocarbon polymers, polypropylene. Fittings are all conventionally available in PEEK, PTFE, ETFE, PCTFE, and other plastics. All of the above materials are resistant to corrosives and solvents, durable, and rigid, except for the pliant, pressure responsive membranes and diaphragms. The anchor plate can be manufactured for thickness and physical strength and serves as a rigid base plate allowing the other layers to be made as thin as possible to reduce void volume ever further.

An important aspect of the present invention is adaptation of the principles of affinity chromatography to SMB. In standard chromatography, the basis of separation is differential elution of species as a function of some generalized physical or chemical property. For example, in size exclusion chromatography separation is on the basis of molecular size and shape. In ion exchange chromatography separation is based on charge. In standard chromatography based on general chemical properties, separation of the desired species from complex feed mixtures is not highly discriminating. All proteins of a particular molecular size or charge will elute under similar conditions, thus reducing purity. This explains why high purification to greater than 90% homogeneity often involves multiple purification steps customized for each target protein.

In affinity chromatography, the target molecule contains a chemical moiety which specifically interacts with a second moiety immobilized on a column substrate. Recombinant proteins can be engineered to contain specific peptide or other chemical moiety which act as affinity tags that bind specifically to immobilized ligands. If the affinity tag is something either not naturally occurring or not likely to be present on proteins in the cellular contents in which the target protein is expressed, a high level of purity can be obtained using a relatively standardized protocol. This has significant implications in structural proteomics, where the challenge is to purify large numbers of proteins at multi-milligram scale for x-ray crystallographic or NMR spectroscopic analysis.

A number of such affinity chromatography systems have been described which can be readily adapted to an SMB purification stratagem. U.S. Pat. Nos. 5,310,663, 5,284,933, and 4,569,794 disclose a hexahistidyl tag having specific affinity for a resin incorporating a metal chelate. A fusion protein of interest having the six histidine tag preferentially binds to a $Ni^{++}$ chelate on the solid phase. The binding affinity for enzyme and substrate is exploited when a fusion protein of glutathione-S-transferase recognizes and selectively binds to a glutathione-conjugated resin, as described in U.S. Pat. No. 5,654,176 and Smith, et. al, Gene 67: 31 (1988). Other examples of affinity systems include a peptide fusion system [Raines, et. al, Methods Enzymol., 326: 362 (2000)], cellulose binding domain fusion proteins (U.S. Pat. Nos. 5,719, 044 and 5,202,247), mutant streptavidin binding peptide (U.S. Pat. No. 5,506,121), and calmodulin binding protein fragment [FEBS Lett. 302: 274 (1992)]. The advantages of SMB in these affinity systems are three fold: (1) the ability of SMB of sufficient column number to fine tune collection of a high purity target fraction, (2) the inherent capability to process cell extracts continuously, and (3) the capability of SMB to more efficiently utilize the solid phase. These advantages are especially significant when purifying target from cell extracts of insect cultures where expression levels often are below 1% of total cellular protein.

Figure 10:
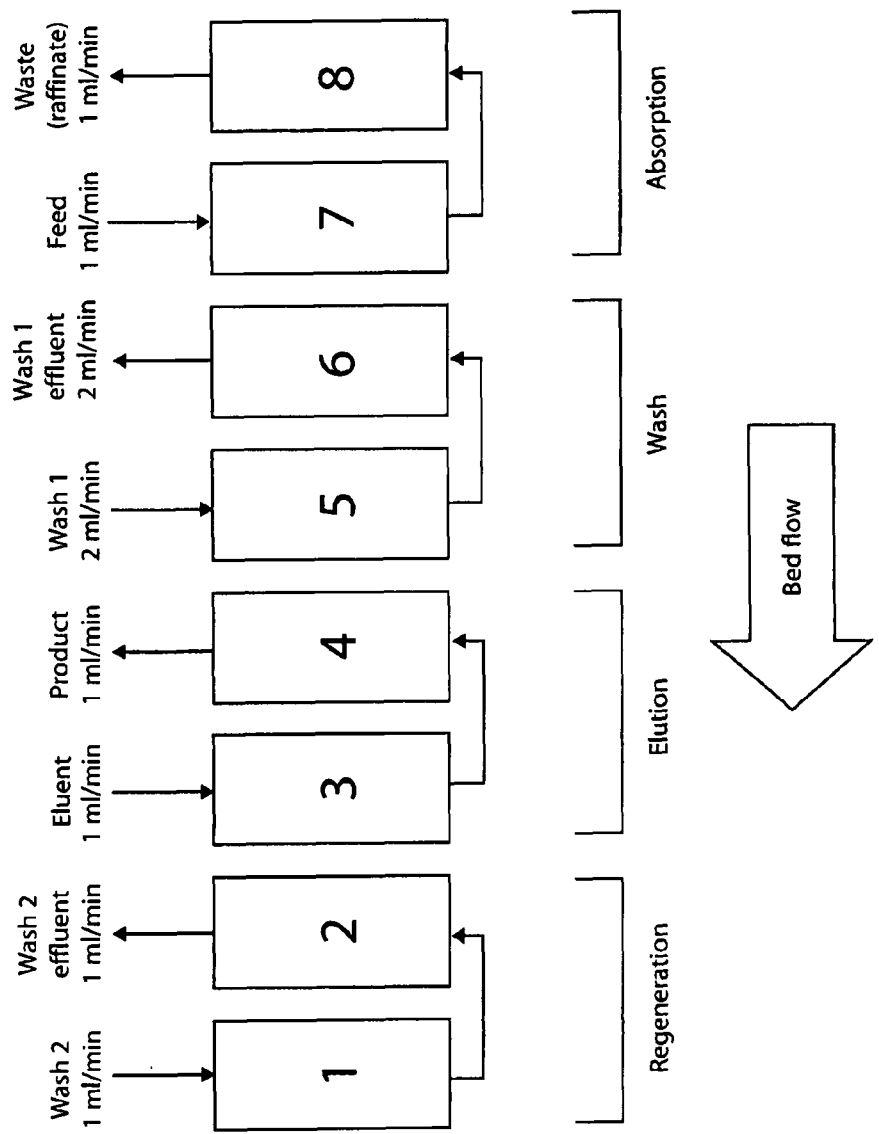
FIG. 10 is a diagram of an eight column SMB system showing four closed loops for preventing wash 1 solution from entering the absorption zone, desorbent (eluent) from entering the wash zone, wash 2 solution from entering the elution zone, and feed from entering the regeneration zone.
Figure 11:
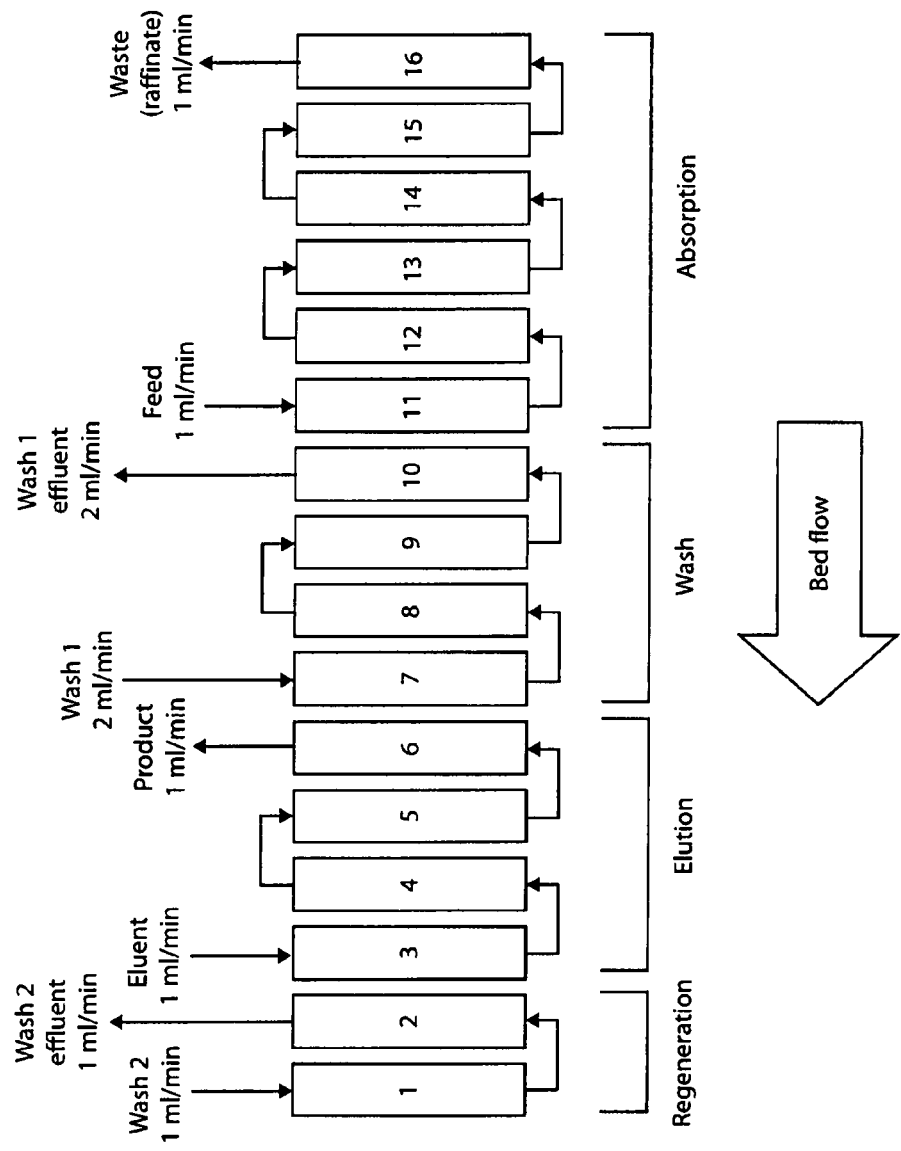
FIG. 11 is a diagram similar to FIG. 10 for a sixteen column SMB device.

The requirements for affinity SMB are different operationally because of the necessity of isolating portions of the otherwise continuous loop in standard SMB, if the system is to mimic standard batch type affinity chromatography. FIG. 10 is a schematic of one embodiment of affinity SMB for an eight column system. Four chromatographic zones are depicted, regeneration, elution, wash, and adsorption. The regeneration zone comprises the column 1 and 2 positions, elution takes place in the column 3 and 4 positions, the wash occurs in the column 5 and 6 positions, and adsorption occurs in the column 7 and 8 positions. The term "column positions" rather than columns per se is used because the actual columns participating in each functional step keeps rotating as for standard SMB. Thus, after a predetermined interval, column 7 occupies the functional position of column 6 as depicted, and so on. Like standard fluid SMB, flow, as indicated by the arrows, is generally left-to-right in contrast to the columns which appear to be moving in a right-to-left direction. The size of the system can encompass fewer or greater numbers of columns, depending on how many columns are assigned to each chromatographic zone. For example, FIG. 11 is a schematic drawing showing sixteen columns, and assigning four columns for the elution zone, four columns for the wash zone, six columns for the adsorption zone, and two columns for the regeneration zone. With sufficient column number encompassing several within a given zone, more than one wash/desorbent can be introduced into and exit a flow isolated zone.

In operation, according to FIG. 10, feedstock containing the species to be separated is loaded onto column 7, where it is statically adsorbed to the affinity matrix of the column. Adsorption continues into column 8. Unbound species are largely eliminated from the system in the raffinate exit port at column 8. Column 7 then "rotates" by valve switching into column 6 position and then the column 5 position. In this zone, extensive washing of the column takes place. Rightward directed flow carries residual unbound or weakly bound contaminants through the system and they are eliminated as Wash 1 Effluent after exiting column 6. Since this zone is a closed loop the flow rate of the Wash 1 stream can be adjusted independently of the other streams and therefore a greater volume of fluid can be flushed through the columns in a given period for more thorough removal of contaminants. In the next two valve switchings, original column 7 enters the original column 3 and 4 positions. Eluent is introduced at column 3 and exits at column 4. In affinity chromatography, even small residuals of desorbent may interfere with efficient binding at columns 7 and 8. Therefore, the eluent is also a closed fluid loop, and the desorbent is not permitted to enter the absorption zone of the system. After elution of the desired target, the original column 7 passes into a second wash zone for regeneration of the column which removes desorbent, and prepares the column for the next round of adsorption. This is also a closed fluid loop to eliminate desorbent from the system. Thus, there are four independently controlled loops in this configuration, each formaing a zone havingsd conditions to enable efficient adsorption, washing, elution of the purified target, and regeneration of the solid phase. For purposes herein the terms "eluent" and "desorbent" are deemed identical and refer to the same thing; differentiated only because they are expressed in the literature as different terms which have the same meaning.

The apparatus of the present invention for performing affinity SMB is very similar to that for standard SMB, but with two significant differences. Four new input/output streams are incorporated by adding corresponding valve ports and ingress/egress channels. These streams enable the configuration of the wash zones in which different buffers can be introduced and removed for the wash and regeneration steps. A cutoff valve is also required to prevent flow between columns for the establishment of isolated zones (closed loops). There are thus nine total valves present on each U-shaped groove, rather than the minimum of four for a standard SMB system. The additional flow streams and cutoff valves also enable additional configurations of standard SMB, such as the incorporation of internal recycling flow control, thus increasing utility for this mode as well.

Figure 12:
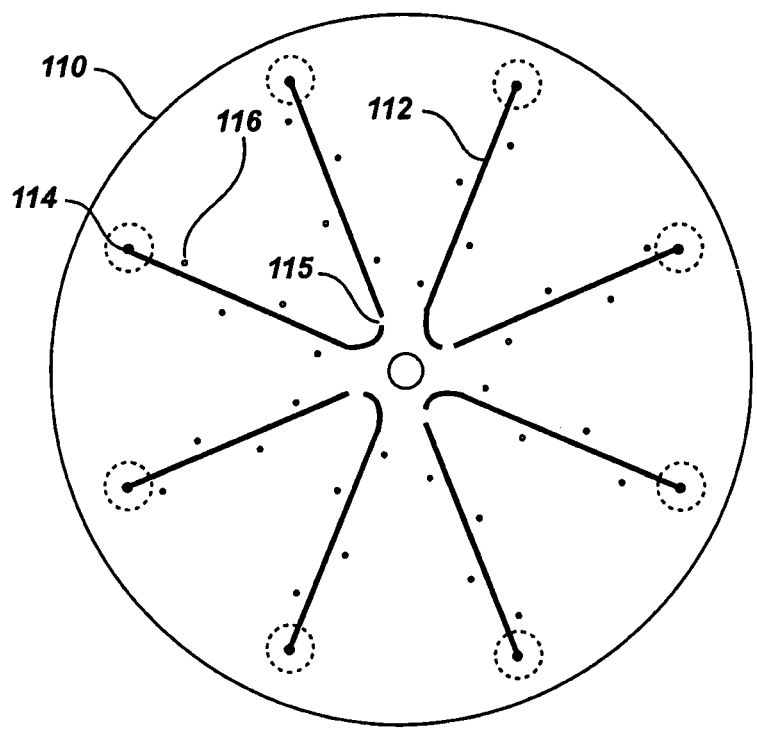
FIG. 12 is a plan view of the upper surface of a fluid transfer plate for use in an eight column SMB device.
Figure 13:
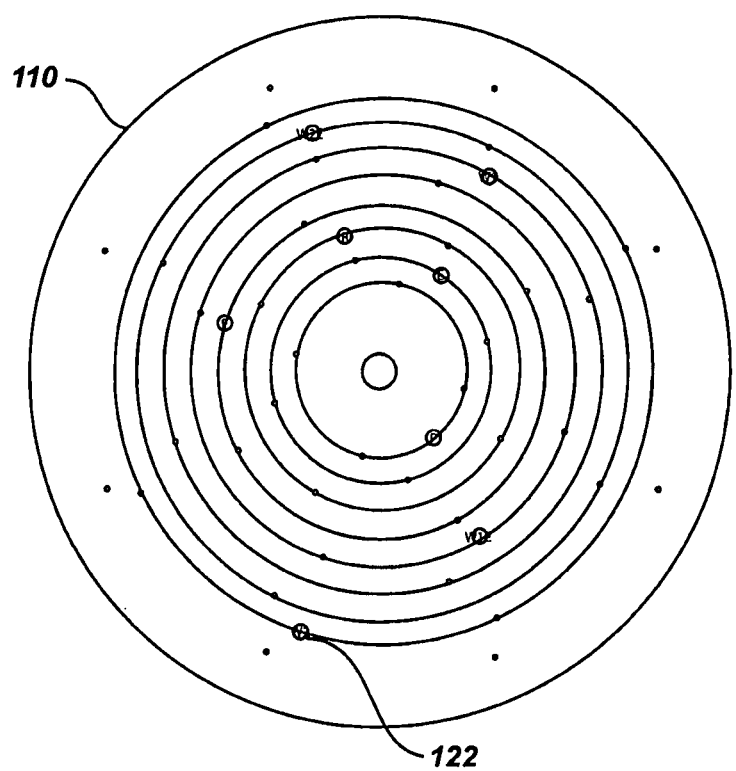
FIG. 13 is a plan view of the lower surface of a fluid transfer plate for use in an SMB device.
Figure 15:
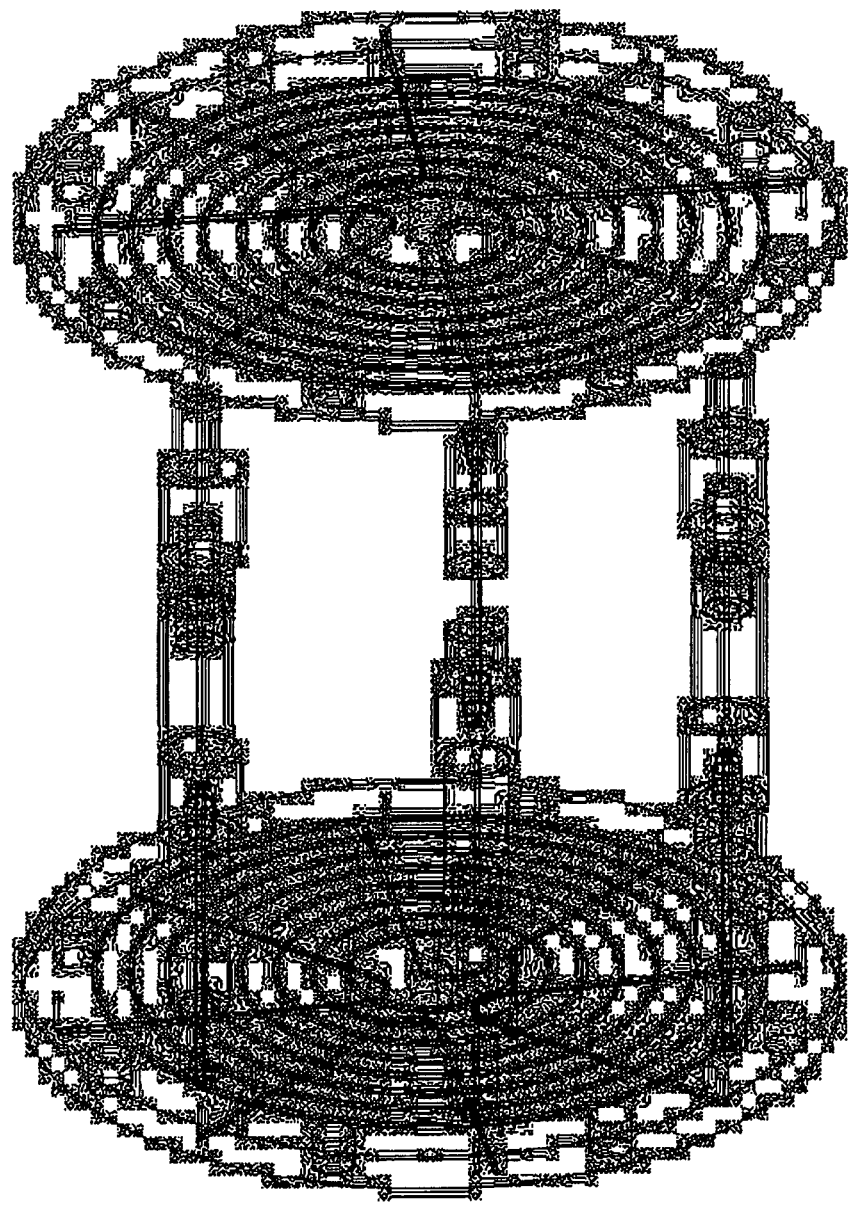
FIG. 15 is a perspective view showing the relationship of upper and lower fluid transfer plates with respect to orientation of column communicating bores at each end of a column.
Figure 16:
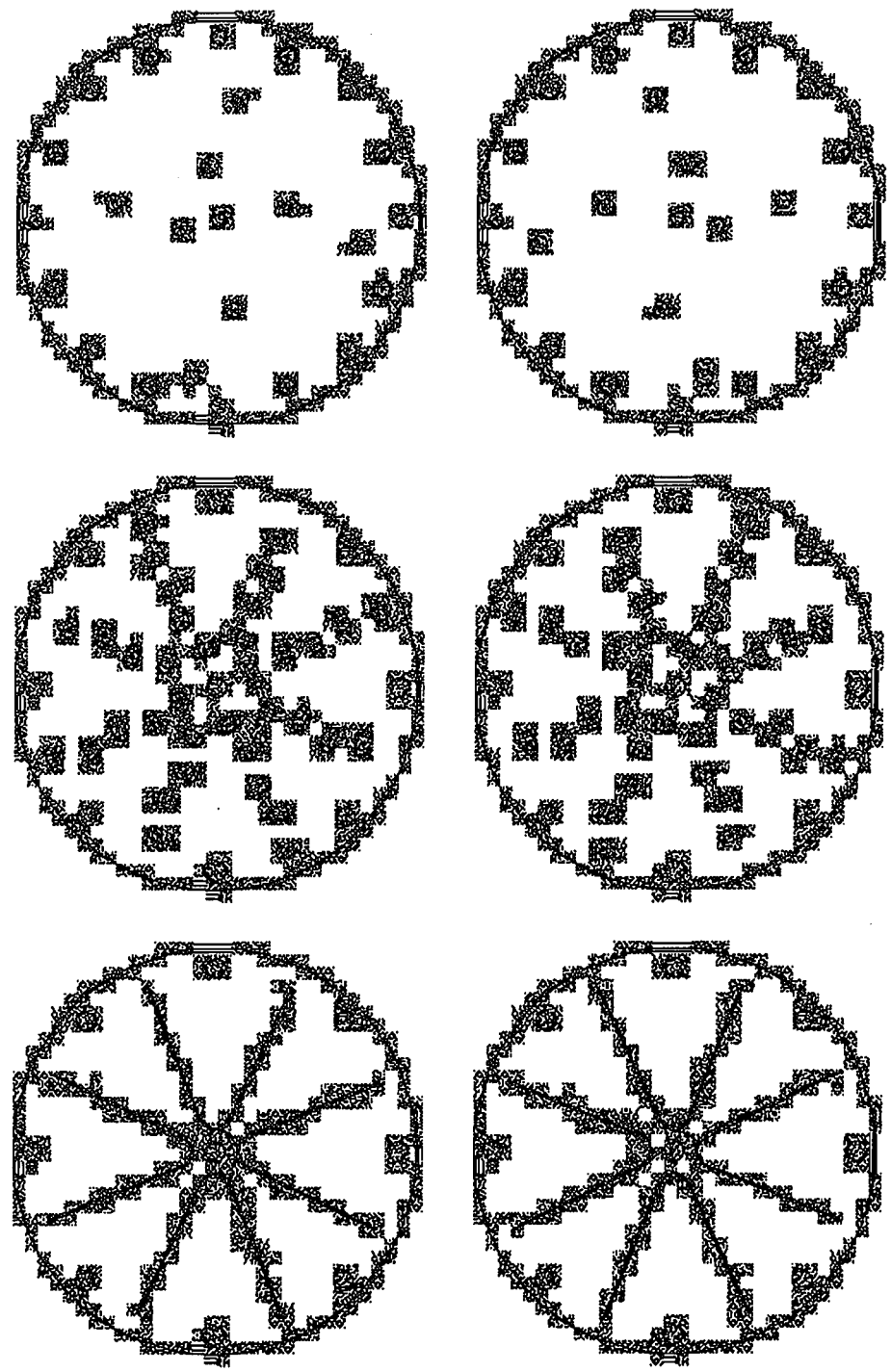
FIG. 16 is a side-by-side comparison in plan view demonstrating the asymmetry of features of the pneumatic pressure plate, fluid transfer plate, and anchor plate for upper and lower modules.
Figure 17A:
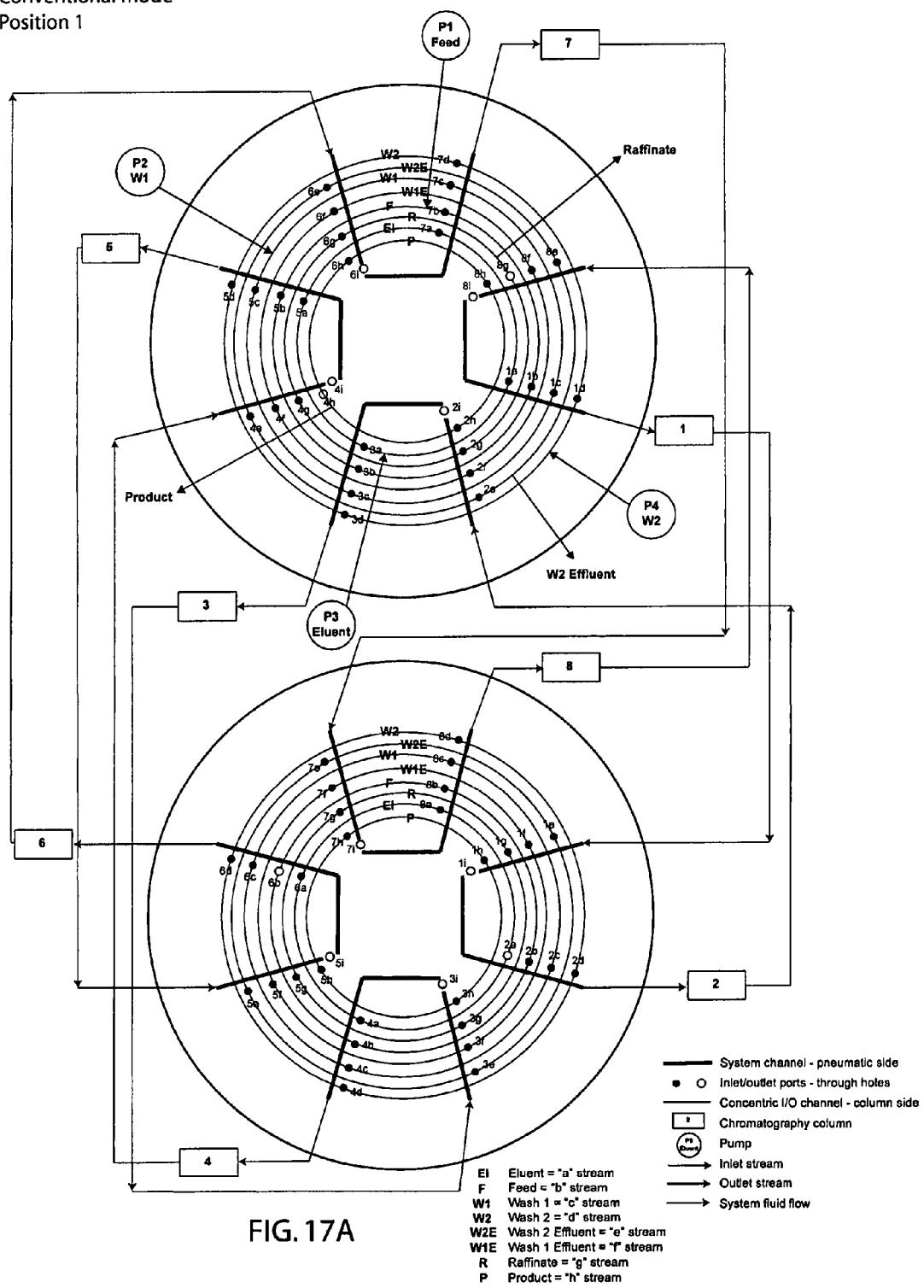
FIGS. 17A-D are schematics showing the valve configuration for the first four cycles of standard SMB as illustrated by schematic representation of the fluid transfer plates.
Figure 17B:
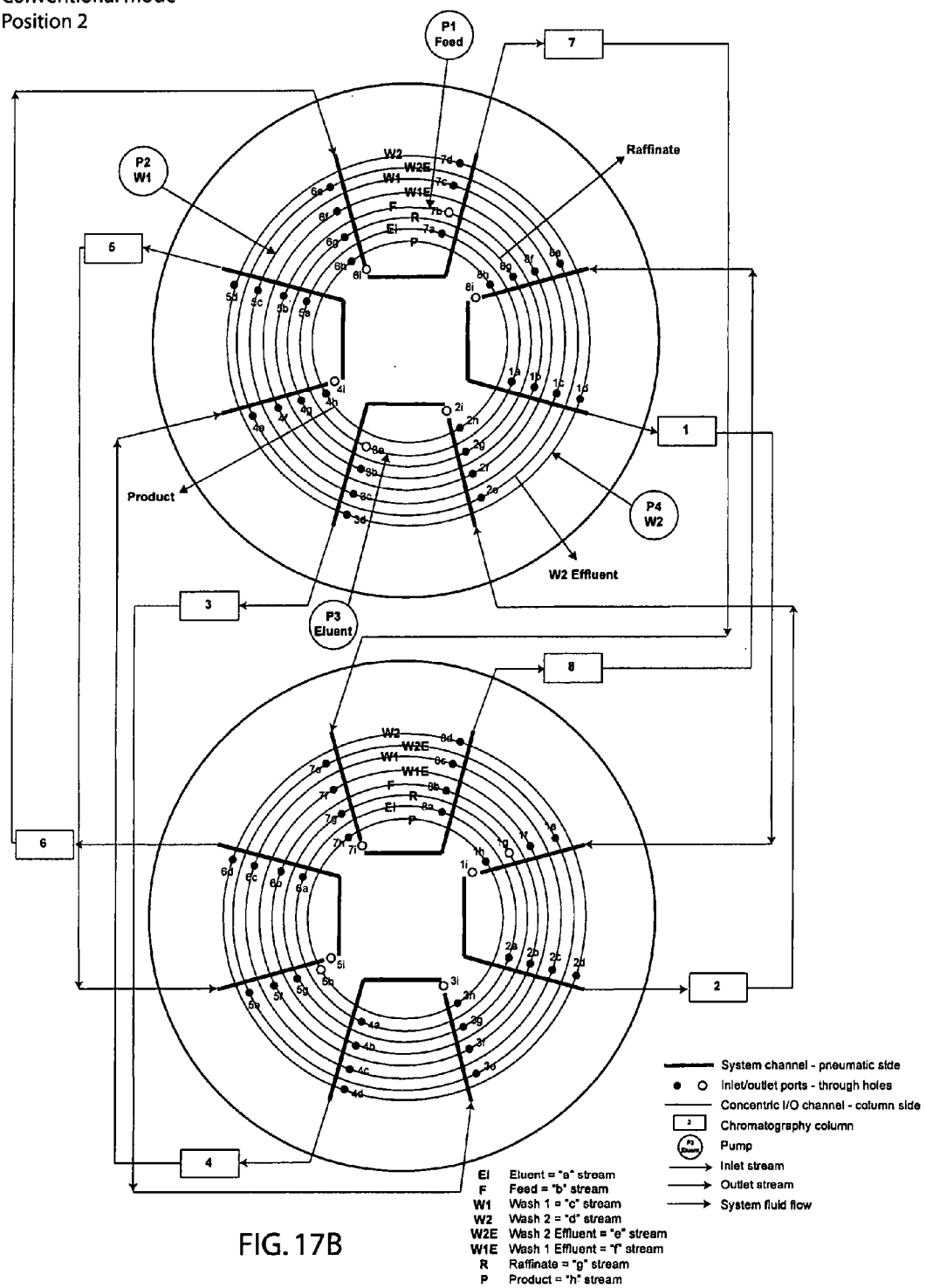
Figure 17C:
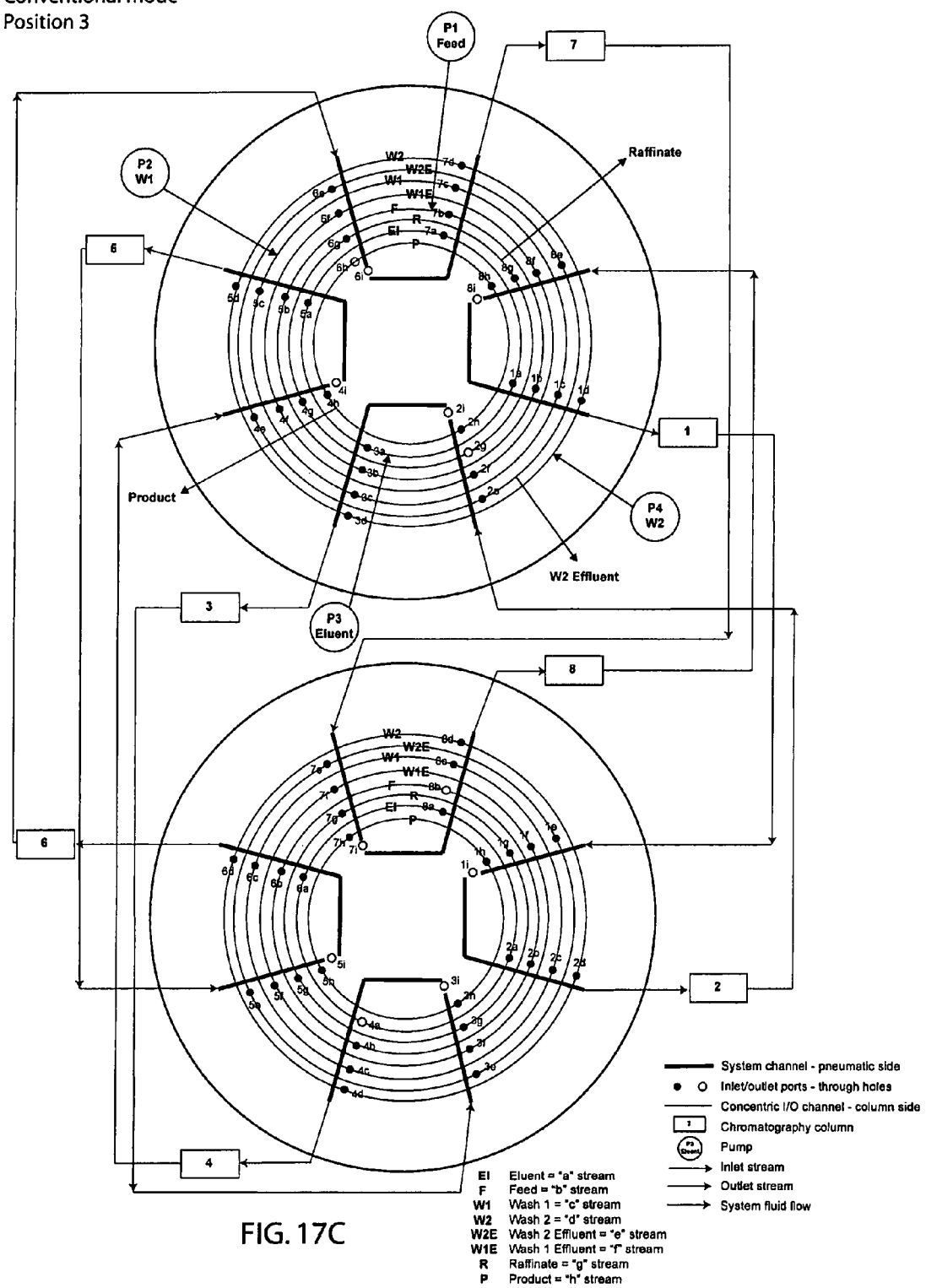
Figure 17D:
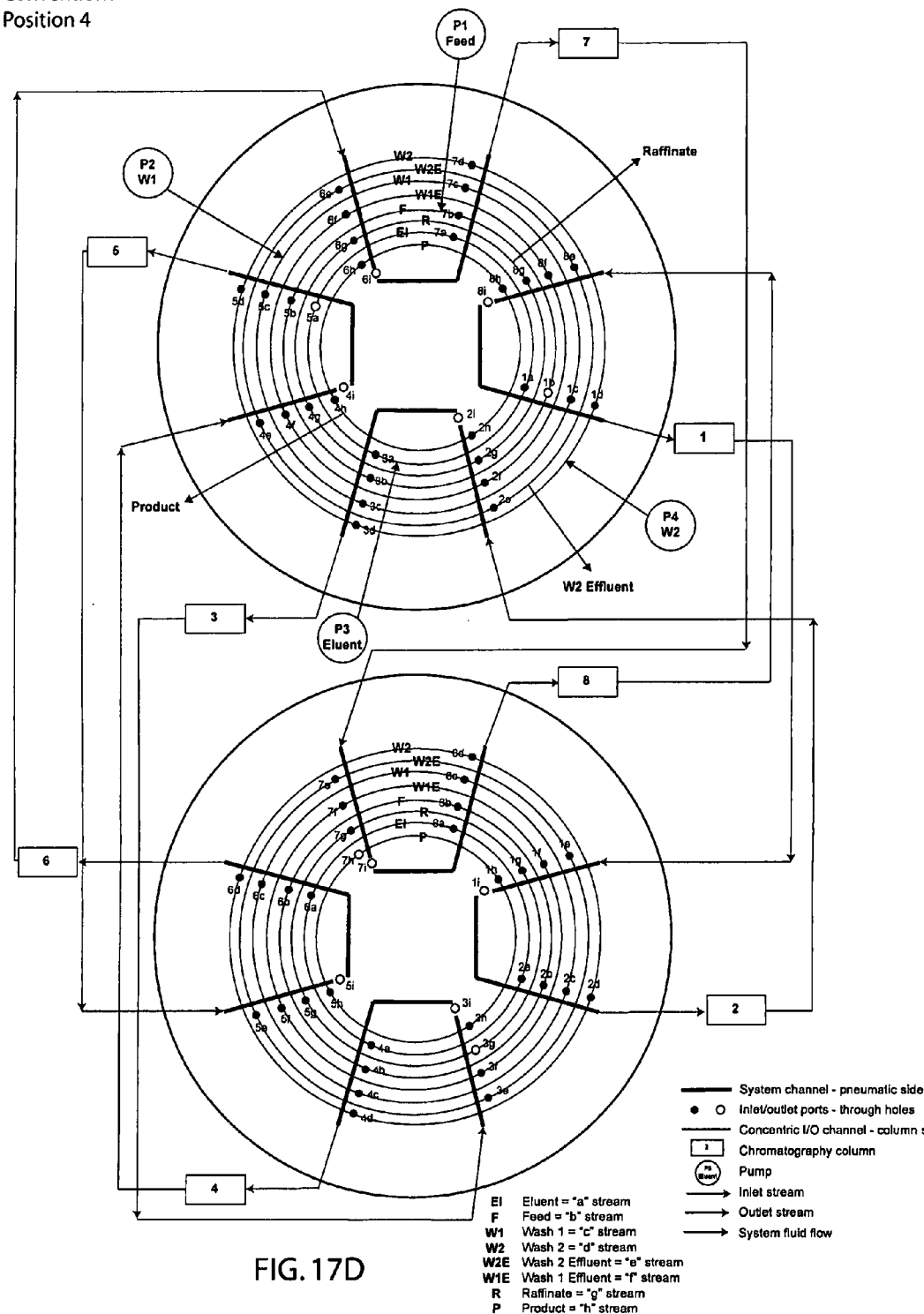

FIG. 12 is a plan view of the upper surface of a fluid transfer plate 110 for affinity or standard SMB. There are a series of four U-shaped grooves 112 arranged annularly facing the outer perimeter of the plate. Each of the grooves terminates in two column communicating bores 114, which extend from the upper surface of fluid transfer plate 110 to the lower surface thereof. Each groove also contains a gap, or interruption, for the cutoff valve 115. The much preferred position of the gap 115 is downstream of the outlet valves for the preceding column. Arranged spacedly along the U-shaped grooves in liquid communicating proximity are eight liquid access ports 116 extending from the upper surface to the lower surface of the fluid transfer plate 110. The dotted line circles shown on the figure indicate the position of the columns in the assembled valve block module. As seen in FIG. 13, the lower surface bears eight concentric channels each intersecting four of the liquid access bores 116 thereabove. Referring to FIG. 15, two facing fluid transfer plates are placed in alignment and columns are positioned therebetween in partially exploded view. Note that in the lower fluid transfer plate the orientation is reversed so that liquid passing through a column communicating bore on the upper plate on the inlet leg of the U-shaped groove is always paired with a column communicating bore on the lower plate on the outlet leg of the U-shaped groove adjacent to its cutoff valve, This has certain manufacturing implications, because it is apparent that upper and lower plates are not identical, and in fact, are mirror images. Similarly, referring to FIG. 16, the upper plates of the upper and lower modules are also mirror images, as are the upper and lower anchor plates.

Valves under pneumatic or hydraulic control operate under pressure emanating from conventional manifolds. The source of pneumatic pressure may be a common inert gas pressurized tank containing either nitrogen or helium. In the case of affinity SMB, the complexity of control is such that only an individual solenoid valve controlling pressure from a manifold to a sole SMB diaphragm valve is practical. In standard SMB having one continuous liquid loop through the entire device, the pattern of open and closed valves is exactly the same for each column position. Thus, this pattern for F, R, D, and E can be programmed for each of the eight columns, and the pressures for each eight column configuration can be under a common pressure solenoid. The minimum number of solenoid valve required for an eight column standard SMB system is eight rather than the 32 required if each diaphragm valve is under separate solenoid control. Solenoid valves suitable for SMB applications are typically three way (vent to atmosphere in position 3) normally open valves. One commercial source of such valves is Spartan Scientific, series 1590.

In another embodiment of the present invention, a compact valve module design eliminates all external control wires for solenoids, and the external pneumatic lines controlling the state of the pneumatic valves. This is a significant improvement in design for situations as in a research laboratory where space is limited and instrumentation is typically compact. The small size of the present instrument lends itself well to research applications in chromatography where milligram amounts of the desired molecular product can be purified on small columns having a bed capacity of one or a few milliliters. The module components are functionally equivalent to the annular embodiment, and operate on the same principles, but are configured differently. The parts may be fabricated of the same materials and utilize the same sources of pneumatic force and pumping means.

Figure 19:
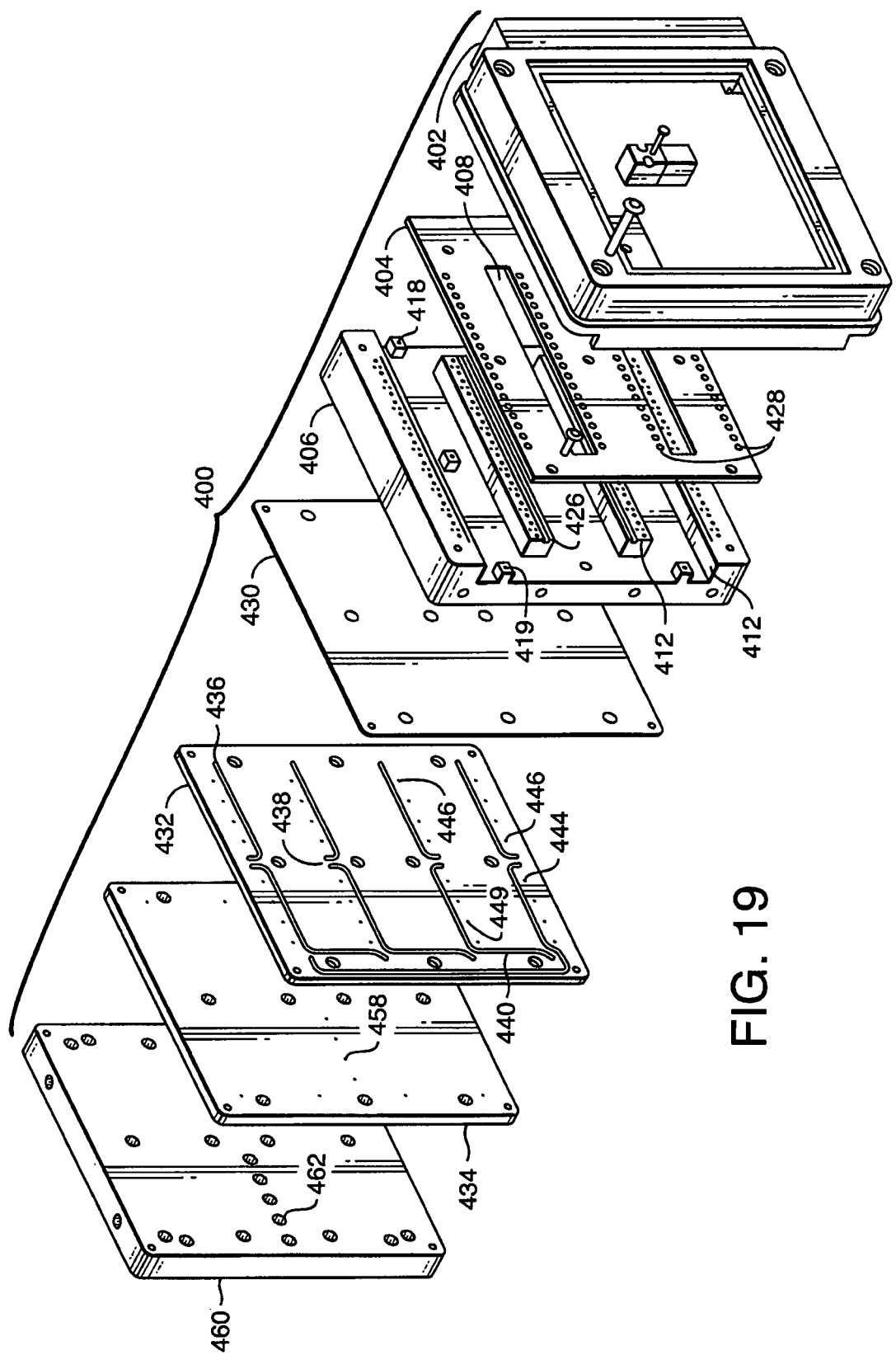
FIG. 19 is an exploded perspective drawing of the right valve block module of the compact device.
Figure 20:
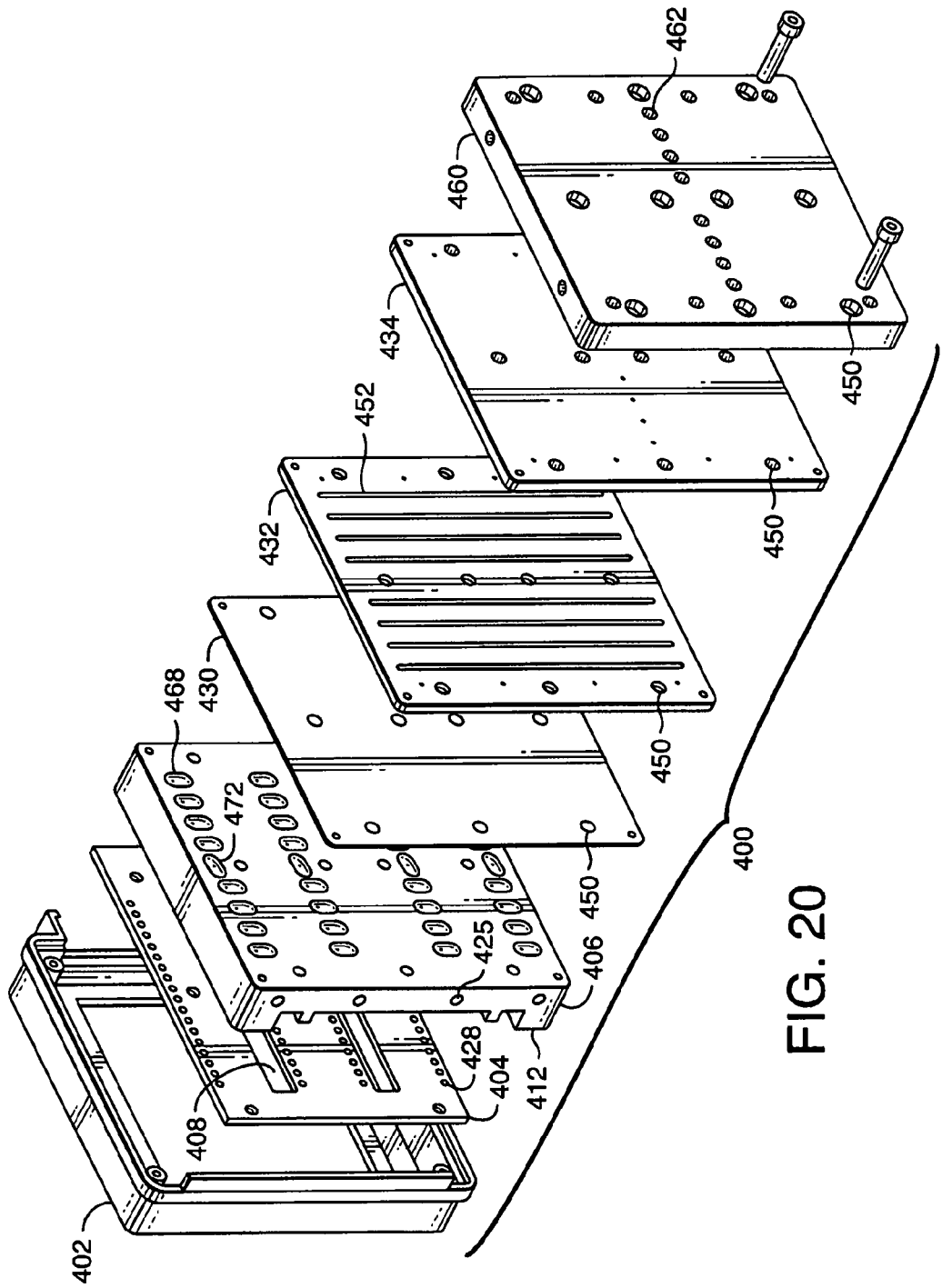
FIG. 20 is an exploded perspective drawing of the left valve block module of the compact device.

FIGS. 19 and 20 are exploded perspective views of the compact unit right and left module, respectively, generally 400, illustrating the six functional plates of the modules utilized in the fully assembled SMB unit, plus an optional cover plate 402. Note that all the plates are rectangular rather than annular in shape, for reasons that will be evident hereafter. The outermost two plates are the two components of a first member of the valve module, and consist of an electronic circuit board 404 and a pneumatic manifold plate 406. The top surface of the pneumatic manifold plate 406 has a plurality (in this case four) raised elongated pedestals 412 and a plurality of posts 418 adapted so that the circuit board 404 will lie flush to the top of the pedestals 412 when assembled. The posts 418 have threaded bores in the top surface for securely fastening the circuit board 404 to the posts 418. The circuit board 404 has slots 408 the same size and shape of underlying pedestals 412 thereby exposing the top surface of the pedestals 412.

Figure 21:
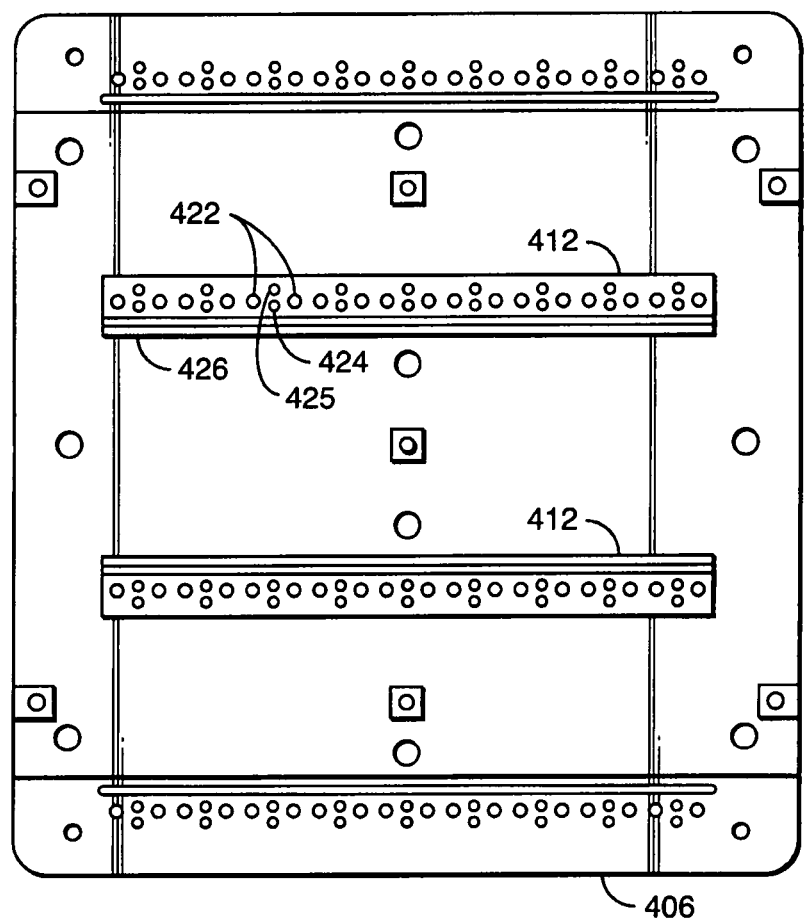
FIG. 21 is a plan view of the upper surface of the pneumatic plate of the compact device.
Figure 22:
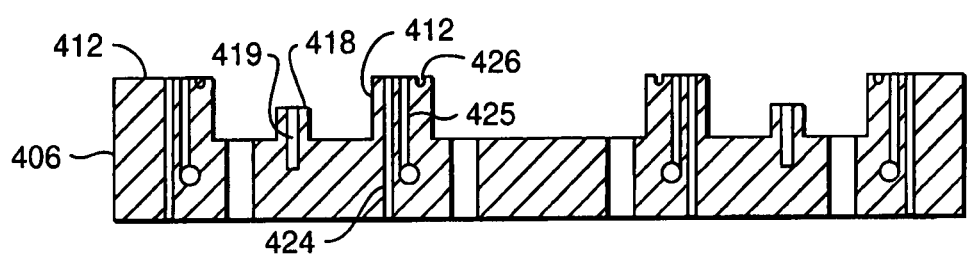
FIG. 22 is a cross-sectional view of the upper portion of the pneumatic plate of the compact device.

Referring to FIG. 21, a plan view of the top surface of the pneumatic plate 406 shows further detail. Each solenoid valve port must be connected to the pedestal 412 and also a two-lead electrical connection must be made to the circuit board 404 to be fully functional. The solenoid valves used in this embodiment are of the type having a rectangular valve body, are normally open, and have a gasketed port for applying pneumatic pressure to pneumatic valves in the device to control patterns of fluidic flow, a gasketed port for incoming gas from a pressurized gas source, and a vent. FIG. 21 shows a series of bores in the top of the pedestals 412, two of them in a horizontal plane 422, and two in a vertical plane 424. The two horizontal bores 422 are threaded and permit securing the solenoid valve body to the pedestals 412 by screws. The two vertical bores 424 and 425 form a sealing engagement of the gasketed ports for delivery of air pressure and an incoming source pneumatic pressure respectively. A vent for exhausting pressure is provided by an exhaust channel 426 running the length of the pedestals 412, open to the atmosphere. In a cross-sectional view, FIG. 22 shows the pedestals 412, the pneumatic bores 424, a manifold channel 425, and the exhaust channel 426. This figure also illustrates the circuit board mounting posts 418 and the threaded bore 419 for mounting the circuit board to the pneumatic plate 406.

Figure 23:
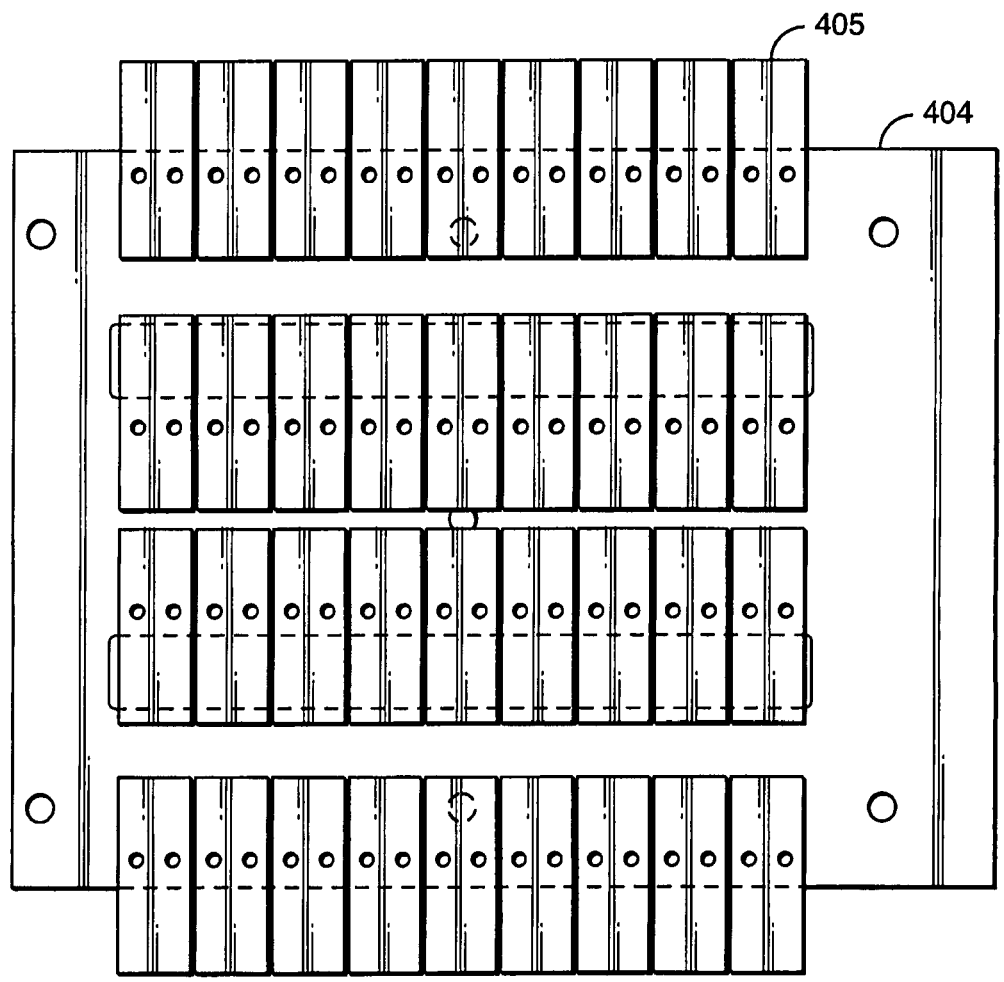
FIG. 23 is a plan view of the circuit board with solenoid valves in place and pedestal feature shown in relief.

Referring again to FIGS. 19 and 20, the circuit board 404 has a series of bores 428 adjacent to the top and bottom edges of the circuit board, and adjacent to each of the slots 408. These bores contain receptacles into which prong power leads insert to connect the solenoids to the circuit board. Each solenoid requires two such prongs to close electrical contact. FIG. 23 illustrates the assembly of solenoids 405 onto the circuit board 404. Dotted lines represent the outline of the pedestals. The distance between pneumatic valve ports is essentially the width of the solenoid valve body, so that the array of solenoids in its most space saving configuration is rectilinear.

A pliant diaphragm 430 is disposed between the pneumatic plate 406 and a fluid transfer plate 432, as shown in FIGS. 19 and 20. This membrane is a fluorocarbon film identical to that used in the other embodiments of the device, and serves the same purpose. The diaphragm is a pliant pressure responsive polymer, sufficiently pliant to permit be deflected when pneumatic pressure is relieved at a valve site, permitting flow from or into valve ports. In closed position, pneumatic pressure against the diaphragm exceeds the fluid present in fluid ports and prevents flow.

Figure 24:
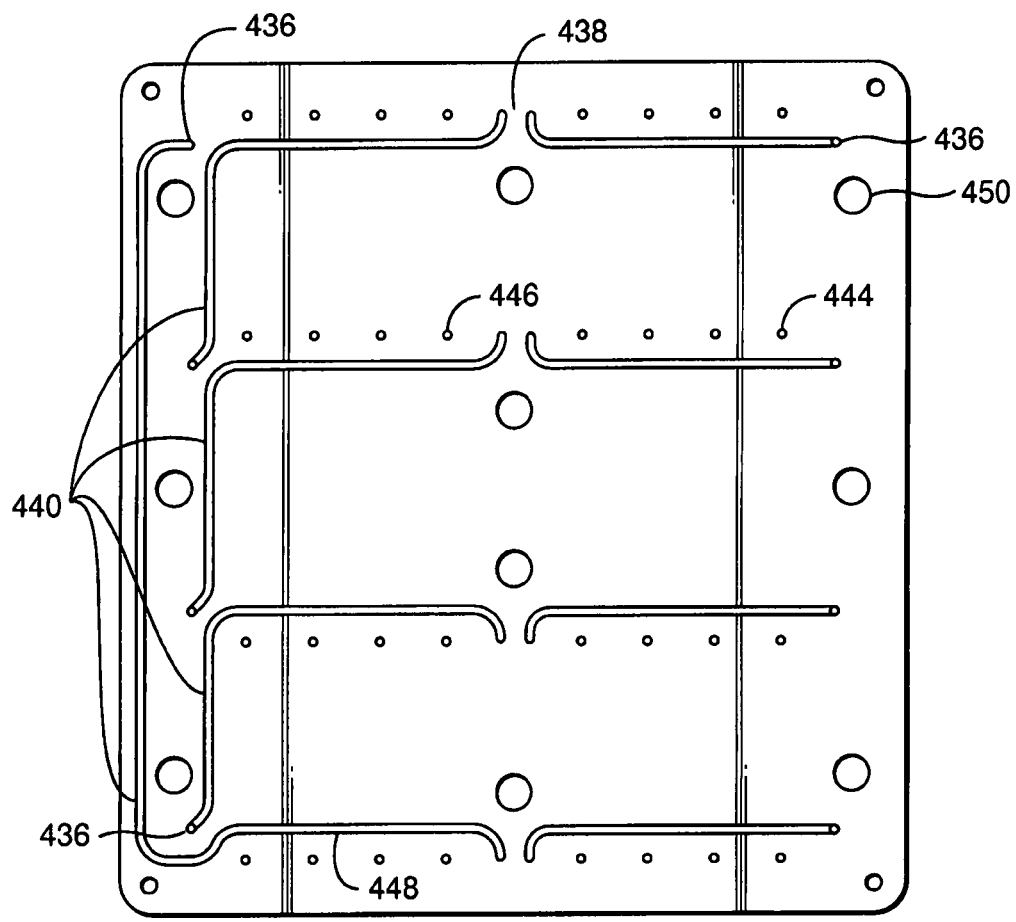
FIG. 24 is a plan view of the upper surface of the right oriented fluid transfer plate.
Figure 25:
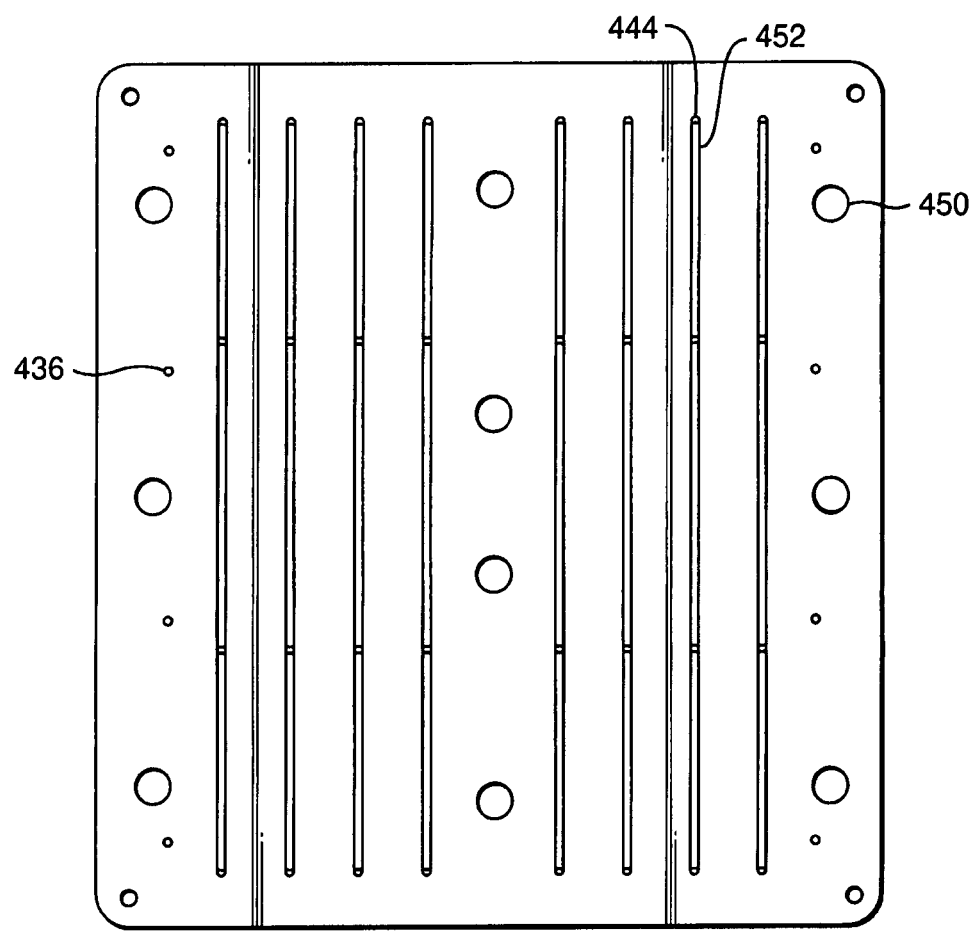
FIG. 25 is a plan view of the lower surface of the fluid transfer plate.

FIG. 19 shows the position of the right module fluid transfer plate 432 disposed between the diaphragm 430 and a sealing plate 434 in exploded view. The sealing plate 434 is optional if bores are countersunk in the anchor plate to ensure that fittings do not have to seal directly against the ingress and egress channels 452 directly. A plan view of the fluid channels etched into the top side of the right module fluid transfer plate 432 is shown in FIG. 24. Fluid transfer channels are depicted by four separate double line structures, ignoring the cut off gap zones 438. Each channel terminates at its ends in a column access port 436. Note the curved portion 440 of each channel, termed the cross-over channel which directs flow from a column access port in the row on one side of the fluid transfer plate to the row of valves above the row where the column access port entered the plate (in three cases) or from the column access port at the top left of the plate 436 to the bottom row of valves (in the fourth case). The serpentine channel that connects the access port 436 at the top left of the lower array to the access port at the top right of the upper array ensures that there is a complete fluid loop among all the columns, so that the cycle can be repeated indefinitely. The small bores 444 and 446 are fluid egress and ingress ports respectively for drawing off or introducing liquids into the stream. The reverse side of the fluid transfer plate 432 is shown in exploded view (FIG. 20) and in greater detail in the plan view of FIG. 25. Referring to FIG. 25, there is a plurality of ingress and egress channels 452 etched into the lower surface of the fluid transfer plate 432. Each channel is shown with four bores 444 which correspond on the bottom surface to the same bores depicted on the top surface in FIG. 24 and which extend from the upper surface to the lower surface. When an ingress valve is open, liquid will flow into the chromatography stream through an access port from the corresponding ingress channel. Column access ports 436 in this layer of the device are shown with the same number label in the top view in FIG. 24.

Referring to FIG. 19, the ingress and egress channels 454 are sealed by a barrier plate 434 having bores 458 aligned to access each of the ingress and egress channels and column access bores, and secured by an anchor plate 460 under mechanical pressure. The anchor plate 460 has bores 462 aligned with the bores 458 and column access bores. These bores are shown larger than those in the barrier plate, because the larger orifice is needed to accommodate conventional connecting fittings. The bores 450 (for example FIG. 20, 25) are present in the functional plates to secure the layers together, and to maintain alignment. The barrier plate 456 is easy to manufacture and ensures a liquid seal between the anchor plate 460 and the ingress and egress channels 452. However, the anchor plate 460 can be machined with counterbores presenting a seating surface that may substitute for the barrier plate 460.

Figure 26:
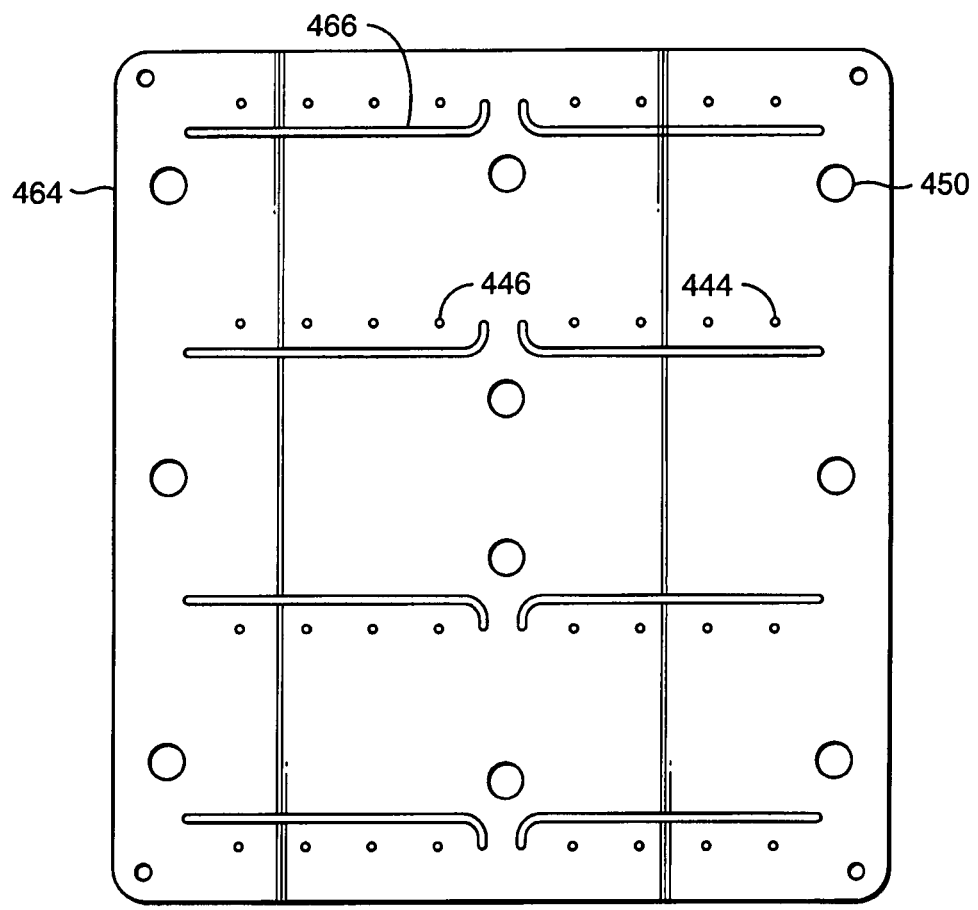
FIG. 26 is a plan view of the upper surface of the left oriented fluid transfer plate.

The upper surface of the fluid transfer plate 432 is a different configuration for the left and right valve modules, and it is the only difference in structural components for the two modules comprising the complete instrument. FIG. 26 shows the configuration of fluid transfer channels 466 for a left oriented module. In this fluid transfer plate 464 there are no cross-over channels. The transfer channels 466 are directed from a column access port at one position in the row of ports to the column access port in the second row of ports immediately opposite the first. These structures retain the flexibility of interrupted flow having a gap 438 in the channel identical to that in the right oriented fluid transfer plate. Like the right oriented fluid transfer module, the left module fluid transfer channels 466 also has a plurality of ingress and egress ports 444 arranged in an array in liquid flow proximity to the transfer channels 466.

Figure 27:
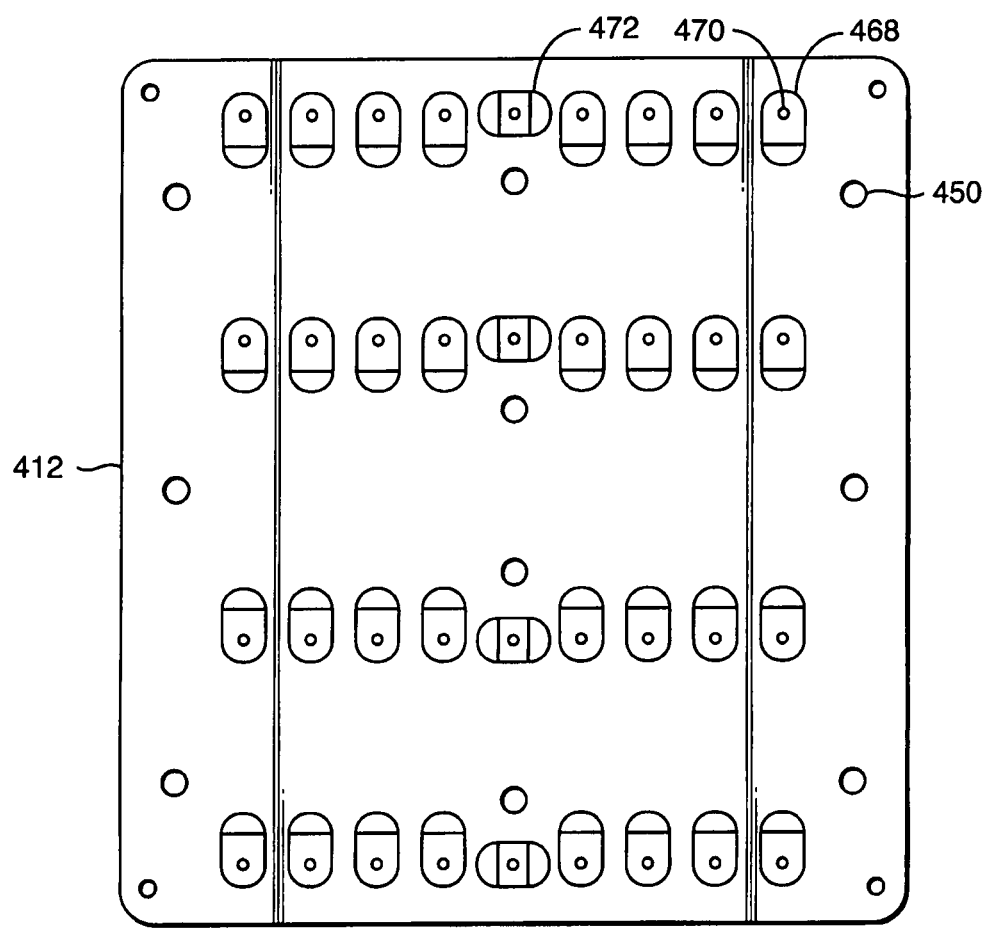
FIG. 27 is a plan view of the lower surface of the pneumatic plate.

The pneumatic valves that define the state of flow in the SMB system operate on the same principles as the other embodiments. Pneumatic pressure applied to the diaphragm keeps the valve closed. When pressure is relieved the fluid pressure in the fluid channels in the fluid transfer plate is sufficient to open them deflecting the diaphragm into the recesses in the bottom of the pneumatic plate. The offset bores are close enough to the channels to bridge the gap between the offset bore and the channel to allow liquid to enter or leave the channel. FIG. 27 is a plan view of the bottom surface of the pneumatic manifold plate 406 for the compact embodiment. The recesses 468 are shown as ovals with the manifold channel 470 depicted as a small circle slightly off center. The recesses 472 corresponding to the flow intervention gap (see FIG. 27, 438) are rotated 90 degrees to be shown as horizontal. This is to be able to maintain the same distance between the ends of the interrupted channel and the distance between the channel and the offset ingress and egress bores (444 and 446; 466, FIG. 26).

Figure 28:
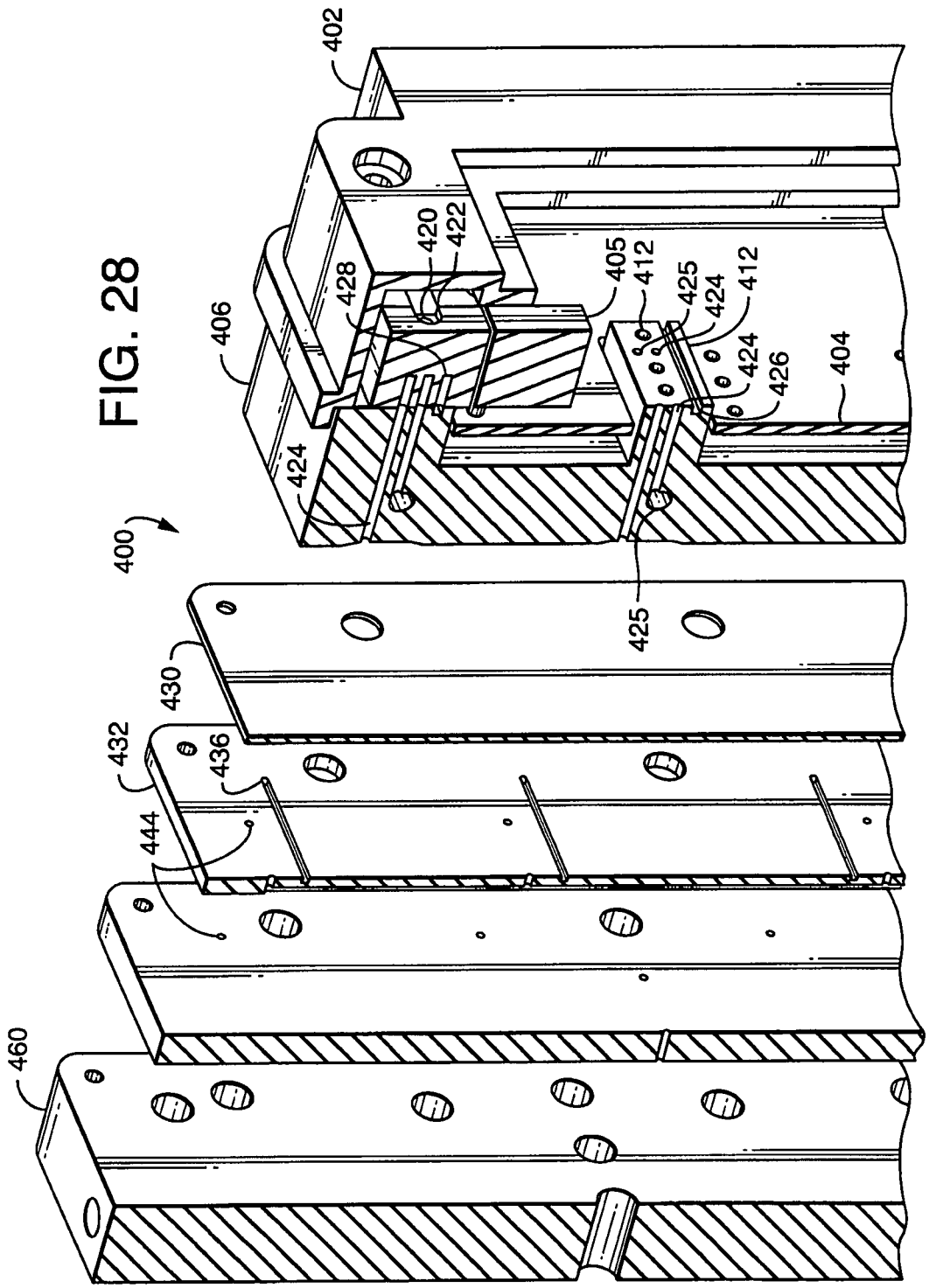
FIG. 28 is a left facing partially exploded cross-sectional view of the upper right corner section of the right valve block module of the compact device.

The configuration and inter-relationship of the compact device is further elucidated by referring to FIG. 28, a partially exploded cross-sectional left facing view. The optional cover 402, circuit board 404, and pneumatic plate 406 are shown as an assembled unit. The half solenoid 405 is secured in place via screws onto the circuit board 404. It is important that mounting is secure to prevent leaks at the interface of the solenoid valve ports and the corresponding bores 424, 425 in the pedestal 412. The figure shows that those junctions are flush, and leakage is prevented by applying pressure from the screws to compress the gaskets sandwiched between the valve ports and the pedestal. The exhaust channel 426 is a three sided open groove open to the atmosphere on the pedestal 412 and corresponds in alignment to the exhaust port on the underside of the valve body 405.

Figure 29:
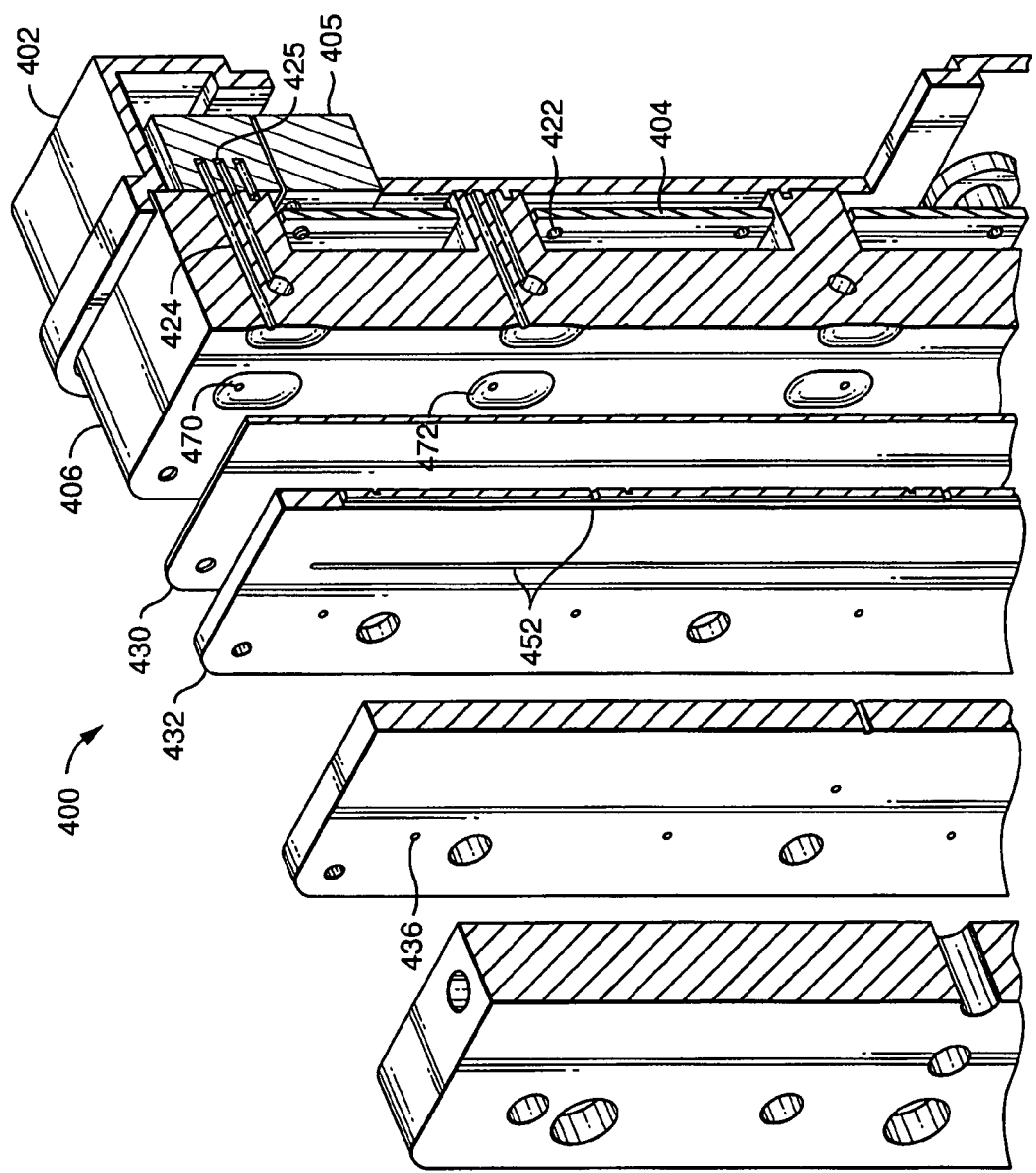
FIG. 29 is a right facing partially exploded cross-sectional view of the upper right corner section of the right valve block module of the compact device.

FIG. 29 is a right facing partially exploded cross-sectional perspective view of the valve module components showing the lower surface of the pneumatic manifold plate 406. The pneumatic channel 424 traverses the pneumatic plate 406 from the interior of the solenoid valve body 405 terminating in a recess 472. The figure shows one half of the orifice 470 within the recess, and the partial lower surface of a left fluid transfer plate 432 with vertical ingress and egress channels 452.

Figure 30:
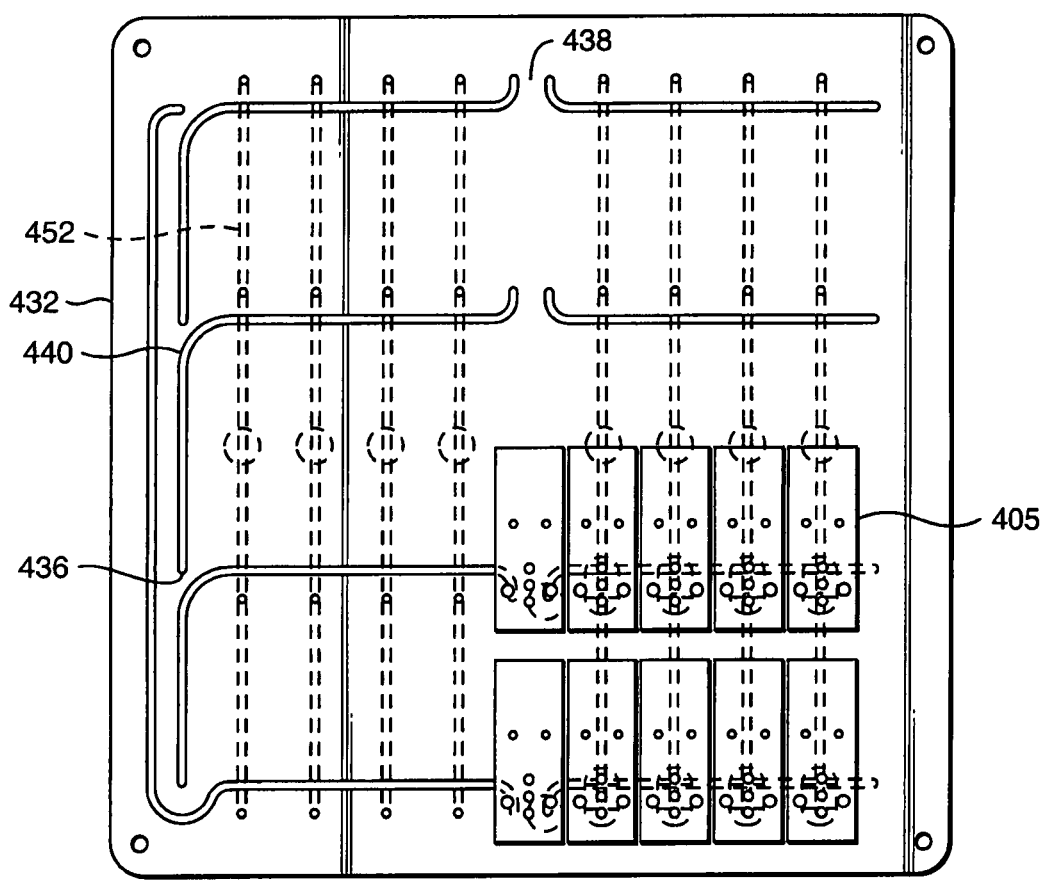
FIG. 30 is a plan view of the right oriented fluid transfer plate showing the position of solenoids and the ingress and egress channels in relief.
Figure 31:
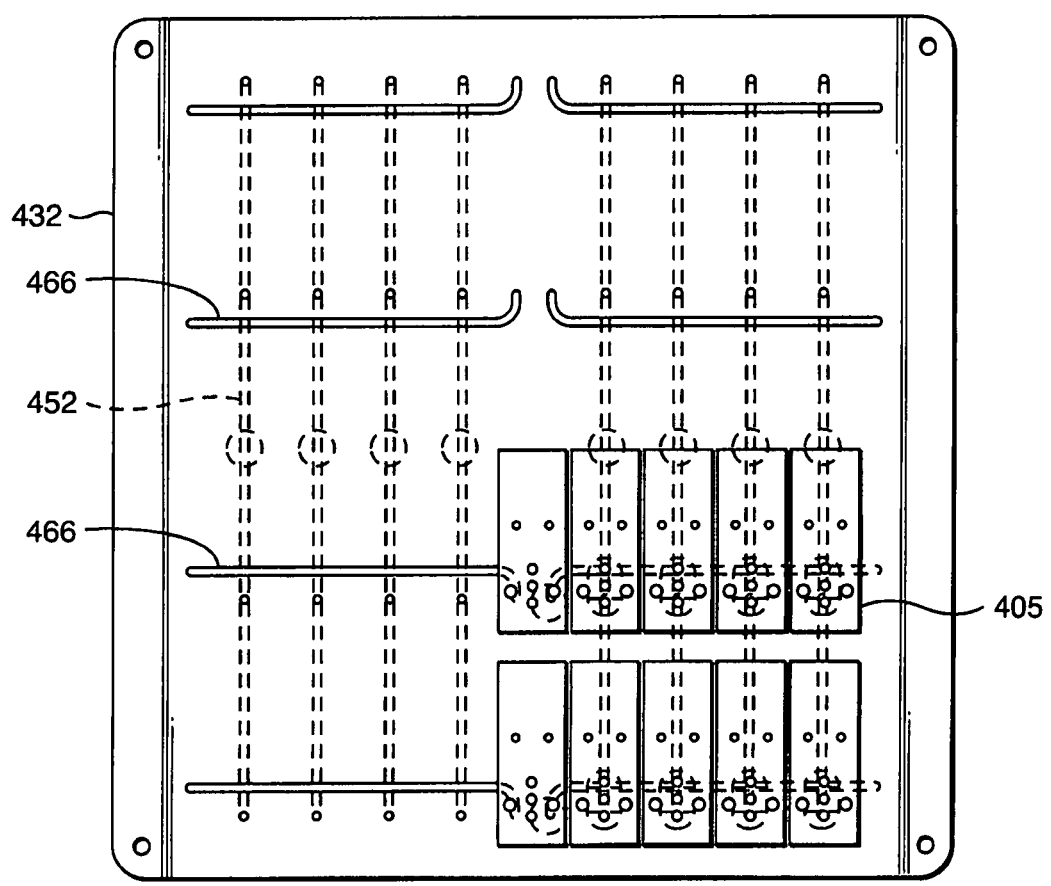
FIG. 31 is a plan view of the left oriented fluid transfer plate showing the position of the solenoids and the ingress and egress channels in relief.

FIGS. 30 and 31 show a plan view of the right and left configurations of the fluid transfer channel 440 and 466 respectively, with the dotted line structures depicting underlying ingress and egress channels 452. There is a corresponding bore at the intersection of the ingress and egress channels 452 to provide a vertical fluid connection therebetween. Valve bodies 405 are shown in their position relative to the liquid flow channel system.

Figure 32:
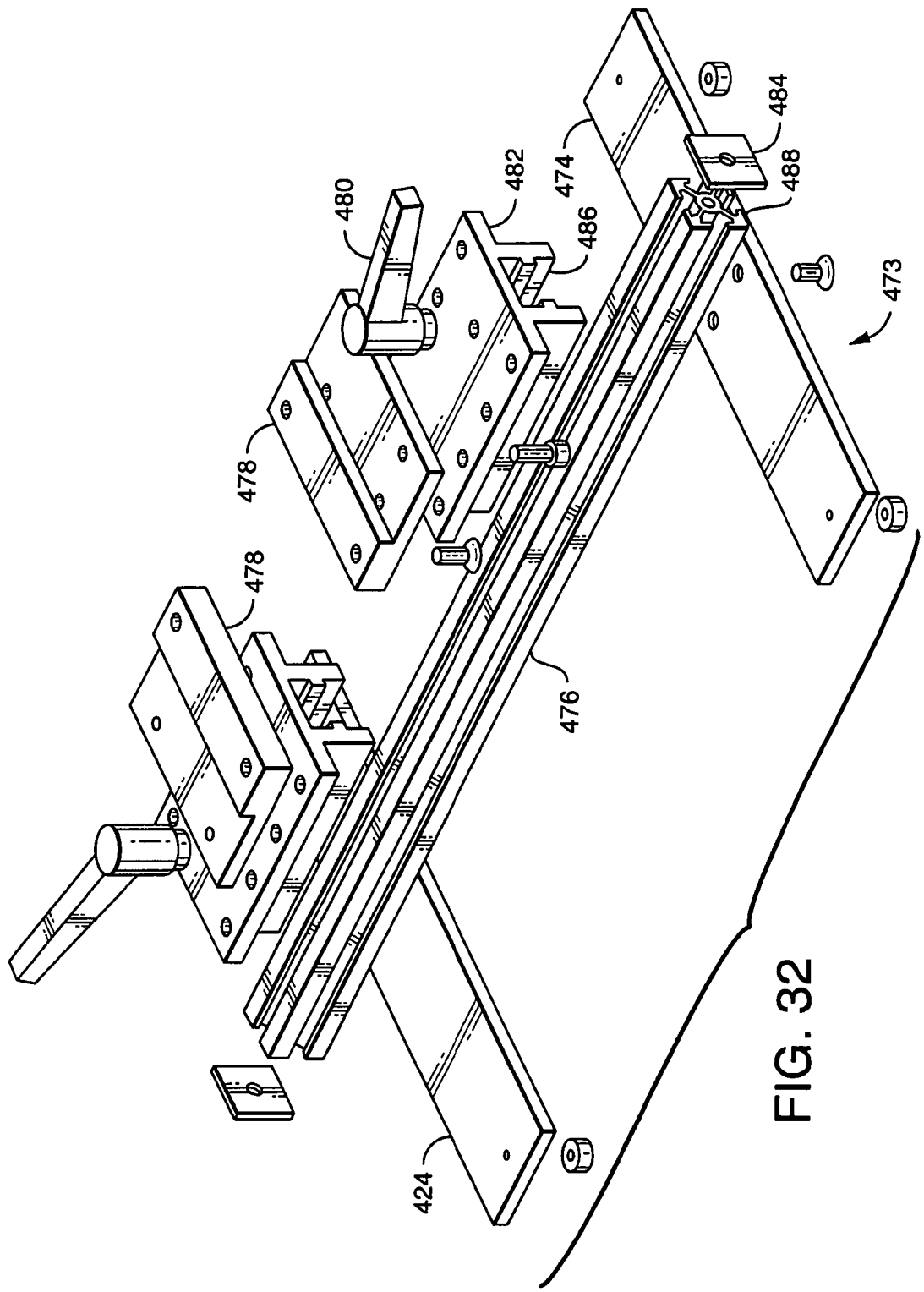
FIG. 32 is a perspective view of the components of the carriage for mounting valve modules.

In actual operation a right and left valve module face each other in opposite orientation with chromatographic columns connecting the two modules, thereby creating continuous back and forth fluid contact. A one-way check valve is place in line on each column in order to prevent bi-directional flow in the system. Since there is no air in the fluid transfer system, theoretically, the two modules can be oriented in any plane. As a practical matter, a horizontal arrangement is most convenient for assembling the columns and bleeding air from the column connectors. FIG. 32 shows a carriage for horizontally mounting the valve modules. The carriage comprises a track 473 consisting of foot members 474 on which a track member 476 is mounted. Adapter plates 478 are adapted to bolt to the modules. The adapter plates are attached to a movable carrier 482 which slides onto the track member 476 and conforms to the inner female surface thereof. A cam (not shown) is adjusted by a cam handle 480, to fix the modules mounted carrier 482 in the desired position. This device anchors the modules and permits insertion of columns of varying length.

Figure 33:
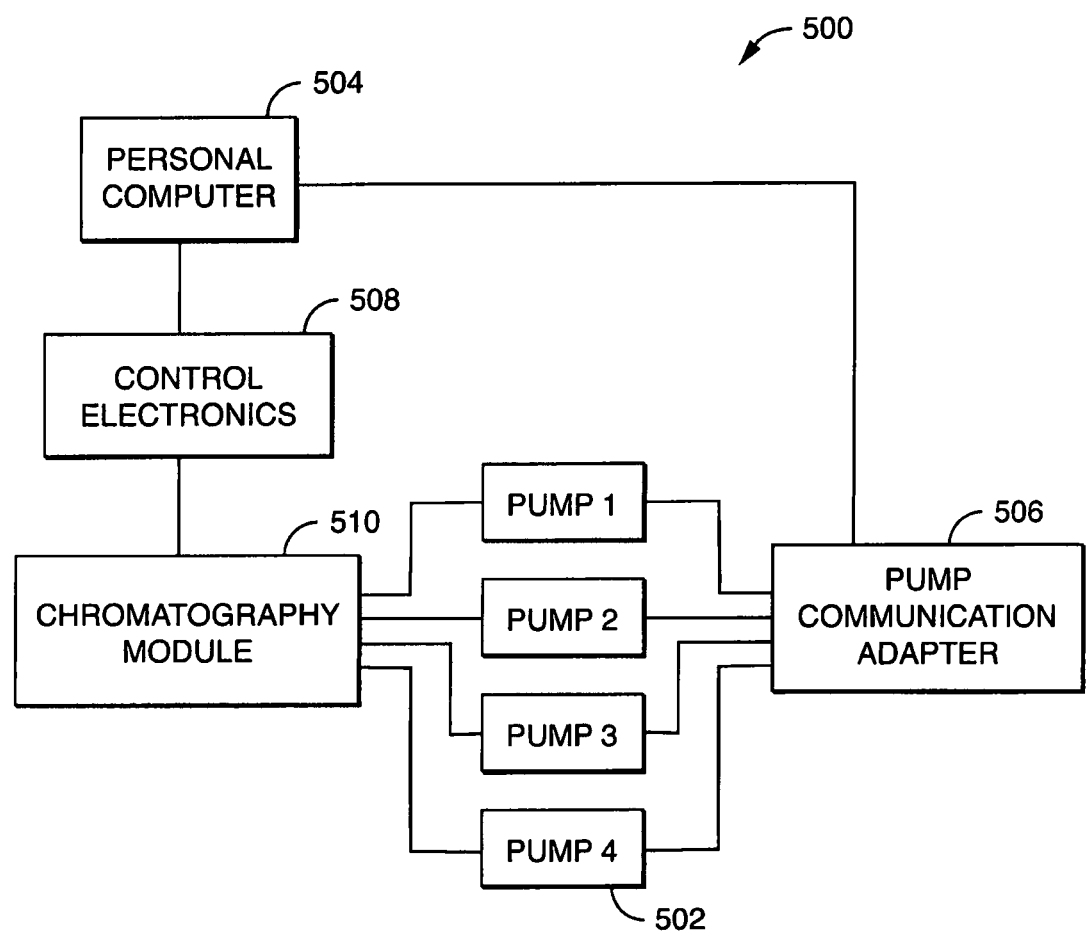
FIG. 33 is a block diagram illustration of an exemplary control system for an SMB system in accordance with the present invention.

A more detailed description of a control system 500 for an SMB system in accordance with the present invention will now be described in more detail beginning with reference to FIG. 33. Control of an SMB system in accordance with the present invention to implement a desired process requires control of the states (open or closed) of the various valves implemented in the valve blocks 10 in the accordance with the present invention and control of the various pumps 502 that direct the flow of fluid in and out of the system. Preferably such control is implemented in a user-friendly manner using a personal computer 504 or similar programmable device. Control software implemented on the personal computer 504 is used to generate control signals that are provided to control operation of the pumps 502, via an appropriate pump communication adaptor 506, and to control the states of valves in the valve blocks 10 via appropriate control electronics 508 and valve operation devices found in the chromatography module 510.

Since the computer processing requirements to implement a control system 500 for the present invention are not very demanding, any appropriate conventional personal computer system 504 or similar programmable device may be employed to implement the control system 500. Such a personal computer 504 should preferably include conventional input and output devices, such as a keyboard, mouse, display screen, and the like that allow a user of the system to interact with the control software implemented therein. Sufficient conventional memory should be provided for the computer system 504 for storage of the computer program for implementing the control functions described herein, including the look-up table to be described below, as well as conventional operating system and other software required or desired for general operation of a general purpose personal computer 504. Based on the detailed description and drawing figures, including exemplary screen shot figures, provided herein, a person of ordinary skill in the art of computer programming for industrial or laboratory controls will be able to implement a software program for performing the user interface and control functions described herein using conventional programming languages on a conventional personal computer running a conventional operating system (such as Windows or Mac OS).

The control software implemented in the computer system preferably provides for control of pump flow rates via a direct communication between the personal computer 504 and the pumps 502 themselves. For example, a Universal Serial Bus (USB) cable may be used to connect the personal computer 504 to a converter implemented in the pump communication adaptor 506 that takes the USB connection and splits it into separate serial connections (e.g., in the example shown, four separate serial connections, one for each pump. The control software in the personal computer 504, responding to user input, sends a command to each pump 502 telling it what flow rate to pump at and the pump 502 responds by adjusting its flow rate. Of course, it should be understood wired or wireless communications between the personal computer 504 and the pumps 502, and control circuitry therefore, other than that described by example herein, may be used to control pump operation.

Figure 34:
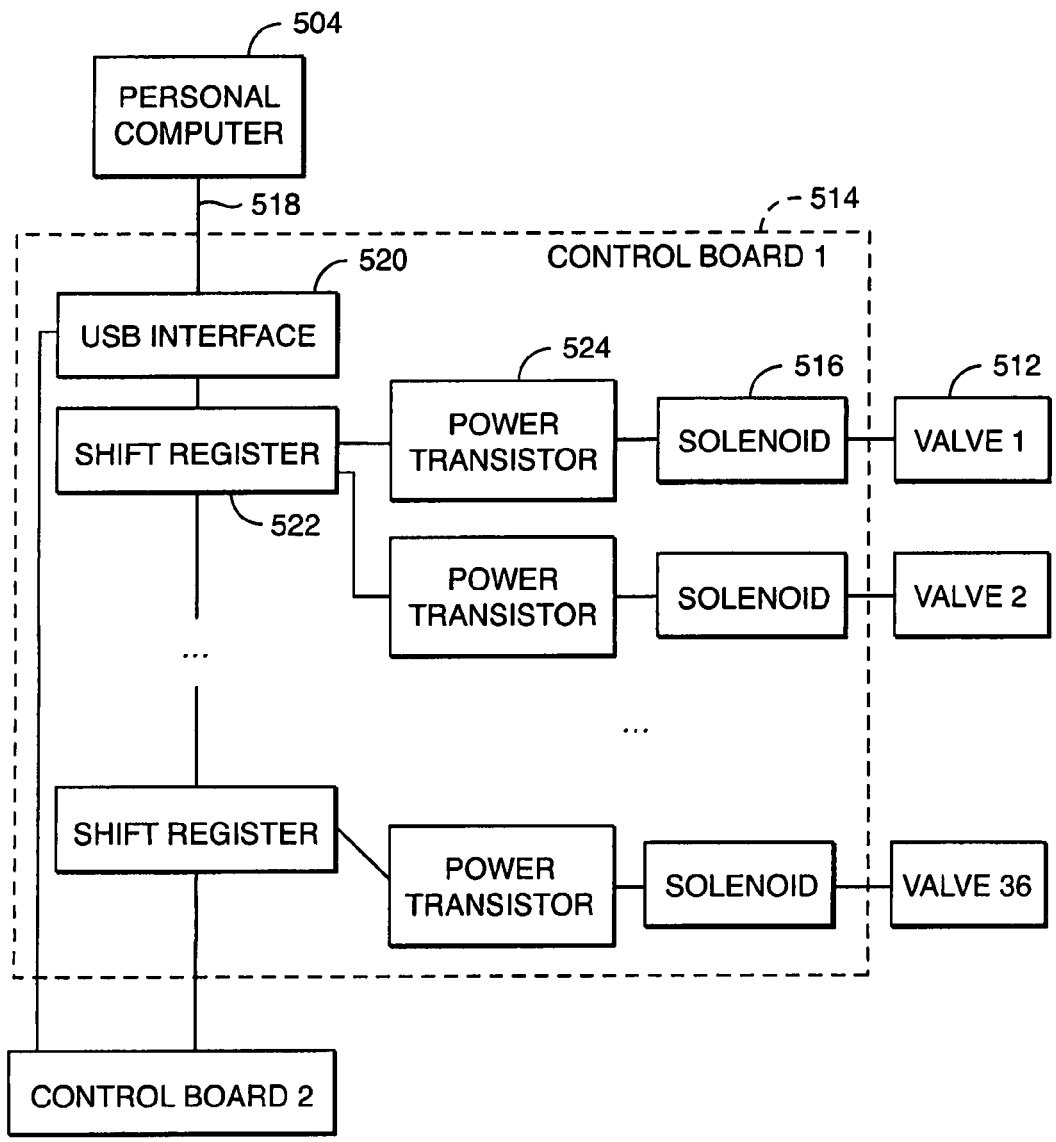
FIG. 34 is a block diagram illustration of a portion of the control system of FIG. 33 for controlling the state of the valves in a valve block in accordance with the present invention.

Turning now to FIG. 34. The chromatography module 510 relies on precise control of the valves 512 in the valve blocks 10 (e.g., in the example being presented, a total of 72 valves, 36 on each side of the columns of the SMB system in accordance with the present invention, although any other number of valves may be used as appropriate) to direct the flow of fluid in a manner that simulates a moving bed. The starting point for this control is the control software running in the personal computer 504 that generates control signals that are provided, via the appropriate control electronics 508, to implement such precise control. In a preferred embodiment of the present invention, when the control software needs to alter the current state of the valves 512 within the chromatography module 510, it sends a patterned data stream to an electronics control board 514 that interprets this control signal input and directs the action of solenoids 516 (one per valve 512) that, in turn, control the gas or other fluid pressure applied to the diaphragm 14 in the valve block 10 for each valve, thereby opening or closing the appropriate valves in the manner discussed above.

For example, the state (open or closed) of each valve 512 in the system may be defined by the bits in a patterned bit stream that is generated by the control software running in the personal computer 504 and provided at the control electronics 508 via a USB or other appropriate wired or wireless connection 518. A USB interface chip 520 on the board 514 takes in the digital input, processes it, and turns on and off wires leading from the interface chip 520 to devices, e.g., a series of shift registers 522, that store and present the individual control bits for operation of each valve solenoid 516. One of the wires from the interface chip 520 is connected to the first of the series connected shift registers 522 for carrying the bit pattern corresponding to the desired state of the valves 512 to the shift registers. This bit pattern is fed into the series connected shift registers 522 to load the shift registers as necessary to control the desired number of valves 512. For example, if eight bit shift registers 522 are used, each shift register can hold and present the bits defining the state of eight valves 512. To control 36 valves, for example, eight bits are first shifted into the first shift register 522. These eight bits are then shifted to the second shift register 522 in series as eight additional bits are shifted into the first shift register 522. This process is repeated, shifting the bit stream downward in the series connected shift registers until sufficient shift registers are loaded with the desired bit stream representing the desired state for 36 valves. Timing and control of this bit shifting/loading process is provided by another wire leading from the interface chip 520 to each shift register 522, which acts as a serial clock.

After the appropriate bits have been set in the shift registers 522 an update of the state of the valves 512 is triggered by a third wire leading from the interface chip 520 to each of the shift registers 522. This third wire is connected to the shift register pin for presenting the new loaded shift register contents at the specified output pins of each shift register 522. These shift register output pins are connected to appropriate power transistors 524 which are sufficient to drive enough current to turn on or off a connected solenoid 516 depending upon the bit value (0 or 1) presented to its input by the shift register. As discussed above, each solenoid controls the delivery of high pressure gas or other fluid to the membranes 13 in the valve blocks 10 to control the valve state (on or off). Thus, the digital outputs from the shift registers 522 direct the turning on or off of each valve in the chromatography module 510.

In the exemplary embodiment being discussed herein, two control boards 514 are used to control 72 valves 512 in the system (each board 514 controls 36 valves). The interface chip 520 on the first board 514 sends half of the control bit stream to its series of shift registers 522 and the other half is relayed to the second control board 514 through another wired connection. (Thus there need not be a separate USB interface on the second control board.) If more valves need to be added to the device, the overflow from the last shift register on each board may be daisy-chained to yet another board of the same configuration.

The control software running on the personal computer 504 preferably provides a user-friendly interface that allows a system operator to define the state (open or closed) of the valves 512 in the system. Preferably the software provides for both manual control of the valve state across the module and an automated switching of those states.

Figure 35:
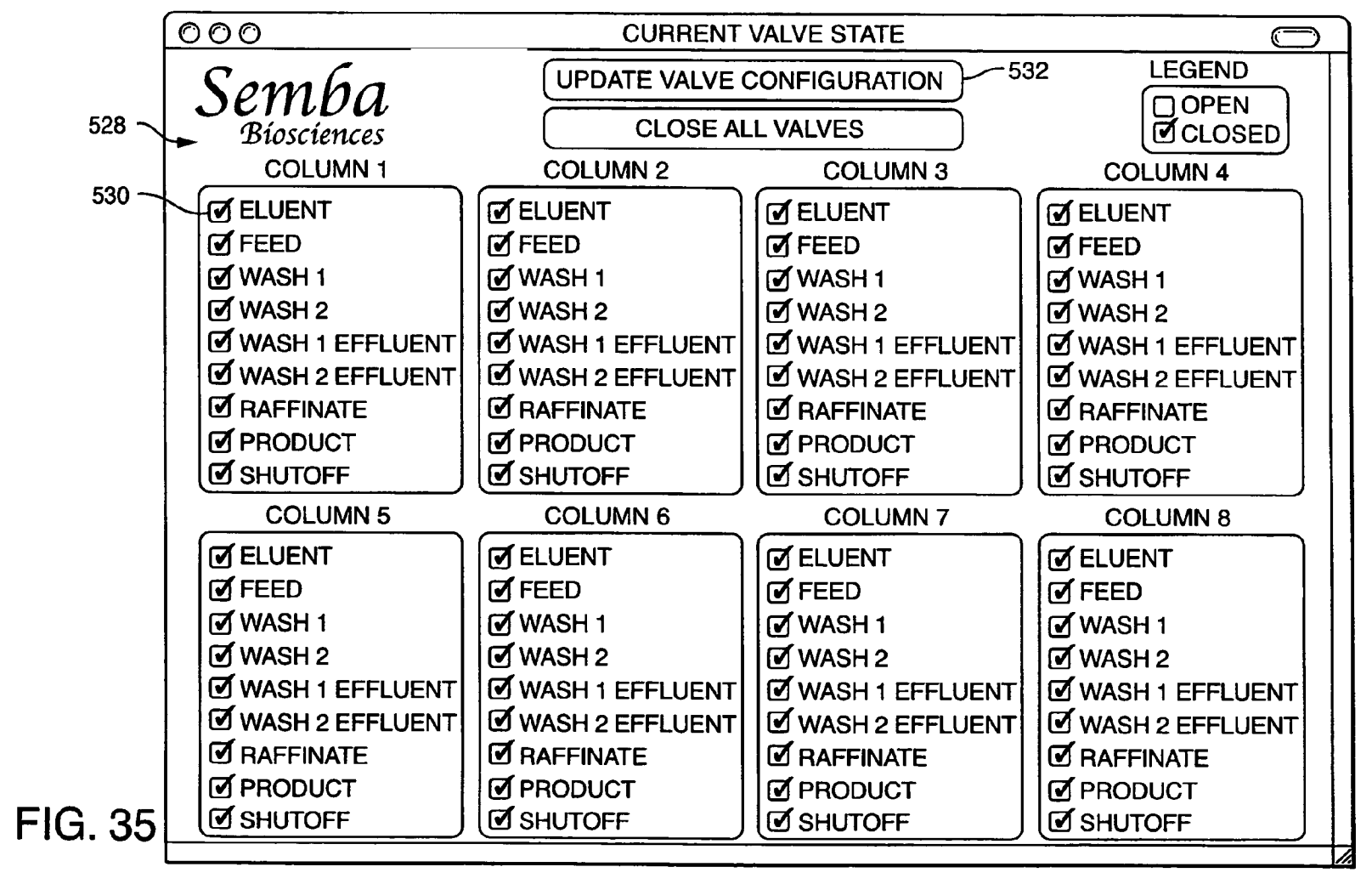

Manual control provides the ability, for example, to test the chromatography module 510 to determine if its individual components are functioning properly. Manual control of the valve states may be accomplished by the user activating the control software and opening a graphical user interface window that depicts the current valve state of the module. An exemplary graphical user interface 528 of this type is illustrated in FIG. 35. This manual control user interface 528 presents a check box type control interface 530 for each valve in the system that may be controlled. The user selects the desired valve state for each valve by checking or un-checking, as appropriate, the check box 530 corresponding to the valve. Once the desired valve states are selected in this manner the user clicks an update valve configuration button 532 that commands the software to update the state of the valves as just defined.

After the user clicks the update valve configuration button 522 the software processes the desired valve state by checking each valve depicted in the user interface 528 against an internal look up table that indicates which location on the electronic control board shift registers 522 corresponds to that valve. Once the location of each valve has been identified, the software creates the appropriate sequence of bits (1s and 0s) that are loaded onto the shift registers 522 in the manner described above. Finally, the controlling electronics triggers the shift registers 522 to present the loaded bits at the shift register outputs to set the valves across the system to their new state, in the manner described above.

Figure 36:
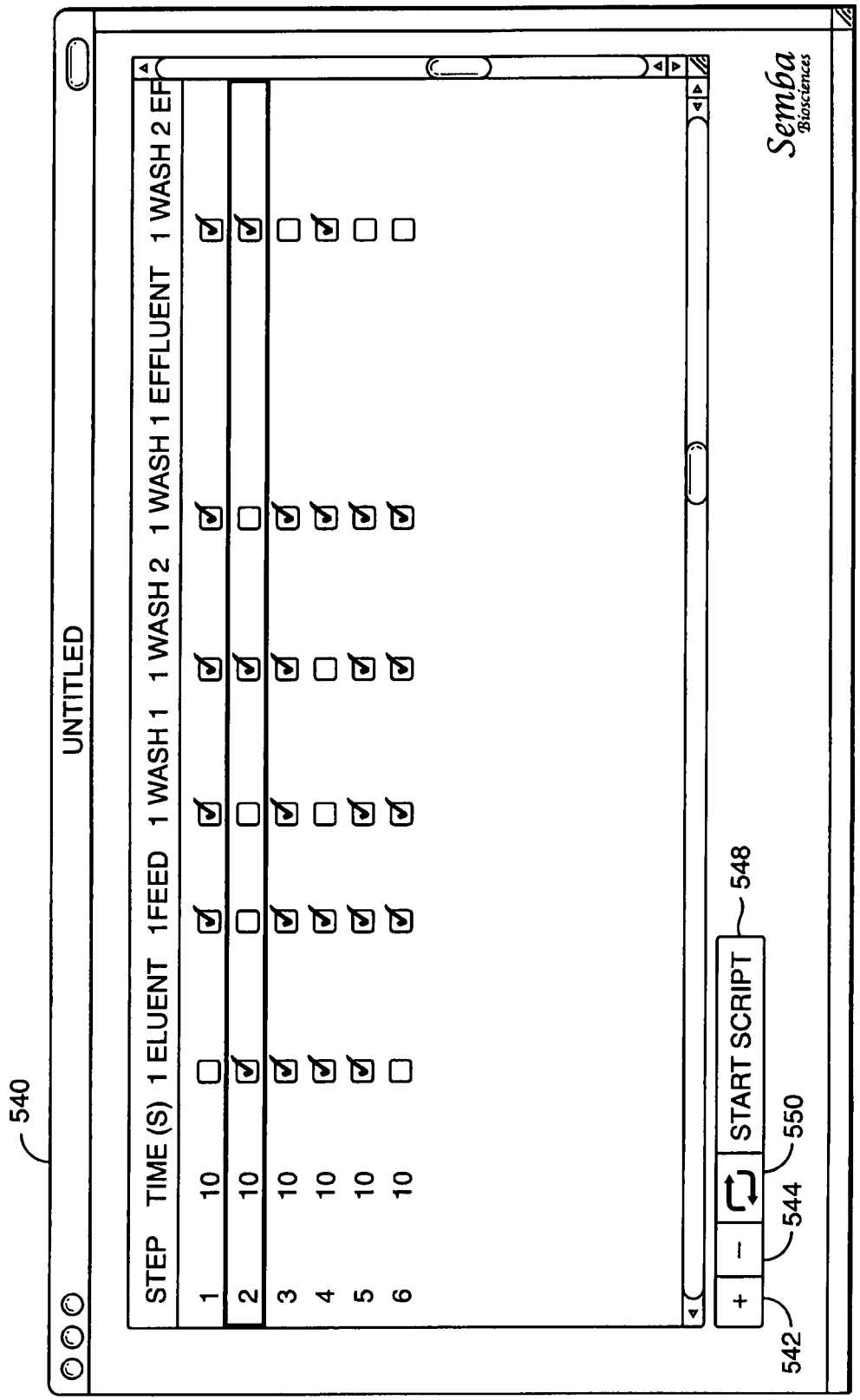
FIGS. 36 and 37 are exemplary screen shot illustrations of graphical user interfaces for defining valve state steps for automatic process control in a control system in accordance with the present invention.
Figure 37:
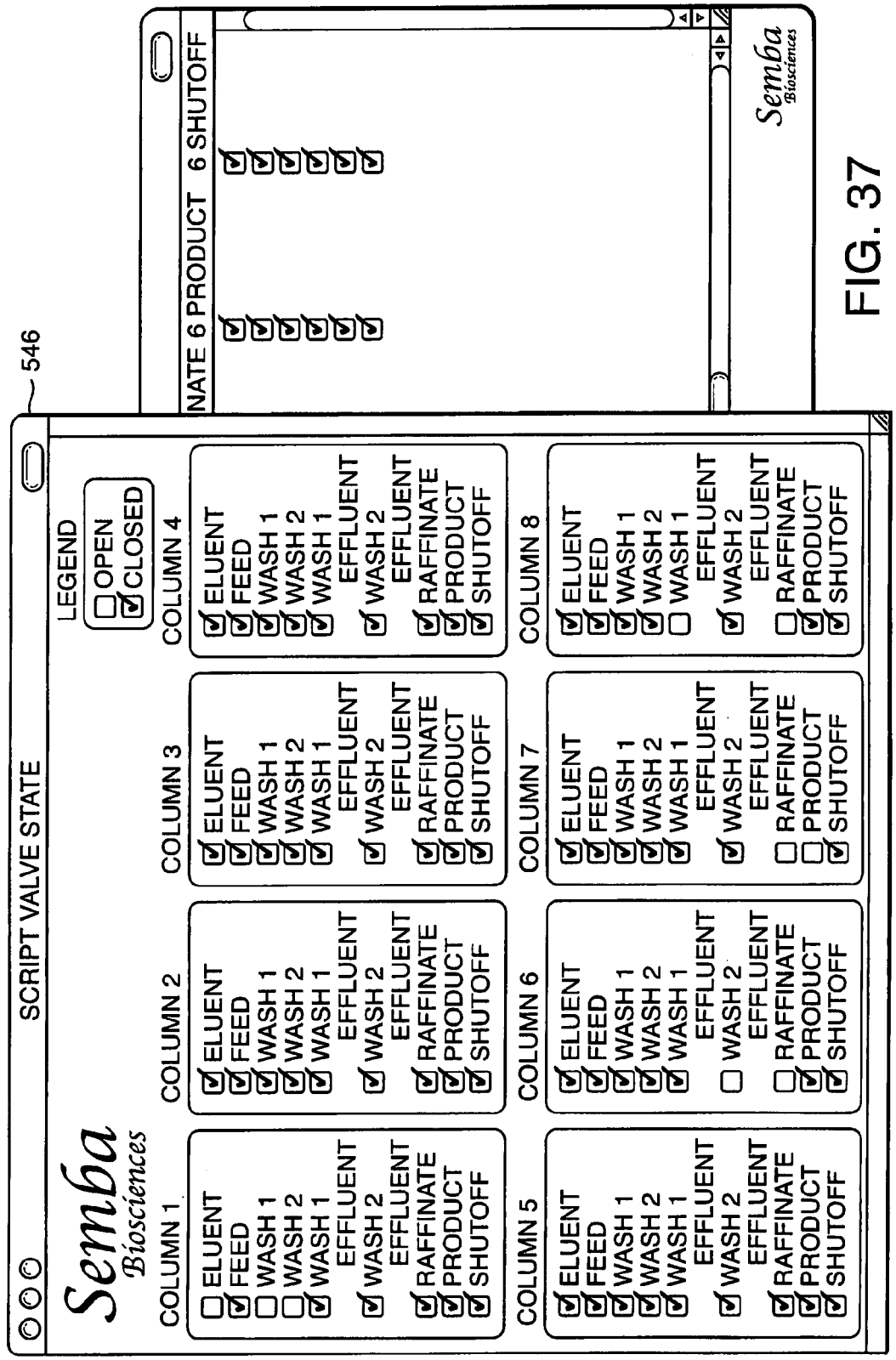

To direct the controlled switching of valve states in an automated manner, e.g., to perform a separation, the controller software preferably provides the user the ability to input sequences of valve states in the form of scripts that the software runs in an automated fashion. An exemplary graphical user interface showing an exemplary user definable control script 514 of this type is shown in the screen shot illustration of FIG. 36. These scripts consist of a series of steps in a process, each of which defines the system valve states in a manner similar to that used to define the valve states in the manual control method described above. However, in this case each step also includes a user selected time period, e.g., in seconds, that the system will remain in the defined valve state configuration before switching to the next step. The graphical user interface preferably provides virtual buttons for allowing a user to add 542 or delete 544 steps from the script. If the user selects to add 542 a step a new graphical user interface 546 window, as shown by example in FIG. 37, may pop up to allow the user easily to define the state for each valve for that step.

Returning to FIG. 36, upon the user selecting a button 548 to run a defined script, the first step in the script is read and processed, in a manner similar to that described above for the manual control, to generate a bit pattern that is sent to the control electronics 508. The software waits for the time duration specified by the step, then repeats the process for the valve states defined for the second step. When the end of the scripts has been reached, the software can either loop back to the first step, at the users selection 550, or terminate execution, based on a configuration setting for the step.

It should be understood that the control software may provide additional and/or different graphical user interface options, and/or in a different format, from that presented by example herein. For example, the graphical user interfaces may provide options for the user to save individual valve state configurations and/or scripts and retrieve them for later use.

The principle of standard affinity chromatography relies upon the high specificity of the binding event of the target protein to the ligand-bound resin. In a typical batch procedure, target protein present in a feedstock contacted with the resin is immobilized on the resin. The column is then thoroughly rinsed with a buffer of the same or similar type as that in the feedstock to remove all the unbound contaminants. Finally, the target protein is eluted with an affinity neutralizing agent, and the target is released from the resin and collected. It is generally accepted by those skilled in the art, that it is desirable to take full advantage of the binding specificity by binding under conditions that achieve maximum static immobilization of the target protein to the resin, i.e. under conditions in which the feedstock contains none or very low concentrations of the affinity releasing agent.

However, this strategy has its trade-offs. Most complex protein mixtures containing the target protein of interest also contain unrelated proteins that have weak binding affinity for the column resin, presumably because they share or mimic binding domains. When the affinity releasing agent is applied to the column these contaminating proteins unrelated to the target are also released and contaminate the final eluant. If higher purity is desired, the target protein must be re-purified using another separation technique which will lead to a reduction in yield.

Applicants have discovered that higher levels of purity of a target protein can be achieved under conditions in which the binding affinity is attenuated and one concentration of affinity releasing agent is used throughout the entire standard SMB run. These conditions are termed isocratic. While not being bound to any particular theory, it appears that at concentration in a range of less than that required to release bound protein from the resin, the target protein migrates in a mobile front, but, because of residual affinity interactions with the affinity ligand, is retarded in its passage through the column in contrast to proteins having little or no affinity for the resin. A higher attained level of purity in the extract is possibly explained by considering that the weakly bound contaminating proteins found in conventional affinity chromatography are not retarded in elution and pass along with the bulk of unrelated proteins into the raffinate.

This phenomenon also may be accounted for by the nature of countercurrent flow in SMB chronmatography, since flow rates and column switching times can be varied to sharpen the target peak, and reduce the overlap of extract and eluent. A further enhancement of purity can be obtained by "peak shaving" by adjusting flow rates and valve switching to permit the leading edge of the extract peak to be sacrificed in the raffinate. While theoretical models can be constructed to predict the selection of optimum running conditions, empirical observation is efficacious and does not require undue experimentation. This is illustrated in Example 2 hereinbelow. In this example, experiments are presented using a his-tagged recombinant protein having a selective affinity for chelated nickel bound to a resin matrix. Many other model affinity systems are known, to which the present SMB chromatography device and methods are applicable, and include both recombinant tags and endogenous affinity domains exhibiting selective specificity for a ligand bound to a column matrix. One particularly important affinity system is the purification of antibodies and other molecules having immune specificity. Among the most prevalent methods are affinity systems exploiting the affinity domains contained in IgG specific for Proteins S and G. According to the method of the invention, the skilled artesan would select pH buffer systems at a pH below the binding pH (pH 7.4-9.0), testing a few pH point between pH 3.0 and pH 7.4 to determine a range of pH where the antibodies are retarded in mobile phase relative to the other contaminating proteins in a crude acites or other extract.

Figure 14:
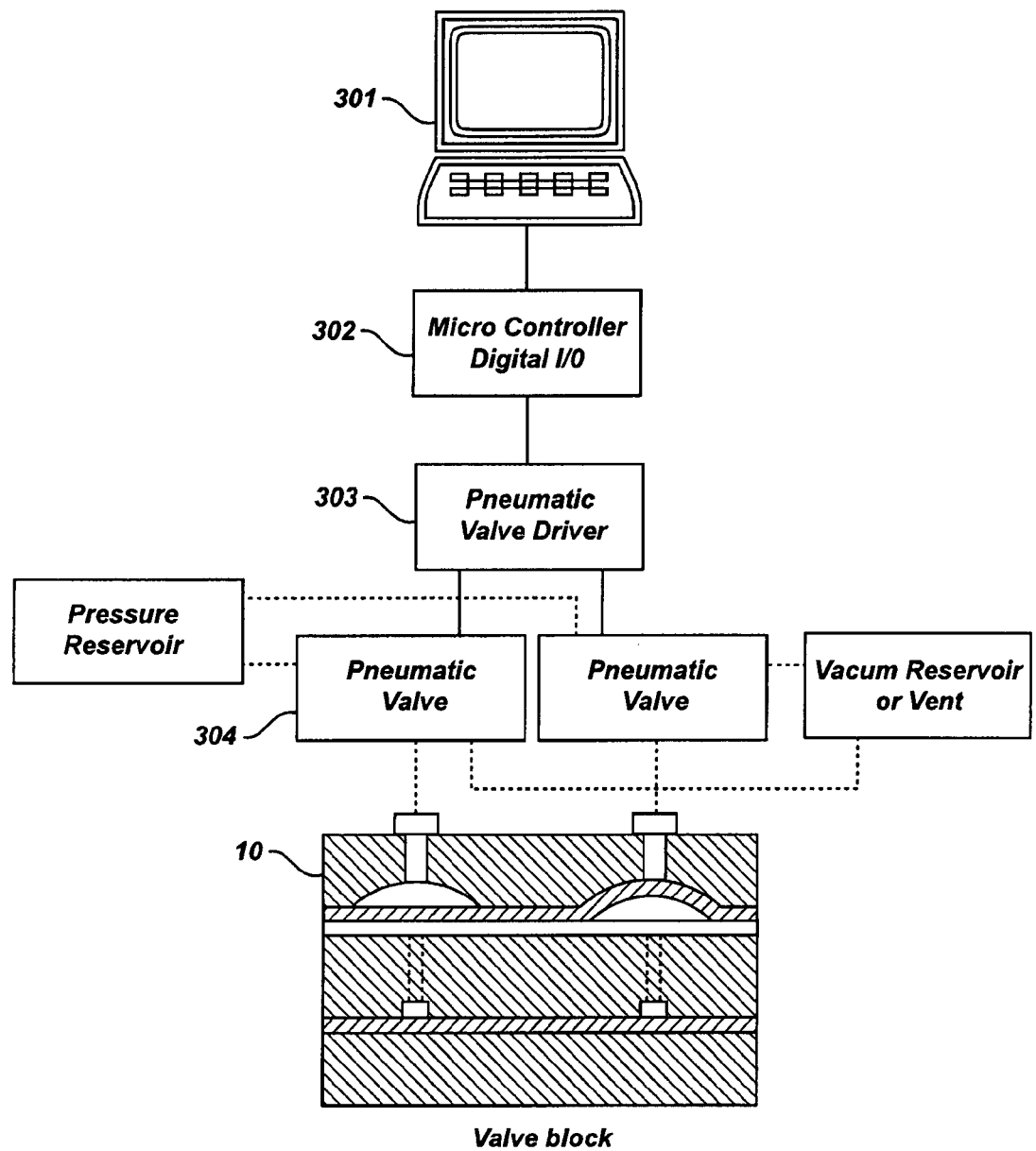
FIG. 14 is a schematic showing various components of a control system for an SMB device.

The simulation of a moving bed in the present invention requires coordinated opening and closing of diaphragm valves during operation, modulation of valve switch times and fluid flow rates, and the ability to collect desired fractions of raffinate and eluate. The process is computer controlled and automated through a standard personal computer interfaced with the SMB unit. A software program governs the pneumatic controller that operates the solenoids which activate individual pneumatic lines, thus controlling opening and closing of individual diaphragm valves. A software program compatible with multiple operating systems (Windows, Linux, or Macintosh) programmed in C++ language is preferred. FIG. 14 gives a simplified diagram of the control system. A computer 301 interfaces a micro controller digital I/O 302, which converts computer signal to pneumatic valve driver 303 instructions. The latter controls operation of individual valves 304 which operate in a valve 10 as previously illustrated in FIG. 3.

EXAMPLE 1

A valve block of the type depicted in FIGS. 4A and 4B was tested to determine the pressure differentials needed for proper opening and closing of the diaphragm ports without causing any leaks. The data resulting from this testing is shown in FIG. 38 along with a depiction of the valve block (3802). Gas pressure was controlled manually for each of the four nipples (FIG. 3, 42) Inlet fluid pressure was also controlled manually and liquid flow rates were measured as a function of pressure differential between the pneumatic and fluid inputs (pneumatic >fluid). A valve inlet 9 transfers a liquid to the linear common groove (FIG. 3, 46). The other outlets are referred to from left to right as 5, 6, 7, 8, and 10' in FIG. 15. The experiments were operated at pressure differentials up to 20 psi. The data, illustrated in FIG. 38, shows that pressure differentials of 1 psi or less were adequate to seal the valve ports at flow rates expected for the SMB system (1-4 mls/min.). Such pressures prevented any leaks from appearing at one minute intervals. Flows were observed for all output ports. It was further observed that back pressure from connection of up to four chromatographic columns did not interfere with flows or cause pressure stress on the system.

EXAMPLE 2

To evaluate continuous isocratic SMB chromatography in purifying a target affinity-tagged protein, a series of experiments were devised and carried out. A pET-EKLIC plasmid encoding his (6)-tagged annexin I (43 Kda) was transformed into BL21 DE3 host cells and target protein expressed using TB autoinduction medium as described in Novagen User Protocol TB383 Rev. H 1005, based on a method summarized by F. William Studier, Protein Expression and Purification, 41: 207 (2005). Cells were harvested after overnight incubation at 30 degrees and soluble extracts prepared using Bug-Buster™, Benzonase®, and rLysozyme (Novagen) according to standard protocols. Crude extracts (16 ml) from 1 gram cell pellets were adjusted to the desired imidazole concentrations and used for purification on Novagen Ni-MAC columns in the SMB device of the present invention according to step batch conventional affinity chromatography or continuous isocratic SMB. Running buffers also contained 50 mM sodium phosphate pH 8.0 and 300 mM sodium chloride.

To establish isocratic conditions for the continuous isocratic SMB experiments, separate runs were made at isocratic concentrations of 115 mM imidazole, 150 mM, 175 mM, and 250 mM. As expected, all of the target protein was recovered in the raffinate at 250 mM imidazole, a known elution concentration. Elution of target into the raffinate was also found at 175 mM. However, at 115 mM and 150 mM, recovery of target protein in good purity and yield was obtained.

Figure 18A:
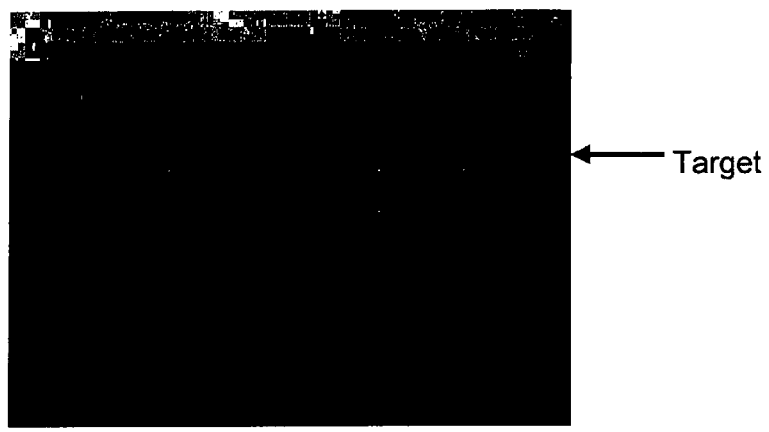
FIGS. 18A and B are scans of Coomassie blue-stained SDS-polyacrylamide gels showing the protein content of various SMB fractions and standards.
Figure 18B:
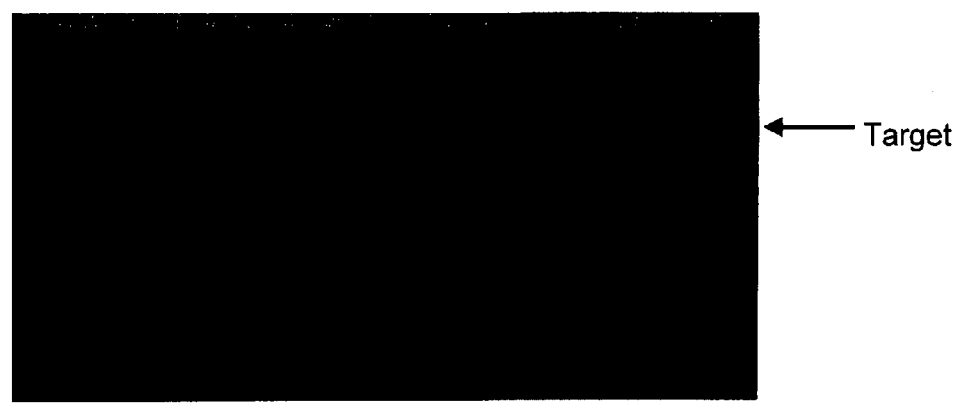

The column fractions collected at the raffinate and eluate ports during experimental affinity step SMB or isocratic SMB runs were analyzed by SDS-PAGE (10-10% gradient gels) and Coumassie Blue staining. Eluate lanes were loaded with approximately 3 μg sample, and raffinate lanes were loaded with approximately 20 μl sample. The results are depicted in FIGS. 18A and 18B. Protein for the various fractions was quantified by BCA assay and spectrophotometrically. Purity was assessed by scanning densitometry. A summary is given in the Table below. The table includes data for a second isocratic run in which the valve switching times were reduced from 2.0 minutes to 1.5 minutes. Data were also compared to a single column batch run (gel not shown).

TABLE

| IMAC Mode | Yield (mg) | Recovery | Target Purity |
|---|---|---|---|
| Isocratic 2 min. switch | 40 | 87% | 98% |
| Isocratic 1.5 minute | 34 | 73% | 96% |
| Step affinity SMB | 51 | 100% | 89% |
| Single column batch | 3.3 mg/ml | 100% | 81% |

In these experiments the isocratic SMB mode produced greater purity than the step affinity mode, which in turn produced greater purity than the single column batch mode. There is some sacrifice of yield when higher purity is sought. The experiments also demonstrate how altering the parameters of the SMB can affect the result. Other advantages of the present invention will be apparent to those skilled in the art.

What is claimed is:

1. A valve module comprising:
   an anchor plate comprising an inlet port extending through the anchor plate and an outlet port extending through the anchor plate;
   a fluid transfer plate comprising
      a first surface comprising an inlet channel and an outlet channel, wherein the inlet channel comprises a first continuous channel linking a plurality of inlet holes extending through the fluid transfer plate and the outlet channel comprises a second continuous channel, separate from the first continuous channel, linking a plurality of outlet holes extending through the fluid transfer plate; and
      a second surface comprising the plurality of inlet holes, the plurality of outlet holes, and a common channel formed in the second surface, wherein the anchor plate and the fluid transfer plate are aligned so that the inlet port aligns with the inlet channel and the outlet port aligns with the outlet channel;
   a membrane positioned adjacent the second surface of the fluid transfer plate;
   a solenoid valve configured to control a flow of a pressurized substance to move at least a portion of the membrane into a closed position to prevent fluid flow, wherein, upon release of pressure on the pressurized substance, the portion of the membrane moves into an open position solely in response to fluid pressure from the fluid flow; and
   a pneumatic plate comprising a plurality of recesses formed in a surface of the pneumatic plate, wherein the membrane is positioned to cover the plurality of recesses, and further wherein a first recess of the plurality of recesses surrounds an inlet hole of the plurality of inlet holes and a first portion of the common channel, wherein a second recess of the plurality of recesses surrounds an outlet hole of the plurality of outlet holes and a second portion of the common channel to provide fluid communication between the inlet hole and the outlet hole under control of pressure changes within the first recess and the second recess.

2. The valve module of claim 1, wherein the solenoid valve comprises a plurality of solenoid valves corresponding to a plurality of portions of the membrane, and wherein the plurality of solenoid valves are configured to control the pressure within the plurality of recesses.

3. The valve module of claim 2, wherein the pneumatic plate further comprises a plurality of bores extending through the pneumatic plate and connecting the plurality of solenoid valves to the plurality of recesses.

4. The valve module of claim 2, further comprising an electronic circuit board electrically connected to the plurality of solenoid valves to control an opening and a closing of each of the plurality of solenoid valves.

5. The valve module of claim 1, further comprising a plurality of inlet ports, each aligned with a corresponding one of a plurality of inlet channels including a second plurality of inlet holes.

6. The valve module of claim 1, further comprising a plurality of outlet ports, each aligned with a corresponding one of a plurality of outlet channels including a second plurality of outlet holes.

7. The valve module of claim 1, wherein the common channel comprises a column access hole extending through the fluid transfer plate, and further wherein the anchor plate further comprises a column access port, wherein the anchor plate and the fluid transfer plate are aligned so that the column access port aligns with the column access hole.

8. The valve module of claim 1, wherein the fluid transfer plate further comprises a second channel formed in the second surface, and further wherein a third recess of the plurality of recesses surrounds a third portion of the common channel and a first portion of the second channel to provide fluid communication between the common channel and the second channel under control of pressure changes within the third recess.

9. The valve module of claim 8, wherein the fluid transfer plate further comprises a third channel formed in the second surface, and further wherein the second channel comprises a transfer hole extending through the fluid transfer plate, and further wherein a fourth recess of the plurality of recesses surrounds the transfer hole and a first portion of the third channel to provide fluid communication between the second channel and the third channel under control of pressure changes within the fourth recess.

10. The valve module of claim 1, wherein the second surface of the fluid transfer plate comprises a second common channel disposed within liquid communicating proximity of (i) an inlet hole of the plurality of inlet holes and (ii) an outlet hole of the plurality of outlet holes.

* * * * *